(12) United States Patent
Fu et al.

(10) Patent No.: US 12,297,484 B2
(45) Date of Patent: May 13, 2025

(54) METHODS, COMPOSITIONS, AND KITS FOR PREPARING NUCLEIC ACID LIBRARIES

(71) Applicant: Genefirst Ltd., Oxfordshire (GB)

(72) Inventors: Guoliang Fu, Oxfordshire (GB); Thomas Dunwell, Oxfordshire (GB)

(73) Assignee: Genefirst Ltd., Oxfordshire (GB)

( * ) Notice: Subject to any disclaimer, the term of this patent is extended or adjusted under 35 U.S.C. 154(b) by 36 days.

(21) Appl. No.: 18/341,446

(22) Filed: Jun. 26, 2023

(65) Prior Publication Data

US 2024/0002906 A1   Jan. 4, 2024

Related U.S. Application Data

(60) Continuation of application No. 17/869,595, filed on Jul. 20, 2022, now Pat. No. 11,993,805, which is a division of application No. 16/605,520, filed as application No. PCT/GB2018/051000 on Apr. 17, 2018, now Pat. No. 11,408,025.

(30) Foreign Application Priority Data

| | | |
|---|---|---|
| Apr. 17, 2017 | (GB) | 1706059 |
| May 25, 2017 | (GB) | 1708384 |
| Nov. 17, 2017 | (GB) | 1719114 |

(51) Int. Cl.

| | |
|---|---|
| C12Q 1/68 | (2018.01) |
| C12N 15/10 | (2006.01) |
| C12Q 1/6806 | (2018.01) |
| C12Q 1/6874 | (2018.01) |

(52) U.S. Cl.
CPC ....... C12Q 1/6806 (2013.01); C12N 15/1093 (2013.01); C12Q 1/6874 (2013.01)

(58) Field of Classification Search
CPC ............................ C12Q 1/6806; C12Q 1/6869
See application file for complete search history.

(56) References Cited

U.S. PATENT DOCUMENTS

| | | |
|---|---|---|
| 11,408,025 B2 | 8/2022 | Fu et al. |
| 2005/0153333 A1 | 7/2005 | Sooknanan |
| 2007/0128598 A1 | 6/2007 | Boender |
| 2009/0227009 A1 | 9/2009 | Sooknanan |
| 2010/0297643 A1 | 11/2010 | Sooknanan et al. |
| 2012/0156729 A1 | 6/2012 | Sooknanan |
| 2014/0274740 A1 | 9/2014 | Srinivasan et al. |
| 2016/0017320 A1 | 1/2016 | Wang et al. |
| 2016/0083786 A1 | 3/2016 | Liu et al. |
| 2016/0298172 A1 | 10/2016 | Chiu et al. |
| 2020/0115736 A1 | 4/2020 | Fu et al. |
| 2023/0121409 A1 | 4/2023 | Fu et al. |

FOREIGN PATENT DOCUMENTS

| | | |
|---|---|---|
| WO | 2004/044239 A1 | 5/2004 |
| WO | 2007/062495 A1 | 6/2007 |

OTHER PUBLICATIONS

Stahlberg, Anders et al., "Simple, multiplexed, PCR-based barcoding of DNA enables sensitive mutation detection in liquid biopsies using sequencing", Nucleic Acids Research Advance Access, Apr. 7, 2016, pp. 1-7.

Gansauge, Marie-Theres et al., "Single-stranded DNA library preparation from highly degraded DNA using T4 DNA Igase", Nucleic Acids Research, Jan. 13, 2017, pp. 1-10.

International Search Report and Written Opinion issued by the European Patent Office, mailed Aug. 8, 2018, in International Application No. PCT/GB2018/051000, 10 pages.

*Primary Examiner* — Kenneth R Horlick
(74) *Attorney, Agent, or Firm* — GREENBERG TRAURIG, LLP

(57) ABSTRACT

This invention relates to methods, compositions and kits for extending a polynucleotide and for preparing sequencing library of polynucleotides involving generating modified target polynucleotide on an adaptor template oligonucleotide and tagging one or two strands of a target sequence. The sequencing library is suitable for massive parallel sequencing and comprises a plurality of double-stranded nucleic acid molecules.

16 Claims, 35 Drawing Sheets

Specification includes a Sequence Listing.

Target polynucleotides

Fragmented target polynucleotides

Hybridising with ATO

Trimming 3' overhang (if any) by a polymerase with 3' exonuclease activity
Extending

A

Enzymatic digestion of DNA

Purification and size distribution check (Optional)

B

Combine suitable amounts of Adapter Template Oligo (ATO) and DNA

Adapter Template Oligo

Heat to denature the DNA, then cool to allow for annealing between DNA and ATOs.

C

Combine with polymerases, buffers and reagents to promote extension of the target DNA.

D     ⇓   Degrade all ATOs and optionally purify modified target polynucleotide.

E     ⇓   First exponential amplification of chosen DNA regions using a pool of primers, and a universal primer.

⇓   Optionally Purify PCR products to remove unused primers and DNA

F     ⇓   Second exponential amplification of chosen DNA regions using a second nested pool of primers, and a second universal primer.

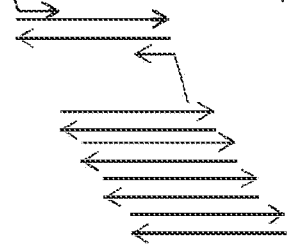

G     ⇓   Purify PCR products to remove unused primers and DNA

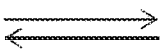

⇓   Library size distribution check and quantification.

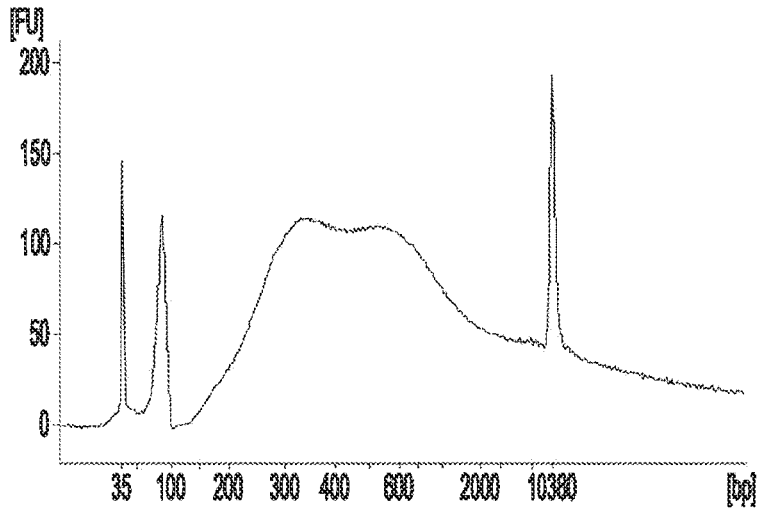

FIG. 13 Continued

E ↓ Linear amplification of adapter template extension product and optional purification
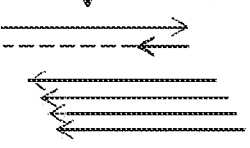

F ↓ Combine suitable amounts of Adapter Template Oligo (ATO) and linear amplification products (CS), Heat to denature the DNA, then cool to allow for annealing between DNA and ATOs.
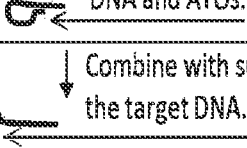

G ↓ Combine with suitable polymerases, buffers and reagents to promote extension of the target DNA.
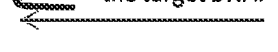

H ↓ Degrade all ATOs.
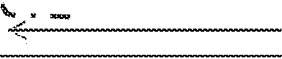

I ↓ Exponential amplification of modified first CS product.
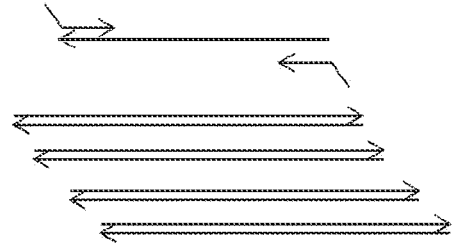

J ↓ Library size distribution check
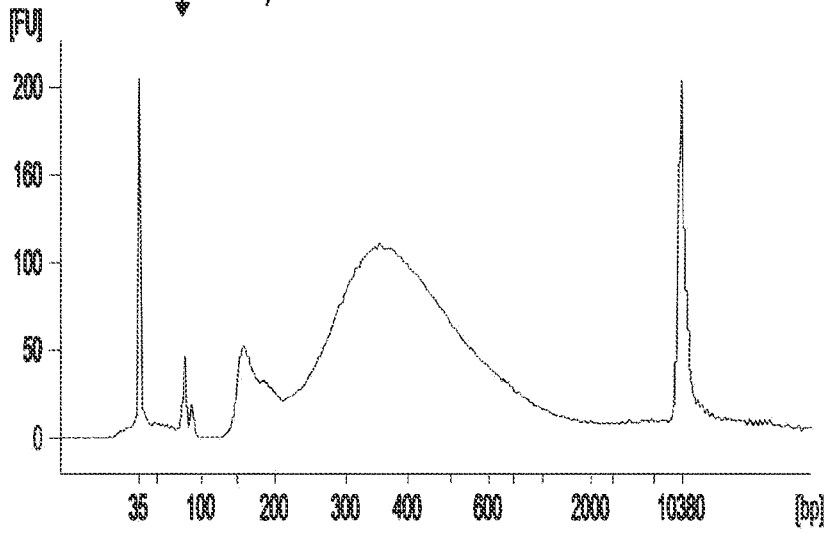

FIG. 14 Continued

METHODS, COMPOSITIONS, AND KITS FOR PREPARING NUCLEIC ACID LIBRARIES

RELATED APPLICATIONS

This application is a continuation application of U.S. application Ser. No. 17/869,595, filed Jul. 20, 2022, now U.S. Pat. No. 11,993,805, which is a divisional application of U.S. application Ser. No. 16/605,520, filed Oct. 16, 2019, now U.S. Pat. No. 11,408,025, which is a U.S. national phase application under 35 U.S.C. 371 of International Application No. PCT/GB2018/051000, filed Apr. 17, 2018, entitled "Methods, Compositions And Kits For Preparing Nucleic Acid Libraries", which claims priority to Great Britain Patent Application No. 1706059.1, filed Apr. 17, 2017, Great Britain Patent Application No. 1708384.1, filed May 25, 2017, and Great Britain Patent Application No. 1719114.9, filed Nov. 17, 2017, the entire contents of each of which are hereby incorporated by reference in their entireties.

REFERENCE TO SEQUENCE LISTING

This specification includes a sequence listing submitted herewith, which includes the file entitled 189372-010102.xml having the following size: 178,995 bytes which was created Jun. 20, 2023, the contents of which are incorporated by reference herein.

BACKGROUND OF THE INVENTION

The present invention is directed to methods and compositions for extending target polynucleotides. An adaptor sequence is added to the 3' end of single stranded nucleic acids.

Next-generation DNA sequencing promises to revolutionize clinical medicine and basic research. However, while this technology has the capacity to generate hundreds of billions of nucleotides of DNA sequence in a single experiment, the error rate of ~1% results in hundreds of millions of sequencing mistakes. These scattered errors become extremely problematic when "deep sequencing" genetically heterogeneous mixtures, such as tumours, or mixed microbial populations.

To overcome limitations in sequencing accuracy, several methods have been reported. Duplex sequencing (Schmitt, et al PNAS 109: 14508-14513) is one of them. This approach greatly reduces errors by independently tagging and sequencing each of the two strands of a DNA duplex. As the two strands are complementary, true mutations are found at the same position in both strands. In contrast, PCR or sequencing errors result in mutations in only one strand and can thus be discounted as technical error. Another approach called Safe-Sequencing System ("Safe-SeqS") was reported by Kinde et al (PNAS 2011 Jun. 7; 108(23):9530-5). The keys to this approach are (i) assignment of a unique identifier (UID) to each template molecule, (ii) amplification of each uniquely tagged template molecule to create UID families, and (iii) redundant sequencing of the amplification products. PCR fragments with the same UID are considered mutant ("supermutants") only if ≥95% of them contain the identical mutation. U.S. Pat. Nos. 8,722,368, 8,685,678, 8,742,606 describe methods of sequencing polynucleotides attached with degenerate base region to determine/estimate the number of different starting polynucleotides. However, these methods cannot easily be used for targeted amplicon sequencing, and often involve ligating to attach degenerate base region. For targeted amplicon based enrichment and sequencing, one cannot easily sequencing fusion or translocation events. Furthermore, sometimes it is difficult to design suitable primer pairs for covering a region of hot spots without losing some regions as un-sequenceable, because the primer site cannot be sequenced. For multiplex amplification in a single tube, overlapping regions cannot be amplified, resulting in loss of sequencing information in the primer binding region of a target polynucleotide. For small size target fragments such as plasma DNA, small RNA or miRNA, designing a pair of primers is also difficult, because there is not much room for designing primer sequence.

Targeted next generation sequencing often involves the analysis of large complex fragments and this is achieved by multiplex PCR (the simultaneous amplification of different target DNA sequences in a single PCR reaction). Results obtained with multiplex PCR, however, are often complicated by artifacts of the amplification products. These include false negative results due to reaction failure and false-positive results (such as amplification of spurious products) due to non-specific priming events. Since the possibility of non-specific priming increases with each additional primer pair, conditions must be modified as necessary as individual primer sets are added.

DETAILED DESCRIPTION

To facilitate an understanding of the invention, a number of terms are defined below.

As used herein, a "sample" refers to any substance containing or presumed to contain nucleic acids and includes a sample of tissue or fluid isolated from an individual or individuals. Particularly, the nucleic acid sample may be obtained from a single cell, an organism or a combination of organisms selected from viruses, bacteria, fungi, plants, and animals. Preferably, the nucleic acid sample is obtained from a mammal. In a preferred embodiment, the mammal is human. The nucleic acid sample can be obtained from a specimen of body fluid or tissue biopsy of a subject, or from cultured cells. The body fluid may be selected from whole blood, serum, plasma, urine, sputum, bile, stool, bone marrow, lymph, semen, breast exudate, bile, saliva, tears, bronchial washings, gastric washings, spinal fluids, synovial fluids, peritoneal fluids, pleural effusions, and amniotic fluid. A "individual sample" may be a single cell, which can be one T cell or one B cell, while the plurality of samples may be many blood cells in a blood sample.

As used herein, the term "nucleotide sequence" refers to either a homopolymer or a heteropolymer of deoxyribonucleotides, ribonucleotides, or other nucleic acids.

As used herein, the term "nucleotide" generally refers to the monomer components of nucleotide sequences even though the monomers may be nucleoside and/or nucleotide analogs, and/or modified nucleosides such as amino modified nucleosides in addition to nucleotides. In addition, "nucleotide" includes non-naturally occurring analog structures. Nucleotide may be deoxyribonucleotides, ribonucleotides, or other nucleic acids As used herein, the term "nucleic acid" refers to at least two nucleotides covalently linked together. A nucleic acid will generally contain phosphodiester bonds, although in some cases nucleic acid analogs are included that may have alternate backbones. Nucleic acids may be single-stranded or double-stranded, as specified, or contain portions of both double-stranded and single-stranded sequence. The nucleic acid may be DNA, both genomic and cDNA, RNA, DNA and RNA mixtures, or DNA-RNA hybrids, where the nucleic acid contains any combination of deoxyribo- and ribo-nucleotides, and any combination of bases, including uracil, adenine, thymine, cytosine, guanine, inosine, xathanine, hypoxathanine, etc. Reference to a "DNA sequence" or "RNA sequence" can include both single-stranded and double-stranded DNA or RNA. A specific sequence, unless the context indicates otherwise, refers to the single stranded DNA or RNA of such sequence, the duplex of such sequence with its complement (double stranded DNA or RNA) and/or the complement of such sequence.

As used herein, the "polynucleotide" and "oligonucleotide" are types of "nucleic acid", and generally refer to primers, or oligomer fragments to be detected. There is no intended distinction in length between the term "nucleic acid", "polynucleotide", and "oligonucleotide", and these terms will be used interchangeably. "Nucleic acid", "DNA", and "RNA" and similar terms also include nucleic acid analogs. The oligonucleotide is not necessarily physically derived from any existing or natural sequence but may be generated in any manner, including chemical synthesis, DNA replication, reverse transcription, or a combination thereof.

As used herein, the terms "target sequence", "target nucleic acid", "target polynucleotide", and "nucleic acids of interest" are used interchangeably and refer to a desired region which is to be either amplified, detected, or both, or is the subject of hybridization with a complementary oligonucleotide, polynucleotide, e.g., a blocking oligomer, or the subject of a primer extension process. The target sequence can be composed of DNA, RNA, analogs thereof, or combinations thereof. The target sequence can be single-stranded or double-stranded. In extension processes, the target polynucleotide which forms a hybridization duplex with an oligonucleotide (template) may be referred to as a "primer", or the target nucleic acid which forms a hybridization duplex with the primer may also be referred to as a "template." A template serves as a pattern for the synthesis of a complementary polynucleotide. A target sequence may be derived from any living or once living organism, including but not limited to prokaryotes, eukaryotes, plants, animals, and viruses, as well as synthetic and/or recombinant target sequences, or a combination thereof.

"Primer" as used herein refers to an oligonucleotide or polynucleotide, whether occurring naturally or produced synthetically, which is capable of acting as a point of initiation of synthesis when placed under conditions in which synthesis of a primer extension product, which is complementary to a nucleic acid strand is induced i.e., in the presence of nucleotides and an agent for polymerization and at a suitable temperature and in a suitable buffer. Such conditions include the presence of four or more different deoxyribonucleoside triphosphates and a polymerization-inducing agent such as DNA polymerase, and/or RNA polymerase, and/or reverse transcriptase, in a suitable buffer ("buffer" includes substituents which are cofactors, or affect pH, ionic strength, etc.), and at a suitable temperature. The primers herein are selected to be substantially complementary to a strand of each specific sequence to be extended. This means that the primers must be sufficiently complementary to hybridize with their respective strands. A non-complementary nucleotide may be present.

As used herein, the term "complementary" refers to the ability of two nucleotide sequences, either randomly or by design, to bind sequence-specifically to each other by hydrogen bonding through their purine and/or pyrimidine bases according to the usual Watson-Crick rules for forming duplex nucleic acid complexes. It can also refer to the ability of nucleotide sequences that may include modified nucleotides, or analogues of deoxyribonucleotides and ribonucleotides, or combinations thereof to bind sequence-specifically to each other by other than the usual Watson Crick rules to form alternative nucleic acid duplex structures.

As used herein, the terms "hybridization" and "annealing" are interchangeable, and refers to the process by which two nucleotide sequences complementary to each other bind together to form a duplex sequence or segment.

The terms "duplex" and "double-stranded" are interchangeable, meaning a structure formed as a result of hybridization between two complementary sequences of nucleic acids. Such duplexes can be formed by the complementary binding of two DNA segments to each other, two RNA segments to each other, or of a DNA segment to an RNA segment, or two segments composed of a mixture of RNA and DNA to one another, the latter structures may also be termed as a hybrid duplex. Either or both members of such duplexes can contain modified nucleotides and/or nucleotide analogues as well as nucleoside analogues. As disclosed herein, such duplexes are formed as the result of binding of one or more blocking oligonucleotides to a sample sequence.

As used herein, the terms "wild-type nucleic acid", "normal nucleic acid", "nucleic acid with normal nucleotides", "wild-type DNA" and "wild-type template" are used interchangeably and refer to a polynucleotide which has a nucleotide sequence that is considered to be normal or unaltered.

As used herein, the term "mutant polynucleotide", "mutant nucleic acid", "variant nucleic acid", and "nucleic acid with variant nucleotides", refers to a polynucleotide which has a nucleotide sequence that is different from the nucleotide sequence of the corresponding wild-type polynucleotide. The difference in the nucleotide sequence of the mutant polynucleotide as compared to the wild-type polynucleotide is referred to as the nucleotide "mutation", "variant nucleotide", or "variation." The term "variant nucleotide(s)" also refers to one or more nucleotide(s) substitution(s), deletion(s), insertion(s), methylation(s), and/or modification changes.

"Amplification" as used herein denotes the use of any amplification procedures to increase the concentration or copy number of a particular nucleic acid sequence within a mixture of nucleic acid sequences. Amplification can be linear amplification, or exponential amplification.

The terms "amplified product" or "amplicon" refer to a fragment of DNA or RNA amplified by a polymerase using primers in an amplification method.

The terms "primer extension product" refer to a fragment of DNA or RNA extended by a polymerase using one or a pair of primers in a reaction, which may involve one pass extension, for example first strand cDNA synthesis, or multiple cycles of extension which may be a linear amplification, or cDNA syntheses, or many cycles of extension, which may be an exponential amplification such as PCR.

The term "compatible" refers to a primer sequence or a portion of primer sequence which is identical, or substantially identical, complementary, substantially complementary or similar to a PCR primer sequence/sequencing primer sequence used in a massive parallel sequencing platform.

The practice of the present invention will employ, unless otherwise indicated, conventional techniques of molecular biology, microbiology and recombinant DNA techniques, which are within the skill of a person skilled in the art. In one aspect, the invention provides a removable template oligonucleotide (RTO) for generating a library of polynucleotides comprising:
(a) a 3' random sequence;
(b) the 3' end is attached with a blocker moiety, which makes RTO unextendible;
(c) a universal sequence, 5' to the random sequence; and
(b) nucleotide sequence/modification (NSM) recognisable by an agent,
wherein RTO serves as a template, does not incorporate into a reaction product and is destroyed/removed after a reaction,
wherein the nucleotide sequence/modification facilitates removal of RTO.

In one embodiment, the 3' blocker moiety and NSM are the same. The 3' blocker moiety and NSM may be biotin, and the agent is avidin or streptavidin. The NSM allows for removal of the RTO, for example by digestion giving strand cleavage, or by affinity purification. The RTO molecule comprises NSM moiety(ies) which render the RTO degradable or non-interfering and non-competing in the reaction(s) following the extension reaction, wherein the moiety is recognisable by an agent, which facilitates digestion/removal of RTO.

The removable template oligonucleotide (RTO) can alternatively be called an adaptor template oligonucleotide (ATO). The terms RTO and ATO can be used interchangeably, and refer to oligonucleotides which serve as templates for extending the ends of the targets in order to modify the targets to add known sequences by polymerase extension. The term adaptor template oligonucleotide (ATO), or removable template oligonucleotide (RTO), refers to a population of sequences having a common (universal) region between each member of the population and a random, variable sequence (referred to as N, where N is each of the four bases). Thus the population of adaptor template oligonucleotides (ATO) refers to a plurality of different sequences due to the random nature of the 3' ends.

The present disclosure provides an adaptor template oligonucleotide (ATO) for extending polynucleotides comprising:
(a) a 3' random sequence;
(b) the 3' end is attached with a blocker, which renders ATO non-extendible; and
(c) a universal sequence, 5' to the random sequence;
wherein ATO serves as a template to direct an extension reaction by a polymerase.

The term universal sequence refers to the entirety of the ATO from its 5' end to the first nucleotide of the random or target specific sequence, and is named due to it being a 'universal sequence' which is present on all ATO.

The ATO molecule can further comprise moiety(ies) which render ATO degradable or non-interfering and non-competing in the reaction(s) following the extension reaction, wherein the moiety is recognisable by an agent, which facilitates digestion/removal of ATO.

The present disclosure provides an adaptor template oligonucleotide (ATO) for extending polynucleotides comprising:
(a) a 3' random sequence of 3 to 36 'N' bases;
(b) a 3' end with a blocker, which renders ATO non-extendible;
(c) a universal sequence, 5' to the random sequence;
(d) optional modified nucleotides or linkages which render the ATO resistant to 3' exonuclease cleavage; and
(e) a moiety which renders the ATO degradeable.

In one embodiment, the moieties are uracil nucleotides, wherein the agent is a dU-glycosylase, or a dU-glycosylase and apurinic/apyrimidinic endonuclease, which is capable of digesting/removing the ATO following the first extension reaction.

In another embodiment, the moieties are ribonucleotides, wherein ribonucleotides are incorporated during oligo synthesis into the ATO in the place of any nucleotides or all nucleotides; wherein the agent is a ribonuclease, which is capable of digesting/removing the ATO following the first extension reaction.

The ATO may be an RNA oligo, or a DNA oligo, or a combination of DNA and RNA oligos.

The ATO may be a combination of one or more different ATO. The combination of ATO may vary in sequence. The combined ATOs may vary in design. The combined ATO may vary in function. Herein the term 'ATO' may refer to a combination of one or more ATOs, to any sequence of ATO, to any designed of ATO with any combination of ATO design features, to any combination of ATO with any combination of functions. When using a combination of one or more ATO there may be variation within the universal sequence with the ATO used, the term universal sequence is used in these cases as well.

In another embodiment, the degradable moiety is restriction enzyme recognisable sequence, wherein the agent is restriction enzyme.

The universal sequence may comprise an RNA polymerase promoter sequence. Any RNA polymerase can be used, such as T7 RNA polymerase, or T3 RNA polymerase, or SP6 RNA polymerase, or a combination thereof. The universal sequence may comprise both an RNA polymerase promoter sequence and/or a priming site, which is located at 3' of the promoter sequence. The priming site provides a primer binding sequence for subsequent amplification.

The universal sequence may be double-stranded or partially double-stranded. Having the universal sequence protected as a double stranded region prevents hybridisation with the randomised 3' ends of the target polynucleotide and the ATO. In one embodiment, the ATO comprises a 5' stem portion sequence which is complementary or partially complementary to all or part of the universal sequence, which are capable of forming a stem-loop structure or split stem-loop structure. The ATO molecule may comprise in 5' to 3' order: 5' stem portion, an RNA polymerase sequence, a priming site sequence, and 3' random/degenerate sequence, a mixture of random/degenerate and specific sequences, or a sequence specific sequence. An RNA polymerase sequence may be located in the loop part, or part of the stem and part of the loop, or in the stem. The loop part may comprise a non-copiable linkage. Alternatively, the loop part may not comprise a non-copiable linkage. Alternatively, the stem part may comprise a non-copiable linkage. If the 5' of the stem portion comprises an additional sequence, a non-copiable linkage may be present between the stem portion and the additional sequence. Alternatively, the stem part may not comprise a non-copiable linkage. In another embodiment, the 5' stem portion comprises a non-copiable linkage. The non-copiable linkage may be selected from group but not limited to C3 Spacer phosphoramidite, or a triethylene glycol spacer, or an 18-atom hexa-ethyleneglycol spacer, or 1',2'-Dideoxyribose (dSpacer).

The double-stranded stem part may comprise non-complementary region(s), wherein the non-complementary region(s) in the universal sequence strand comprises a random, a degenerate sequence(s), or a specially designed mismatch. The stem portion may form two or more split sections separated by one or more non-copiable linkage(s). The stem portion may form two or more split sections separated by one or region of mismatches base pairs.

In another embodiment, an ATO comprises an upper separate strand which is complementary or partially complementary to all or part of the lower strand including the universal sequence. The 5' end of the upper separate strand may comprise a phosphate group.

The ATO may comprise an affinity binding moiety(ies), which is attached at any place of ATO. The affinity binding moiety may be biotin.

The universal sequence of the ATO may comprise a random or sequence specific sequence(s) which acts as an additional unique identification (UID) sequence. The UID sequence(s) may reside within the stem of the ATO. The UID sequence(s) may reside within the loop of the ATO. The UID sequence(s) may reside within the stem and the loop of the ATO, there may be two or more UIDs present within both the stem and/or the loop of the ATO.

The ATO sequence may comprise at any position a non-canonical nucleotide(s) (non-dA, non-dG, non-dT, non-dC), which is a naturally occurring or artificial nucleotide. The non-canonical nucleotide(s) may be a universal nucleotide. The non-canonical nucleotide may comprise an inosine base. The 3' random sequence may comprise in part, or completely of non-canonical nucleotides. The universal sequence may comprise in part, or completely of non-canonical nucleotides.

The 3' end of ATO may comprise modified nucleotide(s) or linkages which make the ATO resistant to 3' exonuclease activity of a DNA polymerase. The modified linkages include phosphorothioate linkage.

The ATO may further comprise a specific sequence 3' of the random sequence, wherein the specific sequence is capable of hybridising to a specific place of the target polynucleotide, or a specific sequence which is not designed for a specific target, and part of the 3' random/degenerated sequence serves as templates on which the polynucleotide is extended by a polymerase. The 3' random sequence of the ATO may be separated into two or more portions by specially designed specific sequences, and part of the 3' random/degenerated/target specific sequence serves as templates on which the target polynucleotide is extended by a polymerase.

The present disclosure further provides a composition comprising at least one nucleic acid polymerase and one or more adaptor template oligonucleotide(s) (ATO(s)) of any combination or mixture from of the ones described. The nucleic acid polymerase can be a DNA or RNA polymerase, or a reverse transcriptase, or mixture of any combination of DNA,RNA polymerases and reverse transcriptase. Preferably the polymerase has strand-displacement activity. The polymerase may have 3' to 5' exonuclease activity. The polymerase may be a mixture of one or more different DNA polymerases, or one or more RNA polymerases, or a combination of one or more DNA or RNA polymerases. The polymerase is a template-dependent polymerase and is not a template-independent polymerase.

The disclosure provides a method of extending a target polynucleotide comprising incubating the target polynucleotide with a composition as described herein under conditions sufficient to allow extension of the 3' end of the target polynucleotide with an ATO(s) as template (termed an "ATO reaction"), wherein ATO(s) may hybridise to any place or a specific place of the target polynucleotide. In another aspect, the method further comprises degrading ATO(s) following extension of the target polynucleotide.

The first ATO reaction can be an extension reaction, wherein the target polynucleotide is extended as primer and ATO(s) acts as a template. Alternatively, the first ATO reaction can be an extension-ligation reaction (nick filling reaction), wherein the target polynucleotide is extended and ligated with the 5' stem portion or the upper strand of ATO(s). Alternatively, the first reaction can be a ligation only reaction, wherein the target polynucleotide is hybridised to 3' random sequence portion of ATO(s) and is directly ligated with the 5' stem portion or the upper strand of ATO(s).

The ATO comprises moiety(ies) which renders ATO degradable, wherein the moiety is recognisable by an agent, which facilitates digestion/removal of ATO. Alternatively, the ATO comprises moiety(ies) which renders the ATO non-interfering and/or non-competing in the reaction following the extension reaction.

In some embodiments, the ATO molecule comprises moiety which is dU bases and is degradable by incubation with a dU-glycosylase (which creates abasic sites) followed by incubation at a temperature that is above 80° C. (introduces breaks within abasic sites), or a mixture of dU-glycosylase and an apurinic/apyrimidinic endonuclease. The method and compositions provided comprise ATO with dU bases and incubation with a dU-glycosylase to degrade the ATO molecule, or incubation with a dU-glycosylase and subsequent incubation at a temperature that is above 80° C. degrades the ATO molecule, or the ATO is incubated with a mixture of dU-glycosylase and an apurinic/apyrimidinic endonuclease. In further aspects, the ATO comprises a ribonucleotide and is degradable with a ribonuclease under conditions sufficient for ribonuclease activity. In related aspects, the ribonuclease is selected from the group consisting of RNase H, RNase HII, RNase A, and RNase T1.

In other embodiments, the moiety may be a modified nucleotide or nucleotide analogous. The modified nucleotide may be a non-canonical nucleotide (non-dA, non-dG, non-dT, non-dC), which is a naturally occurring or artificial nucleotide. The non-canonical nucleotide may be a universal nucleotide. The non-canonical nucleotide may comprise an inosine base, wherein the inosine is used to replace a guanine position in the sequence of ATO, wherein the deoxyInosine preferentially directs incorporation of dC in the growing nascent strand by DNA polymerase, with the expectation and understanding that other residues may be incorporated less frequently.

The modified nucleotides/analogous may be present in the 5' universal sequence (5' universal portion), or in the 3' random/degenerated portion, or the modified nucleotides/analogous may be present both in the 5' universal portion and in the 3' random sequence (3' random portion).

The moiety may be either making the bond of base pairing weaker or may be a modification which is degradable/removable following the first extension ATO reaction. Because of the weak binding, the ATO cannot interfere or compete with the normal primer to bind the same template in the following reaction. Also because of digestion by an agent, the ATO cannot interfere with the subsequent reaction.

The modification providing weaker intermolecular hydrogen bonds of base pairing than standard canonical base pairing can be any naturally occurring nucleotide or artificial nucleotide analogues. Preferred naturally occurring non-canonical nucleotide used in ATO is inosine, which can be used to replace dG to pair with dC but weaker than dG:dC.

Nucleic acid analogues are compounds which are analogous (structurally similar) to naturally occurring RNA and DNA. Nucleic acids are chains of nucleotides, which are composed of three parts: a phosphate backbone, a pentose sugar, either ribose or deoxyribose, and one of four nucleobases. An analogue may have any of these altered. Typically, the analogue nucleobases confer, among other things, different base pairing and base stacking properties. Examples include universal bases, which can pair with all four canonical bases, and phosphate-sugar backbone analogues, which affect the properties of the chain. The 3' random portion of ATO functioning as template, hybridising to any place of a polynucleotide may comprise one or more universal bases.

Universal bases are analog compounds that can replace any of the four DNA bases with weak base-pair interactions. Commonly used universal bases may be 3-nitropyrrole, 5-nitroindole, or 2'-deoxyinosine. Inosine displays a slight bias in nucleotide hybridization with dI:dC being favoured over other pairings.

Canonical bases may have either a carbonyl or an amine group on the carbons surrounding the nitrogen atom furthest away from the glycosidic bond, which allows them to base pair (Watson-Crick base pairing) via hydrogen bonds (amine with ketone, purine with pyrimidine).

Universal bases may pair indiscriminately with any other base, but, in general, lower the melting temperature of the sequence considerably; examples include 2'-deoxyinosine (hypoxanthine deoxynucleotide) and its derivatives, nitroazole analogues, and hydrophobic aromatic non-hydrogen-bonding bases (strong stacking effects). This disclosure has explored this property to make the Inosine containing ATO having lower Tm than normal oligonucleotide so that ATO does not interfere with subsequence reaction, where the annealing temperature is higher than the Tm of ATO's universal portion.

DeoxyInosine, a naturally occurring base, was considered the first "universal" base-meaning that it could base pair with the other natural bases, A, C, G, and T. Studies on deoxyInosine, in fact, indicate that it functions as a specific analog of deoxyGuanosine, although it does not self-aggregate as does deoxyGuanosine.

The weak pairing nucleotides in the universal portion of ATO comprise modified nucleotides, nucleotide analog or/and modified linkages which may be, but not limited to, inosine, dinosine, or phosphorothioate linkages, methylphosphonate linkage. Any modification of the nucleotides or/and linkages can be used, as long as they provide weak pairing compared with native nucleotides or linkages. Weak pairing in the universal portion of ATO may be also relative to the primer used in the subsequent reaction. If the weak pairing nucleotides are normal native nucleotides, the primer used in the subsequent reaction may comprise strong pairing nucleotides which are modified nucleotides or/and modified linkages. The modified nucleotides which provide strong or weak pairing ability may include, but not limited to, LNA, O-me RNA, 2-amino-dA, 2-Thiol-dT, 2-aminopurine, 2' FluoRNA bases, AP-dC, C5-propyne and merhylanalogues of dC and dT, deoxyinosine, deoxyuridine, or superbases nucleotides (Epoch Bioscience).

The ATO may comprise a 5' stem portion sequence which is complementary to a part of the universal sequence, which are capable of forming a stem-loop structure,
  wherein the loop part may comprise a non-copiable linkage.
  wherein the non-copiable linkage may be selected from group but not limited to C3 Spacer phosphoramidite, or a triethylene glycol spacer, or an 18-atom hexa-ethyleneglycol spacer, or 1',2'-Dideoxyribose (dSpacer).

The 5' stem portion sequence may comprise sequence complementary or substantially complementary to a part of the 5' universal sequence, preferably to the part adjacent to the random sequence. In one embodiment, the loop part may comprise a non-copiable linkage, wherein the polymerase in the ATO reaction may contain a strand displacement activity or 5' to 3' exonuclease activity. It is desirable that the target polynucleotide hybridises to 3' random/degenerated/target specific sequence of the ATO only, not to the 5' universal sequence. This is achieved by the stem-loop structure, which prevents the target polynucleotide hybridising to the universal sequence of ATO in the ATO reaction. In the ATO reaction, the target polynucleotide hybridises to the 3' random sequence and is extended by a DNA polymerase, an RNA polymerase. A reverse transcriptase or a mixture of any combination of DNA, RNA polymerases and reverse transcriptase. The extended strand displaces the stem portion and stops at the non-copiable linkage. In addition, in the reaction following the first ATO reaction, the stem-loop structure prevents the ATO from competing with binding to the modified target polynucleotide, so that any added primer can efficiently bind to the modified target polynucleotide for amplification. In this embodiment, the stem portion and non-copiable linkage serve as moiety rendering ATO non-interfering and non-competing in the reaction after the ATO reaction. The ATO may or may not comprise other modifications such as uracil nucleotide(s), or ribonucleotides, which can be digested after the ATO reaction.

In another embodiment, the loop part of ATO may comprise nucleotides which can be digested such as uracil nucleotide(s), or ribonucleotides. In the ATO reaction, the target polynucleotide hybridises to the 3' random sequence and is extended by a DNA polymerase. The extended strand meets with the 5' end of the stem strand which contains 5' phosphate group and is ligated by a DNA ligase. The reaction comprises DNA polymerase with nick filling activity such as Polymerase 1 or Klenow large fragments, and DNA ligase. The ATO molecule may comprise multiple uracil nucleotide, or ribonucleotides. After the ATO reaction, the ATO molecule can be digested.

In yet another embodiment, the loop part of ATO may comprise nucleotides which can be digested such as uracil nucleotide, or ribonucleotides. In the first reaction, the target polynucleotide hybridises to the 3' random sequence adjacent to the 5' end of the stem strand and is ligated to the 5' end of the stem strand by a DNA ligase. The 5' universal sequence portion may comprise multiple uracil nucleotide, or ribonucleotides. After first reaction, the 5' universal sequence portion can be digested.

In yet another embodiment, the ATO comprises an upper separate strand which is complementary or substantially complementary to a part of or whole of the universal sequence, which are capable of forming a partially double-stranded structure. It is desirable that the target polynucleotide hybridises to the 3' random sequence of the ATO only, not to the 5' universal sequence. This is achieved by the double-stranded structure provided by the upper strand, which prevents the target polynucleotide from hybridising to the universal sequence of ATO in the first ATO reaction. The ATO may comprise other modifications such as uracil nucleotide, or ribonucleotides, which can be digested after the first reaction. In the first ATO reaction, the target polynucleotide hybridises to the 3' random sequence and is extended by a DNA polymerase. The extended strand may displace the upper strand. Alternatively, the extended strand meets with the 5' end of the upper strand which has a 5' phosphate group at the 5' end and is then ligated by a DNA ligase. The reaction comprises DNA polymerase with nick filling activity such as Polymerase 1 or Klenow large fragments, and DNA ligase. The 5' universal sequence portion may comprise multiple uracil nucleotides, or ribonucleotides. After first reaction, the 5' universal sequence portion can be digested. In another aspect, in the first reaction, the target polynucleotide hybridises to the 3' random sequence adjacent to the 5' end of the upper strand and is ligated to the 5' end of the upper strand by a DNA ligase. The 5' universal sequence portion as well as 3' random portion may comprise multiple uracil nucleotides. After first reaction, the ATO molecule can be digested.

In the embodiments where the ligation is used, the 5' end of the upper separate strand may comprise a phosphate group, the 3' end of the upper separate strand may comprise a biotin. In the embodiments where the extension is used without ligation, the 5' end of the upper separate strand does not comprise a phosphate group, the 3' end of the upper separate strand does not comprise a biotin, but the upper separate strand may comprise nucleotides which can be digested such as uracil nucleotide.

The random sequence portion can be any length, which may have a range of 3 to 48 nucleotides, preferably having a range of 3 to 36 nucleotides, or most preferably having a range of 12 to 30 nucleotides. Specifically, the random sequence portion has 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more nucleotides. Random sequence may comprise completely random nucleotides, wherein any of four nucleotides can be present at any position. Alternatively, degenerated nucleotides may be present at some places. The random sequence portion may comprise some specific (non-random) nucleotide(s) at some specific location(s), for example the 3' terminus nucleotide may be a specific nucleotide such as T residue, or an A residue, or a G residue, or a C residue. The specific 3' terminus nucleotide is chosen for easy and inexpensive attaching modification, such as biotin, spacer or phosphate blocker. The random sequence may comprise degenerate or semi-degenerate or completely random nucleotides, as well as specific nucleotides, wherein the random nucleotides are present dominantly. The random sequence may also comprise modified nucleotides, either naturally occurring or artificial. These modified nucleotides may be universal base as described above. The random sequence may have a sequence bias, such as making the whole sequence C and G residue rich, meaning greater than 50% of the nucleotides are composed of C and G, or, A and T residue rich, meaning greater than 50% of the nucleotides are composed of A and T. The random sequence, may be in part, or completely, replaced by a target specific sequence.

The ATO is hybridised to target polynucleotide through random sequence at non-stringency condition, where 3' end of polynucleotide is hybridised to the random sequence and in one embodiment is extended using ATO as template.

As described, the random sequence provides function as a template which hybridises to the target polynucleotide and directs extension of the target polynucleotide using ATO as a template. In addition, the random sequence also provides a second function as UID (unique identifier, molecular barcode) in next generation sequencing.

In another embodiment, ATO molecule may comprise 3' additional specific sequence which is located 3' of the random sequence portion. The 3' additional specific sequence may comprise the sequence, which is capable of hybridising to a specific location of a target polynucleotide. The 3' additional specific sequence may comprise restriction enzyme recognition sequence, which, when hybridising to the target sequence, may cause nicking on a target polynucleotide by an enzyme.

The 3' end of ATO may be attached with a blocker group, which makes ATO non-extendable. Any blocker group can be used. Generally, the 3' terminus of the ATO will be "blocked" to prohibit the ATO acting as primer, except when the extension of the ATO is necessary by design where by the 3' will not be blocked and extension will be allowed. "Blocking" can be achieved by attaching a chemical moiety such as biotin or a phosphate group to the 3' hydroxyl of the last nucleotide, which may, depending upon the selected group, serve a dual purpose by also acting as an affinity capture moiety for subsequent removal or capture of the ATO following the ATO reaction. Blocking can also be achieved by removing the 3' OH or by using a nucleotide that lacks a 3' OH such as a dideoxynucleotide. The blocking group may be selected from the group consisting of at least one ribonucleotide, at least one deoxynucleotide, a C3 spacer, a phosphate, a dideoxynucleotide, an amino group, and an inverted deoxythymidine.

The ATO reaction preferably contains polymerase with 3' to 5' exonuclease activity, therefore the ATO molecule preferably comprises modified nucleotides or linkage at the 3' end, which prevent digestion by the polymerase. Any resistant modification can be used. One example is that the 3' end comprises modified linkage between the final nucleotides, preferably the final two nucleotides, at this position so that it comprises a resistant moiety such as phosphorothioate instead of the conventional phosphodiester.

In one embodiment, the 5' universal sequence portion is a part of a sequence providing the function as template for target polynucleotide extending, whose product is equivalent to adding an adaptor for sequencing library preparation via ligation. But the extended sequence-adaptor-alike is newly synthesised and is not attached with any added oligos. The 5' universal sequence portion comprises primer sequence or primer binding sequence, which is compatible to a next (or third) generation sequencing (NGS) or other massive parallel sequencing. For example, the 5' universal sequence portion may comprise sequencing primer sequences for Illumina platform, and/or anchoring primer sequences for Illumina platform.

The 5' universal sequence portion may form a stem-loop or hairpin structure, where the stem part end is close to the 5' end of random sequence portion. The 5' end of the stem may form a 5' overhang. The stem part can have any length. The stem part can have any length ranging from 3 to 30 nucleotides, preferably 4 to 24 nucleotides. The stem part may be fully double-stranded, or preferably not fully double-stranded. The stem part may comprise non-pairing region(s). The non-pairing region(s) may comprise random sequence, which serves a function of UID (molecular barcode) in NGS. The stem part may comprise sequence recognisable and cleavable by an enzyme, for example restriction enzyme site. The stem formation may prevent the hybridisation of the universal sequence to the target polynucleotide. The loop part can be any length. The loop part can be any length ranging from 0 to 36 nucleotides, preferably 1 to 30 nucleotides. The loop may comprise in part of completely of a nucleotide analog or other chemical linkage, which is non-copiable by a polymerase, for example an abasic site, hexethylene glycol (HEG) monomer, an 18-atom hexa-ethyleneglycol spacer, or an 1',2'-Dideoxyribose (dSpacer). The non-copiable linker prevents polymerase mediated extension on the 5' part of the ATO.

ATO molecule comprises nucleotides selected from the group consisting of 2'-deoxythymidine 5'-monophosphate (dTMP), 2'-deoxyguanosine 5'-monophosphate (dGMP), 2'-deoxyadenosine 5'-monophosphate (dAMP), 2'-deoxycytidine 5'-monophosphate (dCMP), 2'-deoxyuridine 5'-monophosphate (dUMP), thymidine monophosphate (TMP), guanosine monophosphate (GMP), adenosine monophosphate (AMP), cytidine monophosphate (CMP), uridine monophosphate (UMP), a base analog, and combinations thereof. It is also contemplated that the ATO comprises a modified nucleotide or linkage modification as defined herein.

Modified oligonucleotides or polynucleotides may comprise both one or more sugar and/or one or more internucleotide linkage of the nucleotide units in the oligo-polynucleotide is replaced with "non-naturally occurring" groups. In one aspect, this embodiment contemplates a peptide nucleic acid (PNA). In PNA compounds, the sugar-backbone of a polynucleotide is replaced with an amide containing backbone. Modified oligo-polynucleotide backbones may contain a phosphorus atom include, for example, phosphorothioates, chiral phosphorothioates, phosphorodithioates, phosphotriesters, aminoalkylphosphotriesters, methyl, and other alkyl phosphonates. Modified oligonucleotide or polynucleotides may also contain one or more substituted sugar moieties. Further modifications include those that extend the genetic code such as, without limitation, Iso-dC and Iso-dG. Iso-dC and Iso-dG are chemical variants of cytosine and guanine, respectively. Iso-dC will hydrogen bond with Iso-dG but not with dG. Similarly, Iso-dG will base pair with Iso-dC but not with dC. In one aspect, a modification of the sugar includes Locked Nucleic Acids (LNAs).

A target polynucleotide may be randomly or specifically or a combination of randomly and specifically fragmented either naturally or artificially, the 3' end of the fragmented target polynucleotide is extended after hybridisation with the random or target specific sequence of an ATO. The combination of the random 3' end sequence of the target polynucleotide and extended part on random template provides a unique identification (UID, molecular barcode) sequence which can be used for grouping sequencing reads into family. In addition, ATO may comprise one or more additional UID(s) located in the universal sequence. The additional UID may be located in the loop, close to the 5' of the stem part and random sequence portion. The additional UID may be located in the stem, anywhere between the 3' random sequence and the loop. The additional UID can have any length. The additional UID can have any length, which may have a range of 2 to 48 nucleotides, preferably have a range of 3 to 36 nucleotides. The additional UID may comprise completely random nucleotides, wherein any of four nucleotides can be present at any one place. Alternatively, degenerated nucleotides may be present at some places.

The ATO molecule may comprise a non-canonical nucleotide, analog, or modification, which is recognisable and cleavable by an agent. The non-canonical nucleotide is selected from the group consisting of dUMP, dIMP, and 5-OH-Me-dCMP. The agent capable of cleaving a base portion of the non-canonical nucleotide is an N-glycosylase enzyme. The N-glycosylase is selected from the group consisting of Uracil N-Glycosylase (UNG), hypoxanthine-N-Glycosylase, and hydroxy-methyl cytosine-N-glycosylase. When the non-canonical nucleotide is dUMP and the enzyme capable of cleaving a base portion of the non-canonical nucleotide is UNG. When the non-canonical nucleotide is dUMP, the enzyme capable of cleaving a base portion of the non-canonical nucleotide is UNG, and the phosphodiester backbone is cleaved with DMED. In one embodiment, the uracil nucleotides are incorporated into the ATO during oligo synthesis in the place of thymine nucleotides. The ATO comprising a non-canonical nucleotide may be synthesized in the presence of two or more different non-canonical nucleotides, whereby an ATO comprising two or more different non-canonical nucleotides is synthesized. When the ATO comprising a non-canonical nucleotide is synthesized in the presence of three canonical nucleotides and a non-canonical nucleotide, or all four canonical nucleotides and a non-canonical nucleotide wherein the non-canonical nucleotide is provided at a ratio suitable for degrading the ATO following the ATO reaction. Typically, the base excision repair enzyme can be selected from the group consisting of DNA glycosylases, AP endonucleases and deoxyphosphodiesterases. Preferably, the DNA glycosylase can be selected from the group consisting of uracil-DNA glycosylase, 3-methyladenine DNA glycosylase, pyrimidine hydrate-DNA glycosylase, FaPy-DNA glycosylase and thymine mismatch-DNA glycosylase. More preferably, the DNA glycosylase is uracil-DNA glycosylase. Uracil-DNA Glycosylase (UDG) or Uracil-N-Glycosylase (UNG) is an enzyme that catalyzes the release of free uracil from single stranded and double stranded DNA of greater than 6 base-pairs.

In one embodiment, the ATO molecule may comprise ribonucleotides, wherein ribonucleotides are incorporated during oligo synthesis into the ATO in the place of any nucleotides or all nucleotides; wherein the agent is RNase, which is capable of degrading/removing the ATO following the ATO reaction. The ATO may be RNA for the whole length, or be partly made by RNA. Any part of ATO can be RNA, preferably the universal sequence portion is RNA.

In another embodiment, the ATO sequence may comprise restriction enzyme recognising sequence, which is located in the universal sequence or in the 3' additional specific sequence; wherein the agent is a restriction enzyme, which is capable of degrading/removing the ATO following the ATO reaction. The restriction enzyme recognising sequence may be located in the stem part of ATO, which can be cleaved by a restriction enzyme.

In another embodiment, the ATO molecule may comprise affinity binding moiety, which is attached in any position of ATO; wherein the agent is protein or antibody, which is capable of removing the ATO following the ATO reaction. For example, the affinity binding moiety is biotin; wherein the agent is avidin or streptavidin. In certain embodiments, ATO may comprise one or more moieties incorporated into 5' or 3' terminus or any internal position of ATO that allow for the affinity removal of ATO from reaction mixture following the ATO reaction. Preferred affinity moieties are those that can interact specifically with a cognate ligand. For example, affinity moiety can include biotin, digoxigenin etc. Other examples of capture groups include ligands, receptors, antibodies, haptens, enzymes, chemical groups recognizable by antibodies or aptamers. The affinity moieties can be immobilized on any desired substrate/solid support. Examples of desired substrates include, e.g., particles, beads, magnetic beads, optically trapped beads, microtiterplates, glass slides, papers, test strips, gels, other matrices, nitrocellulose, or nylon. For example, when the capture moiety is biotin, the substrate can include streptavidin. In some instances, the solid support is a bead. Examples of beads include, but are not limited to, streptavidin beads, agarose beads, magnetic beads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, and anti-fluoro chrome microbead.

While part of random sequence of RTO serves as unique identification (UID) sequence, RTO may comprise additional UID located in the universal sequence portion.

The present disclosure provides a method for generating a library of polynucleotides comprising:
(i) generating a modified target polynucleotide using a target polynucleotide from a sample as primer and using a removable template oligonucleotide (RTO) of any one of the above-mentioned RTO as template;
(ii) removing RTO; and
(iii) generating a first complement sequence (CS) of the modified target polynucleotide using a first primer, the first primer comprising a universal sequence,
wherein generating comprise extending primer hybridised to a template by a polymerase.

The present disclosure therefore provides a method for extending a population of target polynucleotides having single stranded 3' ends comprising:
(i) incubating the target polynucleotides with adaptor template oligonucleotides (ATO) having
(a) a 3' random sequence;
(b) a 3' end with a blocker, which renders ATO non-extendible; and
(c) a universal sequence, 5' to the random sequence,
wherein the target polynucleotides hybridise to the 3' random sequence of the ATO;
(ii) performing a polymerase extension of the target polynucleotides using the ATO as a template, thereby producing extended target polynucleotides having a 3' universal sequence.

The method can further comprise (iii) generating a first complement sequence (CS) of the modified target polynucleotides, wherein generating the first CS comprises polymerase extension from the 3' universal sequence using the modified target polynucleotides as templates.

The present disclosure provides a method for extending polynucleotides comprising:
(i) generating a modified target polynucleotide by incubating target polynucleotides with the composition described above, wherein the 3' end of the target polynucleotide hybridises to the 3' random sequence of an adaptor template oligonucleotide (first ATO) in an enzymatic first ATO reaction, in which the 3' end of the target polynucleotide is extended using an ATO as template, wherein if a 3' overhanging end is present, the 3' end of the target polynucleotide is trimmed before extension takes place.

In one embodiment, the modified polynucleotide, following 3' end extension on ATO, is optionally incubated with a single stranded DNA circularization ligase which results in circularization of the single stranded modified polynucleotide.

The method further comprises (ii) generating a first complement sequence (CS) of the modified target polynucleotide.

The step (ii) may comprise using the modified target polynucleotide as a template for one round of amplification, as a template for to sequential rounds of amplification, as a template for to sequential rounds of amplification separated by a purification step.

In one embodiment, said generating first CS comprises extension using a first primer, and using the modified target polynucleotide as template, wherein the first primer is hybridised to the modified target polynucleotide and is extended by a polymerase. The first primer anneals to the 3' extended universal region of the modified target polynucleotide. The first primer may comprise additional sequence compatible to a NGS platform, for example a 5' tail containing necessary sequences.

In another embodiment, said generating first CS comprises in vitro transcription using an RNA polymerase using the double-stranded RNA polymerase promoter region in the modified target polynucleotide generated by extending on an ATO containing RNA polymerase promoter. In another embodiment the double strand RNA polymerase of the modified target polynucleotide is generated by hybridising a nucleotide with the modified target polynucleotide after digestion and/or removal of the ATOs.

In yet another embodiment, said generating first CS comprises heat denaturing the modified target polynucleotide, self-annealing the 3' stem-loop structure of the modified target polynucleotide and self-priming to extend to form the first CS.

In yet another embodiment, said generating first CS comprises target specific primer annealing to the modified target polynucleotide and extension by a polymerase. The target-specific primer anneals to the target sequence of interest. The double-stranded end of the first CS can be ligated to an adaptor.

The method may further comprise digesting ATO before or after generating a first complement sequence (CS) of the modified target polynucleotide.

The method may further comprise affinity capturing before or after generating a first complement sequence (CS) of the modified target polynucleotide.

In the first ATO reaction, the method may comprise extension and ligation, wherein a DNA polymerase extends the 3' end of the target, and a DNA ligase ligates the extended target sequence to the 5' stem portion of ATO or upper separate strand of ATO.

The method may further comprise generating a modified first CS by incubating first CS with the composition described above, wherein the 3' end of the first CS hybridises to the 3' random sequence of an adaptor template oligonucleotide (second ATO) in an enzymatic second ATO reaction, in which the 3' end of the first CS is extended using an ATO as a template, wherein if 3' overhang is present, the 3' end of the first CS is trimmed before extension takes place, wherein the second ATO comprises a different 5' universal sequence of the first ATO.

The method may further comprise generating a modified first CS by ligating adaptors into the products of step (ii).

The method may further comprise extending a second primer hybridized to the first CS or to the modified first CS, thereby generating a second CS, wherein the second primer comprises a target-specific portion or universal sequence, or both 3' target specific and 5' universal sequence.

The method may further comprise separation of the modified target polynucleotide reaction into two separate reactions, where each reaction contains a primer complementary to the universal region of the modified target polynucleotide, with a reaction comprising a target-specific second primer, or pool of target-specific primers, complementary to forward strand of a target sequence, and a second reaction comprising a target-specific second primer, or pool of target-specific primers, complementary to reverse strand of the target sequence, wherein forward strand and reverse strand of the target sequence are complementary.

In another embodiment, the pools of target-specific primers can contain a mixture of primers, where individual primers can target either the forward or reverse strand for different targets, such that the final pool can target different regions of both the forward and reverse strands. Wherein the forward strand and reverse strand of the target sequence are complementary, and the forward and reverse target specific primers are separated into the two different pools of primers as long as consideration is taken that no two primers which target the forward and reverse strands are added to the same pool if they are capable of together acting as primers for PCR resulting in the generation of unwanted PCR products. Further, all references to 'forward' and/or 'reverse' pools allows for each pool to contain primers which target both the forward and reverse strands, as mentioned above.

The method may further comprise hybridising a primer complementary to the universal region of the modified target polynucleotide, followed by one or more rounds of linear amplification to generate a first complement sequence (CS). The linear amplification reaction product is separated into two separate reactions, where each reaction contains a primer complementary to the universal region of the modified target polynucleotide, with a reaction comprising a target-specific second primer, or pool of target-specific primers, complementary to forward strand of a target sequence, and a second reaction comprising a target-specific second primer, or pool of target-specific primers, complementary to reverse strand of the target sequence, wherein forward strand and reverse strand of the target sequence are complementary.

The method may further comprise an end repair step of the double strand target polynucleotide followed by ligation of a double strand adaptor. The ligation product is then hybridised with a primer complementary to the universal region of the target polynucleotide ligation product, followed by one or more rounds of linear amplification. The linear amplification reaction product is separated into two separate reactions, where each reaction contains a primer complementary to the universal region of the modified target polynucleotide, with a reaction comprising a target-specific second primer, or pool of target-specific primers, complementary to forward strand of a target sequence, and a second reaction comprising a target-specific second primer, or pool of target-specific primers, complementary to reverse strand of the target sequence, wherein forward strand and reverse strand of the target sequence are complementary.

When the target polynucleotides in a sample are double-stranded and second primers are target specific primers, the reaction after ATO reaction for target specific amplification may comprise dividing the ATO reaction products or linearly amplified first CS product into two separate reactions, forward reaction comprises a target-specific second primer(s) complementary to forward strand of a target sequence, reverse reaction comprises a target-specific second primer(s) complementary to reverse strand of the target sequence, wherein forward strand and reverse strand of the target sequence are complementary.

In one aspect, said generating the first CS comprises one pass extension or linear amplification using the first primer, which is a universal primer targeting the 3' extended universal part of the polynucleotide. The linear amplification may have 1-30 cycles, or 2-25 cycles, or 3-24 cycles, or 4-23 cycles or 5-22 cycles, 6-21 cycles, or 7-20 cycles or 8-19 cycles or 9-18 cycles or 10-17 cycles.

In another aspect, said generating the first CS comprises reverse transcription reaction using reverse transcriptase if the target is RNA.

The method may further comprise exponential amplification using first primer and second primer. The first primer may be a universal primer targeting the 3' extended universal part of the modified target polynucleotide; the second primer may be a universal primer targeting the 3' extended universal part of the first CS. Alternatively, the second primer is a target specific primer annealing to a specific region of interest of the first CS. The second primer may be a set of multiple primers targeting multiple sequence regions of interest. When the second primer is a target-specific primer, after linear or exponential amplification using the second primer, a nested target-specific third primer is used for a further amplification.

The first primer, second primer, or third primer may comprise a sample barcode (SBC) sequence and additional universal sequence(s) necessary for compatibility with an NGS platform.

The method may comprise fragmenting, or fragmenting/tagging target polynucleotides before the first ATO reaction.

In one embodiment, said fragmenting and/or tagging target polynucleotides comprises contacting double-stranded polynucleotides with transposase bound to transposon DNA, wherein the transposon DNA comprises a transposases binding site and universal sequence, wherein the transposases/transposon DNA complex bind to target locations on the double-stranded polynucleotide and cleave the double-stranded polynucleotides into a plurality of double-stranded fragments, with each double-stranded fragment having the transposon DNA bound to each 5' end of the double-stranded fragment. The method further comprise heat denaturing the fragmented target polynucleotides before the first ATO reaction. The transposase may be Tn5 transposase. The transposon DNA may comprise a barcode sequence, and may comprise a priming site. The transposon DNA comprises a double-stranded 19 bp Tnp binding site and an overhang, wherein the overhang may comprise a UID and a priming site. The transposon DNA comprises a double-stranded 19 bp Tnp binding site and a nucleic acid stem-loop structure. The bound transposases may be removed from the double-stranded fragments before the first ATO reaction. The Tn5 transposases are complexed with the transposon DNA, the Tn5 transposase/transposon DNA complex bind to target locations along the double-stranded genomic DNA cleaving the double-stranded genomic DNA into plurality of double-stranded fragments. The transposon DNA comprises a double-stranded 19 bp Tn5 transposase (Tnp) binding site at one end, and a long single-stranded overhang including a barcode region, a priming site, and other sequence. Upon transposition, the Tnp and the transposon DNA bind to each other and dimerize to form transposomes. The transposomes then randomly capture or otherwise bind to the target polynucleotides. Then, the transposases in the transposome cut the genomic DNA with one transposase cutting an upper strand and one transposase cutting a lower strand to create a DNA fragment. The transposon DNA is thus inserted randomly into the polynucleotides, leaving a 9-bp gap on both ends of the transposition/insertion site. The result is a DNA fragment with a transposon DNA Tnp binding site attached to the 5' position of an upper strand and a transposon DNA Tnp binding site attached to the 5' position of a lower strand.

In another embodiment, said fragmenting target polynucleotides comprise contacting double strand DNA with a CRIPSR/Cas9 enzyme bound to a guide RNA, where in the CRISPR/Cas9/guide RNA complex binds to a region of the target polynucleotide determined by the sequence of the guide RNA. The CRISPR/Cas9/guide RNA/DNA complex leads to a double strand break as determined by the sequence targeted by the guide RNA. In another embodiment, only a single strand break is induced.

Said fragmenting may comprise use of targeted fragmentation using genome editing tool. The genome editing tool may comprise a clustered regularly interspaced short palindromic repeats and CRISPR-associated protein 9 enzyme (CRISPR/Cas9). The enzyme may belong to Class I. The Class I enzyme is a Type I, Type III, or Type IV enzyme. The enzyme may belong to Class II. The Class II enzyme is a Type II, Type V, or Type VI enzyme. The enzyme can comprise any combination of Class I and Class II enzymes. The combination can compose any combination of Type I, Type II, Type III, Type IV, Type V, or Type VI enzymes. A pool of guide RNAs are used to target multiple regions of the genome to induce DNA breaks. The DNA breaks may be single strand breaks, or double strand breaks. The DNA breaks may be combination of double and single strand breaks. The pool consists of any number of guide RNAs.

In another embodiment, said fragmenting and tagging target polynucleotides comprises contacting single-stranded target polynucleotides with random primer which comprises 5' universal sequence and 3' random sequence, extending the random primer on the target polynucleotide to generate 5' tagged fragmented polynucleotides.

The target polynucleotide or the fragmented target polynucleotide comprises a free 3' hydroxyl group. The target polynucleotide may be single-stranded DNA, or single-stranded RNA, or combination of single-stranded RNA and single-stranded DNA.

One embodiment provides a method for extending polynucleotides comprising:
mixing the target polynucleotide with DNA polymerase, adaptor template oligonucleotide (ATO) described above, comprising 3' random sequence which has 3' end blocked and modified to be resistant to 3'exonuclease activity;
incubating the mixture under conditions that promote annealing, trimming 3' overhang end if any is present, and extension generating a modified target polynucleotide; and
optionally degrading the ATO.

One embodiment provides a method for generating a sequencing library comprising:
mixing the target polynucleotides with DNA polymerase(s), adaptor template oligonucleotide (ATO) described above, comprising 3' random sequence which has 3' end blocked and modified to be resistant to 3'exonuclease activity;
incubating the mixture under conditions that promote annealing, trimming 3' overhang end if any is present, and extension to generate a modified target polynucleotide;
optionally degrading the ATO; and
amplifying the modified target polynucleotide using primers compatible to a NGS platform, with one, or two, or more rounds of linear and/or exponential amplification.

The method further comprises fragmenting the target polynucleotide prior mixing. The target polynucleotide may be naturally occurring fragmented polynucleotide. The naturally occurring fragmented polynucleotide may be circulating cell free nucleic acid of plasma. Said fragmented target polynucleotides may comprise contacting double-stranded polynucleotides with transposase bound to transposon DNA, wherein the transposon DNA comprises a transposases binding site and universal sequence, wherein the transposases/transposon DNA complex bind to target locations on the double-stranded polynucleotide and cleave the double-stranded polynucleotides into a plurality of double-stranded fragments, with each double-stranded fragment having the transposon DNA bound to each 5' end of the double-stranded fragment.

Further provided is a method for generating a sequencing library comprising:
adding adaptor sequence to single-stranded target polynucleotide according to ATO and compositions described above by extending single-stranded target polynucleotide on an ATO template; and amplifying the adaptor-tagged target polynucleotide using primers compatible to a NGS platform, wherein the ATO comprises adaptor sequence in the universal portion. Adaptor sequence provides a priming sequence for both amplification and sequencing of nucleic acid fragments and is used, in some aspects, for next generation sequencing applications. In further aspects, an "adaptor sequence" is used as a promoter sequence for generation of RNA molecules, wherein the promoter sequence is, for example and without limitation, a T7 promoter sequence or an SP6 promoter sequence.

The present disclosure provides a method for generating a library of polynucleotides comprising:
(i) generating a modified target polynucleotide by using a target polynucleotide from a sample hybridising to the 3' random sequence of adaptor template oligonucleotide (ATO) of any one of above mentioned ATO (first ATO) in an enzymatic first reaction which adds an adaptor sequence to the 3' end of the target polynucleotide; and
(ii) generating a first complement sequence (CS) of the modified target polynucleotide using a first primer, which comprises the universal sequence, and using the modified target polynucleotide as template, wherein the first primer is hybridised to the template and is extended by a polymerase.

The target polynucleotide is preferably fragmented either naturally or artificially. The target polynucleotide may be any nucleic acids such as DNA, cDNA, RNA, mRNA, small RNA, or microRNA, or any combination thereof. The target polynucleotide may comprise a plurality of target polynucleotides. Each of the target polynucleotides of the plurality may comprise different sequences or the same sequence. One or more of the target polynucleotides or plurality of target polynucleotides may comprise a variant sequence.

Depending on the type of target polynucleotide and ATO which are either DNA and/or RNA, the methods can utilize reverse transcription or primer extension. A primer extension reaction can be a single primer extension step. A primer extension reaction can comprise extending one or more individual primers once. A primer extension reaction can comprise extending one or more individual primers in one step. In the step (i) the 3' end of or trimmed 3' end of the target polynucleotides act as primer, which is extended using ATO as template, in the step (ii) the extension or amplification primers are the first primer which anneal to the 3' extended part of the target polynucleotide.

In one embodiment in the step (i), the 3' end of the target polynucleotides acting as primers are hybridised to the ATO through the 3' end of the sequence which may be randomly fragmented or specifically fragmented, are trimmed to remove 3' overhang, if any is present, by the 3' to 5' exonuclease activity of a polymerase, and is extended using ATO as template to generate modified target polynucleotides. Because of the nature of randomness of ATO's 3' random sequence portion, the perfect hybridisation between the 3' end of the target polynucleotides and a ATO may not be readily obtained, less stringent conditions are applied. For example, high concentration of ATO may be used, low temperature of hybridization such as 4 degree C. may be used, and/or multiple cycle of extension may be used, and/or longer hybridization times. Extension may be carried out by any polymerase and/or any reverse transcriptase, or mix of different polymerases. Preferably the DNA polymerase may have a 3' to 5' exonuclease activity, so that any 3' overhang if present is digested (trimmed) and extension can take place. The DNA polymerase may contain strand displacement activity, so that the stem-loop structure and the double-stranded universal portion of the ATO molecules can be opened and copied. Alternatively, the DNA polymerase may contain 5' to 3' exonuclease activity, so that the 5' end of stem-loop structure and the double-stranded universal portion of the ATO molecules can be digested and the lower strand of ATO is copied. The DNA polymerase is preferably active at low temperature. The polymerase may contain a mix of different polymerases which may have 3' to 5' exonuclease activity, 5' to 3' exonuclease activity and/or strand displacement activity. The polymerases that may be used to practice the methods disclosed herein include but are not limited to Deep VentR™ DNA Polymerase, LongAmp™ Taq DNA Polymerase, Phusion™ High-Fidelity DNA Polymerase, Phusion™ Hot Start High-Fidelity DNA Polymerase, VentR® DNA Polymerase, DyNAzyme™ II Hot Start DNA Polymerase, Phire™ Hot Start DNA Polymerase, Crimson LongAmp™ Taq DNA Polymerase, DyNAzyme™ EXT DNA Polymerase, LongAmp™ Taq DNA Polymerase, Taq DNA Polymerase with Standard Taq (Mg-free) Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, VentR® (exo-) DNA Polymerase, Hemo KlenTaq™, Deep VentR™ (exo-) DNA Polymerase, ProtoScript® AMV First Strand cDNA Synthesis Kit, ProtoScript® M-MuLV First Strand cDNA Synthesis Kit, Bst DNA Polymerase, Full Length, Bst DNA Polymerase, Large Fragment, Taq DNA Polymerase with ThermoPol Buffer, 9° Nm DNA Polymerase, Crimson Taq™ DNA Polymerase, Crimson Taq™ DNA Polymerase with (Mg-free) Buffer, Deep VentR™ (exo-) DNA Polymerase, Deep VentR™ DNA Polymerase, DyNAzyme™ EXT DNA Polymerase, DyNAzyme™ II Hot Start DNA Polymerase, Hemo KlenTaq™, Phusion™ High-Fidelity DNA Polymerase, Phusion™ Hot Start High-Fidelity DNA Polymerase, Sulfolobus DNA Polymerase IV, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, Large Fragment, Bst DNA Polymerase, Large Fragment, DNA Polymerase I (*E. coli*), DNA Polymerase I, Large (Klenow) Fragment, Klenow Fragment (3'-5' exo-), phi29 DNA Polymerase, T4 DNA Polymerase, T7 DNA Polymerase (unmodified), Reverse Transcriptases and RNA Polymerases, AMV Reverse Transcriptase, M-MuLV Reverse Transcriptase, phi6 RNA Polymerase (RdRP), SP6 RNA Polymerase, and T7 RNA Polymerase.

Ligases that may be used to practice the methods of the disclosure include but are not limited to T4 DNA ligase, T4 RNA ligase, *E. coli* DNA ligase, and *E. coli* RNA ligase.

Multiple cycles of extension may be carried out through thermo cycling of temperatures: annealing, extension, and denaturing. The modified target polynucleotide has extended 3' part, which may comprise some random sequence and a universal sequence providing a binding site for a primer. The extended 3' part may also comprise additional UID.

In one embodiment, in the step (i), if the universal portion of ATO comprises weak pairing nucleotides such as Inosine, the removal of ATO after first extension reaction may be not needed. Otherwise the removal or digestion of ATO from the reaction mix may be performed by any means. For example, if the ATO comprises Uracil residues, the ATO is digested/removed by UNG digestion; if the ATO comprises RNA, the ATO is digested/removed by RNase digestion; if the ATO comprises restriction enzyme site, the ATO is digested/removed by restriction enzyme digestion; or if the ATO comprises biotin, the ATO is removed by capturing on streptavidin beads. In another embodiment, the ATO may not need to be digested or removed from the reaction mix if the ATO comprises the hairpin/stem-loop structure (FIGS. 3B and 3C), as the hairpin structure of ATO makes the hybridisation of ATO to the 3' extended part of the modified target polynucleotide impossible.

In one embodiment, the first ATO reaction is a primer extension reaction, wherein the target polynucleotide serves as primer is extended on the ATO template by a DNA polymerase. The DNA polymerase may comprise a strand displacement activity or 5' to 3' exonuclease activity, wherein during the extension the stem-loop structure is opened or the upper ATO strand is displaced or digested. Any polymerase can be use, for example Klenow exo-, Bst polymerase, or T4 DNA polymerase.

In another embodiment, the first reaction is an extension-ligation reaction, wherein a DNA polymerase extends the target and a DNA ligase ligates the extended target sequence to the 5' stem portion of ATO or upper strand of ATO. Any DNA polymerase and DNA ligase can be used, for example, Klenow large fragment, T4 DNA ligase.

In another embodiment, the first reaction is a ligation reaction, wherein a DNA ligase ligates the target polynucleotide to the 5' stem portion of ATO or upper strand of ATO. Any DNA ligase can be used, for example T4 DNA ligase.

After the first reaction, the method may comprise digesting part of ATO or removing part of ATO by affinity capturing.

The method may comprise generating a modified first CS by using the first CS hybridising to the 3' random sequence of second ATO of any one of above mentioned ATO in an enzymatic reaction which adds an adaptor sequence to the 3' end of the first CS, wherein the second ATO comprises a different 5' universal sequence of the first ATO.

The method may further comprise generating a modified first CS by ligating double-stranded adaptors into the products of step (ii).

In the step following digestion/removal of ATO or without digestion/removal of ATO, generating a first complement sequence (CS) of the modified target polynucleotide is performed. The first complement sequence (CS) can be generated by primer extension. The primer can be a universal primer, capable of hybridising to the 3' extended part of the modified target polynucleotide and extending. Depending on the type of target polynucleotides which are either DNA, RNA, or a combination of RNA and DNA, the methods can utilize reverse transcription and/or primer extension by a DNA polymerase and/or reverse transcriptase. The primer extension reaction can be a single primer extension step. Alternatively, the primer extension reaction can be multiple cycles of linear amplification using the first primer. The generated first CS comprises 5' universal sequence and 3' complement sequence of the target polynucleotides. The first primer comprises 3' universal sequence identical or substantially identical to the universal sequence portion of ATO. The first primer may further comprise 5' another universal sequence portion, which is compatible to a sequencing platform. The first primer may further comprise a sample barcode sequence (SBC) between the 3' universal sequence and the 5' another universal portion.

In one embodiment, the method further comprises: generating a modified first CS using the first CS as primer and using a second adaptor template oligonucleotide (ATO) of any one of above-mentioned oligo as template. The 3' end of the first CS is extended on an ATO template to generate the extended first CS, which comprises a second universal sequence in the 3' end. following removal of second ATO, the first CS may be PCR amplified using two universal primers.

In another embodiment, the method further comprises: extending a second primer hybridized to the first CS or modified first CS, thereby forming a second CS, wherein the second primer comprises a target-specific portion or universal sequence, or both 3' target specific and 5' universal sequence. In one aspect, when second primer is a target specific primer, which may comprise a 3' target specific portion with or without a 5' universal portion. The extending using second primer may be one pass extension, or multiple cycles of linear amplification. Alternatively, the step (ii) and this step are combined into one single PCR reaction, which uses first primer to generate first CS and uses second primer to form second CS, where the first CS and second CS are generated simultaneously after first PCR cycle. After PCR reaction or linear amplification, the product may be purified, or primers are removed by single-strand specific nuclease digestion. If the first primer contains a sample barcode, the purified PCR products from multiple samples may be pooled together. The (pooled) purified PCR or linear amplification product is further PCR amplified using nested target-specific third primers for first CS and a universal primer for second CS. The nested target-specific third primers for first CS comprises 3' target specific portion and 5' universal sequence portion, wherein the 5' universal sequence portion is compatible to a NGS platform. The PCR product is then purified ready for sequencing. In another aspect, when second primer is a target specific primer, which may comprise a 3' target specific portion and a 5' universal portion, wherein the 5' universal portion is compatible with a NGS platform. The step (ii) and this step are combined into one single PCR reaction, which uses first primer to generate first CS and uses second primer to form second CS, where the first CS and second CS are generated simultaneously after first PCR cycle. The PCR product is then purified ready for sequencing.

When the original target polynucleotide in a sample is double stranded, the reaction of extending a second primer hybridized to the first CS may be divided into two separate reactions, forward reaction comprises a target-specific second primer complementary to forward strand of a target sequence, reverse reaction comprises a target-specific second primer complementary to reverse strand of the target sequence, wherein forward strand and reverse strand of the target sequence are complementary.

In the steps (i) or (ii), the extending may comprise one pass extension or linear amplification using first primer or second primer. In the step (ii), the extending may comprise exponential amplification using first primer and second primer.

The first primer may comprise a sample barcode (SBC) sequence and additional 5' universal sequence compatible for a NGS platform.

In one aspect, the disclosure provides a method of extending a target polynucleotide comprising: mixing the target polynucleotide with a polymerase enzyme, ATO molecule comprising NGS adaptor sequences and cleavable sequence; performing the trimming and extending reaction, heat inactivating the polymerase, followed by incubation with a single strand specific circularization ligase enzyme; optionally including a cleavage reaction or an amplification reaction with reverse and forward primers, either of which is performed to resolve the circular molecule into a completed linear NGS library molecule.

In another aspect, the method provides a method of extending a target polynucleotide comprising mixing the target polynucleotide with polymerase enzymes, ATO comprising the NGS adaptor sequence; performing the trimming and extending reaction, followed by incubation with a first primer complementary to the universal NGS adaptor sequence, a DNA polymerase and dNTPs to perform an extension reaction to generate CS and a double stranded substrate molecule; performing a ligation with T4 DNA ligase and a blunt-end or T-tailed adaptor which is formed by annealing two oligonucleotides comprising NGS adaptor sequence and a truncated complement and a 3' phosphate, wherein the one oligonucleotide is ligated to the 5' phosphate of the modified target polynucleotide molecule to complete a linear NGS library molecule.

The present disclosure further provides a method of accurately determining the sequence of a target polynucleotide comprising:
  (i) sequencing at least one of the amplified second CSs of any one of the above-mentioned methods;
  (ii) aligning at least two sequences containing the same UID from (i) and/or aligning same target sequences of two reactions, each reaction generates sequence information of one strand or complementary strand of a duplex target sequence; and
  (iii) determining a consensus sequence and/or identical variant sequence of two reactions based on (ii), wherein the consensus sequence and/or variant sequence accurately represents the target polynucleotide sequence.

The present disclosure further provides a kit for generating a library of polynucleotides comprising an adaptor template oligonucleotide (ATO) of any one of the above-mentioned ATO, and primers compatible to a NGS platform.

A kit comprises the composition described above.

A kit for generating a library of polynucleotides comprises an adaptor template oligonucleotide (ATO) described above, polymerase and primers compatible to NGS platform.

A target polynucleotide is a polynucleotide, modified polynucleotide or combination thereof as described herein below. The target polynucleotide is, in various embodiments, DNA, RNA, or a combination thereof. In another embodiment, the target polynucleotide is chemically treated nucleic acid, including but not limited to embodiments wherein the substrate polynucleotide is bisulfite-treated DNA to detect methylation status by NGS.

The target polynucleotides are obtained from naturally occurring sources or they can be synthetic. The naturally occurring sources are RNA and/or genomic DNA from a prokaryote or a eukaryote. For example and without limitation, the source can be a human, mouse, virus, plant or bacteria. In various aspects, the target polynucleotide is extended at the 3' end with an adaptor sequence for use in assays involving microarrays and creating libraries for next generation nucleic acid sequencing.

If the source of the target polynucleotide is genomic DNA or RNA or both, in some embodiments the genomic DNA or RNA or both is fragmented prior to its being extended. Fragmenting of genomic DNA/RNA is a general procedure known to those of skill in the art and is performed, for example and without limitation in vitro by shearing (nebulizing) the DNA/RNA, cleaving the DNA/RNA with an endonuclease, sonicating the DNA/RNA, by heating the DNA/RNA, by irradiation of DNA/RNA using alpha, beta, gamma or other radioactive sources, by light, by chemical cleavage of DNA/RNA in the presence of metal ions, by radical cleavage and combinations thereof. Fragmenting of genomic DNA/RNA can also occur in vivo, for example and without limitation due to apoptosis, radiation and/or exposure to asbestos. According to the methods provided herein, a population of target polynucleotides are not required to be of a uniform size. Thus, the methods of the disclosure are effective for use with a population of differently-sized target polynucleotide fragments.

As used herein, a "target polynucleotide complement sequence (CS)" is a polynucleotide comprising a sequence complementary to a target sequence or a complement thereof (complement of a sequence complementary to a target sequence). In some embodiments, a target polynucleotide complement sequence comprises a first complement sequence. A "first complement sequence" is a polynucleotide reverse transcribed from a target polynucleotide or formed from a primer extension reaction on a target polynucleotide or RNA polynucleotide transcribed from a double-stranded RNA polymerase promotor from the modified target polynucleotide by a RNA polymerase. A modified target polynucleotide is a target polynucleotide extended on ATO comprising random sequence and universal sequence.

A target polynucleotide complement sequence comprises a second complement sequence. A "second complement sequence" is a polynucleotide comprising a sequence complementary to a first complement sequence. A target polynucleotide complement sequence may comprise a UID. For example, a first complement sequence may comprise a UID which is provided by a random sequence of ATO and by the 3' end part of the randomly fragmented target polynucleotide.

The second or third primer may be a set of a plurality of second or third primers. Each second or third primer of a plurality of second or third primers is extended simultaneously, is extended in the same reaction chamber.

The amplification step using target specific second primers may be divided into two reactions: forward reaction and reverse reaction. The forward reaction comprises forward set of multiple target specific second primers annealing to first strands of the multiple target CS from one sample, and the reverse reaction comprises a reverse set of multiple target specific second primers annealing to the second strands of the multiple target CS from the same sample. The primers used to generate PCR products in the nested PCR may comprise a universal primer targeting the 5' universal sequence portion of the first primers and a third set of multiple target specific primers annealing to second strands of the multiple target sequences, wherein the third set of the target-specific primers (inner primers) is nested to the set of the target-specific second primers (outer primers). The universal primers in the forward and reverse reactions may be the same.

The reaction mixtures may comprise multiple reactions for more than one sample, which may be two samples, three samples, or more than three samples, or more than 10 samples. Different samples may be process together in parallel. Each sample may comprise two reactions: forward reaction and reverse reaction. Different sample reactions (all forward reactions, or all reverse reactions) may be preferably mixed after step (ii), where the identity of each sample is assigned in the amplification by first primers having SBC. All forward reactions or reverse reactions after step (ii) may be processed in one mixture.

The method further comprises analysing the NGS reads derived from the forward reaction and the reverse reaction, which represent two different strands of target sequences, comprising generating an error-corrected consensus sequences by (i) grouping into families containing the same random sequence identifier (UID) sequences; (ii) removing the target sequences of the same family having one or more nucleotide positions where the target sequence disagree with majority members, and (iii) examining if the same mutations appearing in the two reactions, which represent different strands of a target sequence.

The method further comprises analysing the NGS reads derived from the forward reaction and the reverse reaction, which represent two different strands of target sequences, comprising generating consensus sequences by grouping into families containing the same random sequence identifier (UID) sequences; and counting the numbers of families. This method provides an accurate counting for the numbers of original target nucleic acids present in a sample.

The methods can be used to quantitate the starting molecules, the counting of UID families of a target sequence in comparison with other samples or comparing between forward reaction and reverse reaction may provide accurate counting information.

The purpose of UID is twofold. First is the assignment of a unique UID to each original DNA or RNA template molecule. The second is the amplification of each uniquely tagged template, so that many daughter molecules with the identical UID sequence are generated (defined as a UID family). If a mutation pre-existed in the template molecule used for amplification, that mutation should be present in every daughter molecule containing that UID.

The universal primers may contain one, or two, or more terminal phosphorothioates to make them resistant to any exonuclease activity. They may also contain 5' grafting sequences necessary for hybridization to NGS flow cell, for example the Illumina GA IIx flow cell. Finally, they may contain an index sequence between the grafting sequence and the universal tag sequence. This index sequence enables the PCR products from multiple different individuals to be simultaneously analysed in the same flow cell compartment of the sequencer.

The target nucleic acid sequence of a sample may comprise a nucleic acid fragment or gene which contains variant nucleotide(s) and may be selected from the group consisting of disorder-associated SNP(s)/deletion(s)/insertion(s), chromosome rearrangement(s), trisomy, or cancer gene(s), drug-resistance gene(s), and virulence gene(s). The disorder-associated gene may include but is not limited to cancer-associated genes and genes associated with a hereditary disease. The sample may be genomic DNA, circulating nucleic acid, RNA, mRNA, small RNA, micro RNA, or FFPE DNA or RNA.

The variant nucleotide(s) in the diagnostic region of the target polynucleotide sequence may include one or more nucleotide substitutions, chromosome rearrangement, deletions, insertions and/or abnormal methylation.

DNA methylation is an important epigenetic modification of the genome. Abnormal DNA methylation may result in silencing of tumour suppressor genes and is common in a variety of human cancer cells. In order to detect the presence of any abnormal methylation in the target polynucleotide, a preliminary treatment should be conducted prior to the practice of the present method. Preferably, the nucleic acid sample should be chemically modified by a bisulphite treatment, which will convert cytosine to uracil but not the methylated cytosine (i.e., 5-methylcytosine, which is resistant to this treatment and remains as cytosine). With these modifications, the method can be applied to the detection of abnormal methylation(s) in the target nucleic acid. In another embodiment the modification by bisulphite treatment occurs after the ATO reaction. In another embodiment the modification by bisulphite treatment occurs after the generation of the first CS.

The present disclosure provides a method of analysing a biological sample for the presence and/or the amount and/or frequency of mutations or polymorphisms at multiple loci of different target nucleic acid sequences. In another aspect, the present disclosure provides a method of analysing a biological sample for chromosomes abnormality of, for example trisomy. The ATO reaction may be followed by next generation sequencing, digital PCR, microarray, or other high throughput analysis. The number of multiplexing of target loci may be more than 5, or more than 10, or more than 30, or more than 50, or more than 100, or more than 500, more than 1000, even more than 2000.

When a mutant is in very low concentration in a sample, for example one or two mutants are present in the sample, after dividing the sample nucleic acid into two reactions, only one reaction may contain the mutant. The comparison of two strands sequences from the two reactions may reveal that only one reaction may contain mutation. It will be classified as the true mutation if more than one read families contain the same mutation, even when the mutation appears in only one reaction.

In another embodiment the modified target polynucleotide can be amplified by linear or exponential amplification prior to dividing the sample nucleic acid into two reactions, for one or more subsequent rounds of amplification. Due to the increase in the copy number of all original molecules, the comparison of two strands sequences from the two reactions are more likely to reveal the presence of a mutation.

In another embodiment the modified target polynucleotide is not divided into two reactions and only one of the two strands is probed for the presence of the mutation.

In another embodiment the target polynucleotide is not divided into two reactions, and both strands are separately and sequentially amplified to allow analysis of both strands.

The release of cell-free DNA into the bloodstream from dying tumour cells has been well documented in patients with various types of cancer. Research has shown that circulating tumour DNA can be used as a non-invasive biomarker to detect the presence of malignancy, follow treatment response, or monitor for recurrence. However, current methods of detection have significant limitations. Next Generation Sequencing (NGS) methods have revolutionised genomic exploration by allowing simultaneous sequencing of hundreds of billions of base pairs at a small fraction of the time and cost of traditional methods. However, the error rate of ~1% results in hundreds of millions of sequencing mistakes, which is unacceptable when aiming to identify rare mutants in genetically heterogeneous mixtures, such as tumours and plasma. The methods of this invention overcome these limitations in sequencing accuracy. Mutation-harbouring cfDNA can be obscured by a relative excess of background wild-type DNA; detection has proven to be challenging. The method greatly reduces errors by independently tagging and sequencing each original DNA duplex.

The methods of the present invention can substantially improve the accuracy of massively parallel sequencing. The approach can easily be used to identify rare mutants in a population of DNA templates. The two strands of one target template in sample, each is uniquely tagged and independently sequenced. Comparing the sequences of the two strands results in either agreement to each other or disagreement. The agreement gives the confidence to score a mutation as true positive.

After sequencing, members of each read family are identified and grouped by virtue of sharing the identical UID tag sequence. The sequences of uniquely UID tagged family and one or two strands of target sequences are then compared to create a consensus sequence. This step filters out random errors introduced during sequencing or PCR to yield a set of sequences, each of which derives from an individual molecule of single-stranded DNA.

In addition to their application for high sensitivity detection of rare DNA variants, the barcoded random sequence identifier in the target specific primer can also be used for single-molecule counting to precisely determine relative or absolute DNA and/or RNA copy numbers. Because tagging occurs before major amplification, the relative abundance of variants in a population can be accurately assessed given that proportional representation is not subject to skewing by amplification biases.

The methods of the present invention greatly reduce errors by tagging each target sequence with random sequence identifier and sequencing the two strands. Analysis provides error-corrected consensus sequences by grouping the sequenced uniquely tagged sequences; removing the target sequences of the same family having one or more nucleotide positions where the target sequence disagrees with majority members in a family; and same mutations appearing in the two populations would be the true mutations.

The method can be used for detecting mutation in any sample such as FFPE or blood. The accurate counting of sequencing reads which reflect the original molecules present in a sample provides information for copy number variations or for prenatal test for chromosome abnormality.

Reagents employed in the methods of the invention can be packaged into kits. Kits include ATO(s), polymerase(s), the primer(s), in separate containers or in a single master mixture container. The kit may also contain other suitably packaged reagents and materials needed for extension, amplification, enrichment, for example, buffers, dNTPs, and/or polymerizing means; and for detection analysis, for example, and enzymes, as well as instructions for conducting the assay.

Figure 1A:
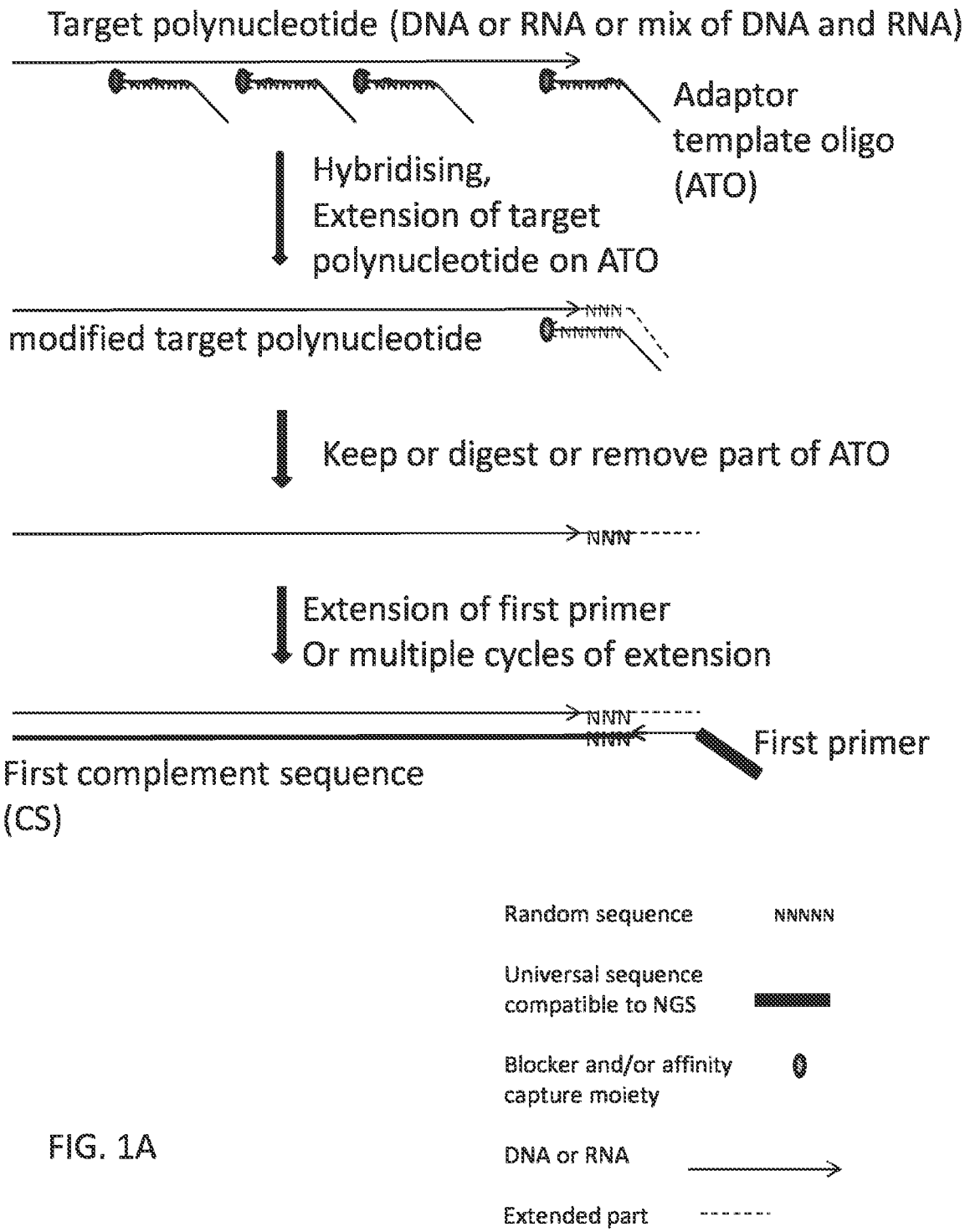
FIG. 1A depicts a schematic of an illustrative embodiment. A target polynucleotide (PCR product(s), or DNA, or RNA, or any mixture thereof) may be double-stranded, only one of two strands is shown (forward strand). In the step (i), ATO molecules are hybridised to single-stranded target polynucleotide sequences at one or more locations. The 3' ends of the target polynucleotide hybridises to the 3' random sequence portion of ATO, is trimmed if any 3' overhang is present, and is extended using ATO as template. The extension generates a modified target polynucleotide, which comprises a random sequence as UID and a 3' universal sequence as priming site. Following step (i), the ATOs are digested or removed by affinity capture. In some embodiment, the ATO is not digested or removed. In the step (ii) the first universal primers are added to hybridise to the modified target polynucleotide and are extended to generate first complement sequences (CS).
Figure 1B:
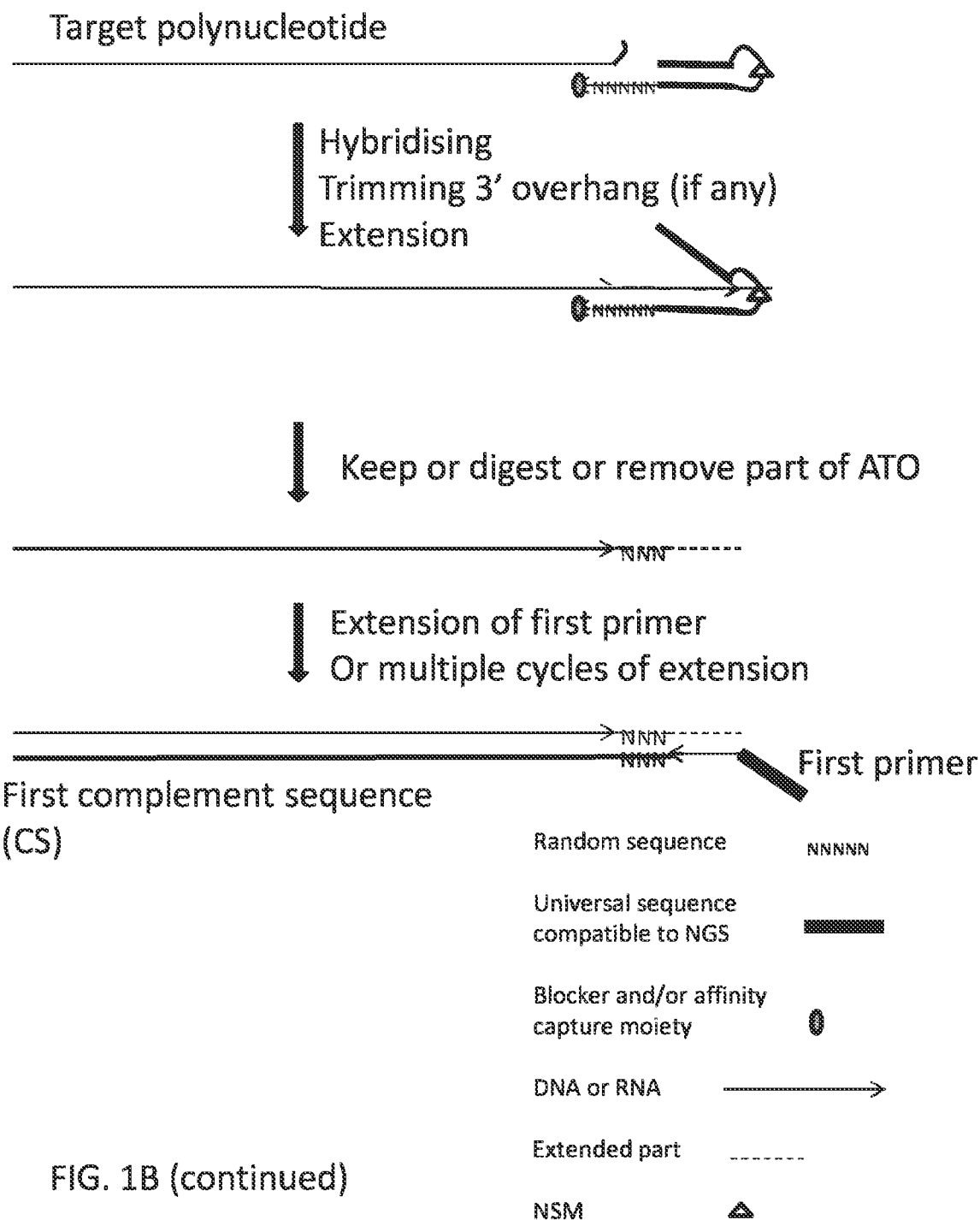
FIG. 1B depicts a schematic of an illustrative embodiment. In the step (i), ATO are hybridised to a single-stranded target polynucleotide sequences at one or more locations. The 3' ends of the target polynucleotide hybridises to the 3' random sequence portion of ATO, is trimmed if any 3' overhang is present, and is extended using ATO as template. The ATO comprises a stem-loop structure and the loop portion comprises a non-copiable linkage. The extension displaces the 5' stem portion sequence and stops at the non-copiable linkage. The extension generates a modified target polynucleotide, which comprises a random sequence as UID and a 3' universal sequence as priming site. Following step (i), the ATOs are digested, or removed by affinity capture. In some embodiment, the ATO is not digested or removed. In the step (ii) the first universal primers are added to hybridise to the modified target polynucleotide and are extended to generate first complement sequences (CS).
Figure 1C:
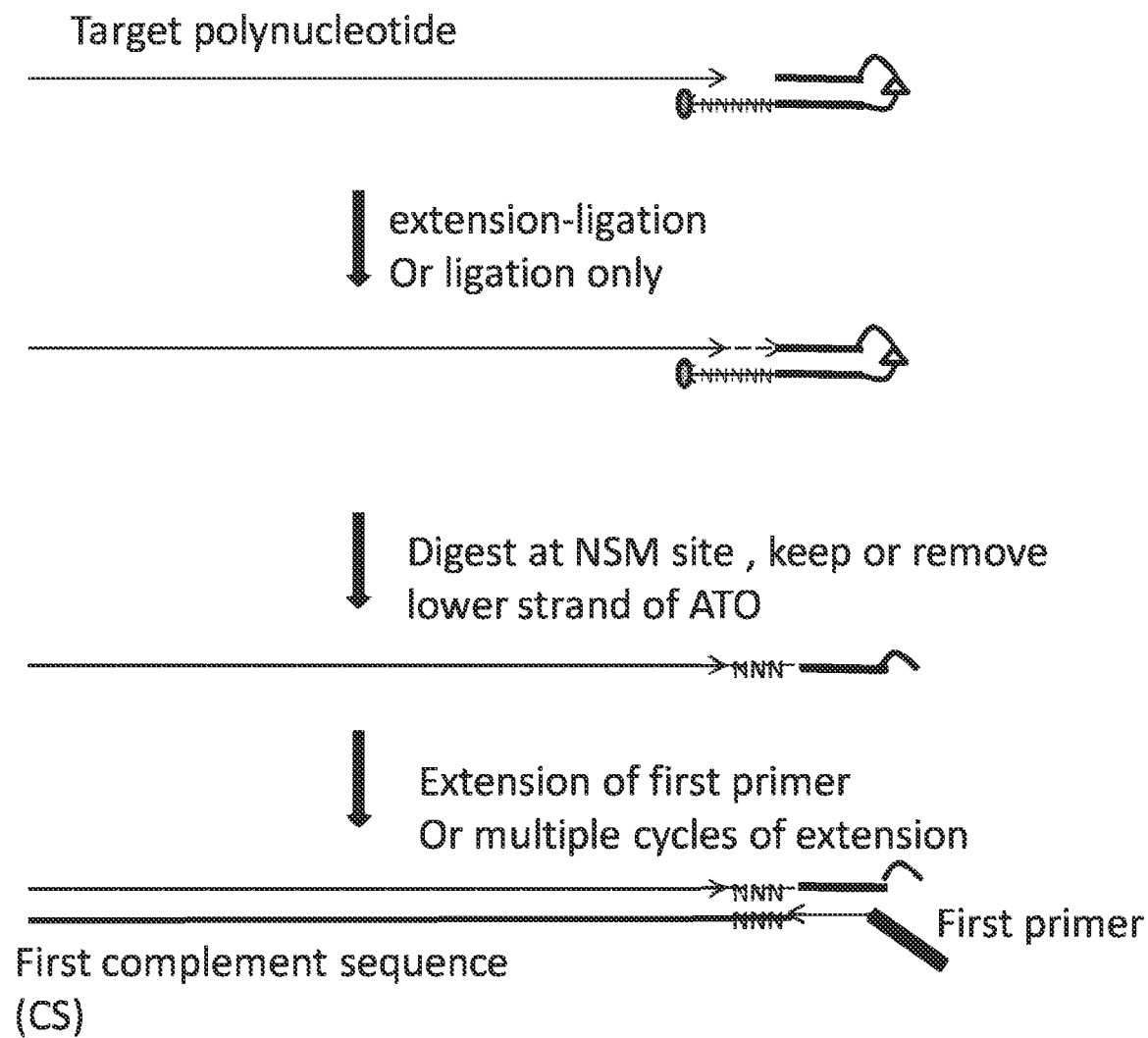
FIG. 1C depicts a schematic of an illustrative embodiment. In the step (i), ATO are hybridised to a single-stranded target polynucleotide sequences at one or more locations. The 3' ends of the target polynucleotide hybridises to the 3' random sequence portion of ATO, is trimmed if any 3' overhang is present, and is extended using ATO as template. The ATO comprises a stem-loop structure and the loop portion comprise modification which can be digested or cleaved, such as uracil nucleotide, allowing for breaking the hairpin. The extension strand meets the 5' stem portion sequence, and is ligated to the 5' stem portion which contains 5' phosphate group. The extension-ligation generate a modified target polynucleotide, which comprises a random sequence as UID and a 3' universal sequence as priming site. In some embodiments, the 3' end of one strand of the target polynucleotide hybridises to the 3' random sequence portion of ATO immediately adjacent to the 5' stem portion of the ATO and is ligated to the 5' stem portion of the ATO by a DNA ligation. This ligation can occur without using DNA polymerase. After step (i), the ATOs may be cleaved at the modification, the lower part of ATO may be digested or removed by affinity capture. In the step (ii) the first universal primers are added to hybridise to the modified target polynucleotide and are extended to generate first complement sequences (CS).
Figure 1D:
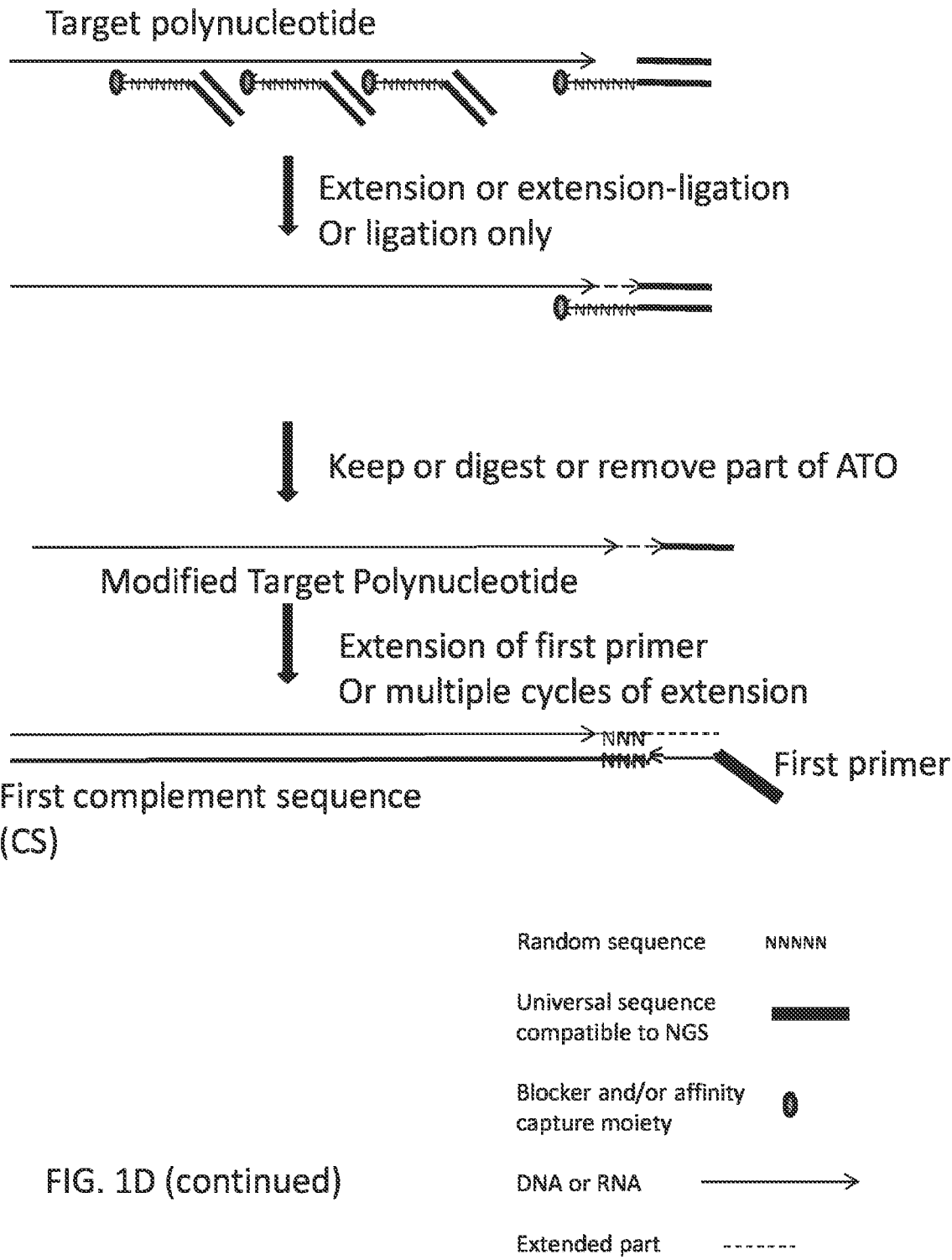
FIG. 1D depicts a schematic of an illustrative embodiment. In the step (i) of reaction, ATO are hybridised to a single-stranded target polynucleotide sequences at one or more locations. The 3' end of one strand of the target polynucleotide hybridises to the 3' random sequence portion of ATO, is trimmed if any 3' overhang is present, and is extended using ATO as template. The ATO comprises a double-stranded structure, the universal portion of the ATO is formed with two sequences designed to anneal to form a double strand region, a lower part of ATO containing the random sequence, and separated upper part. The extension of the target nucleotide displaces or digests the upper part sequence by a DNA polymerase with a strand displacement activity or 5' to 3' exonuclease activity. The extension generates a modified target polynucleotide, which comprises a random sequence as UID, and a 3' universal sequence as a priming site. The ATO may be digested after the first reaction. In some embodiment, the 3' end of one strand of the target polynucleotide hybridises to the 3' random sequence portion of ATO, is trimmed if any 3' overhang is present, and is extended using ATO as template. The extension strand meets the 5' upper part sequence and is ligated to the 5' upper part which contains 5' phosphate group. The extension-ligation generates a modified target polynucleotide, which comprises a random sequence as UID, and a 3' universal sequence as a priming site. In some embodiment, the 3' end of one strand of the target polynucleotide hybridises to the 3' random sequence portion of ATO immediately adjacent to the 5' end of the upper part of the ATO and is ligated to the 5' upper part of the ATO by a DNA ligase. This ligation can occur without using DNA polymerase. After step (i), the ATOs or lower part of ATO may be removed by digestion or affinity capture. In the step (ii) the first universal primers are added to hybridise to the modified target polynucleotide and are extended to generate first complement sequences (CS).
Figure 2:
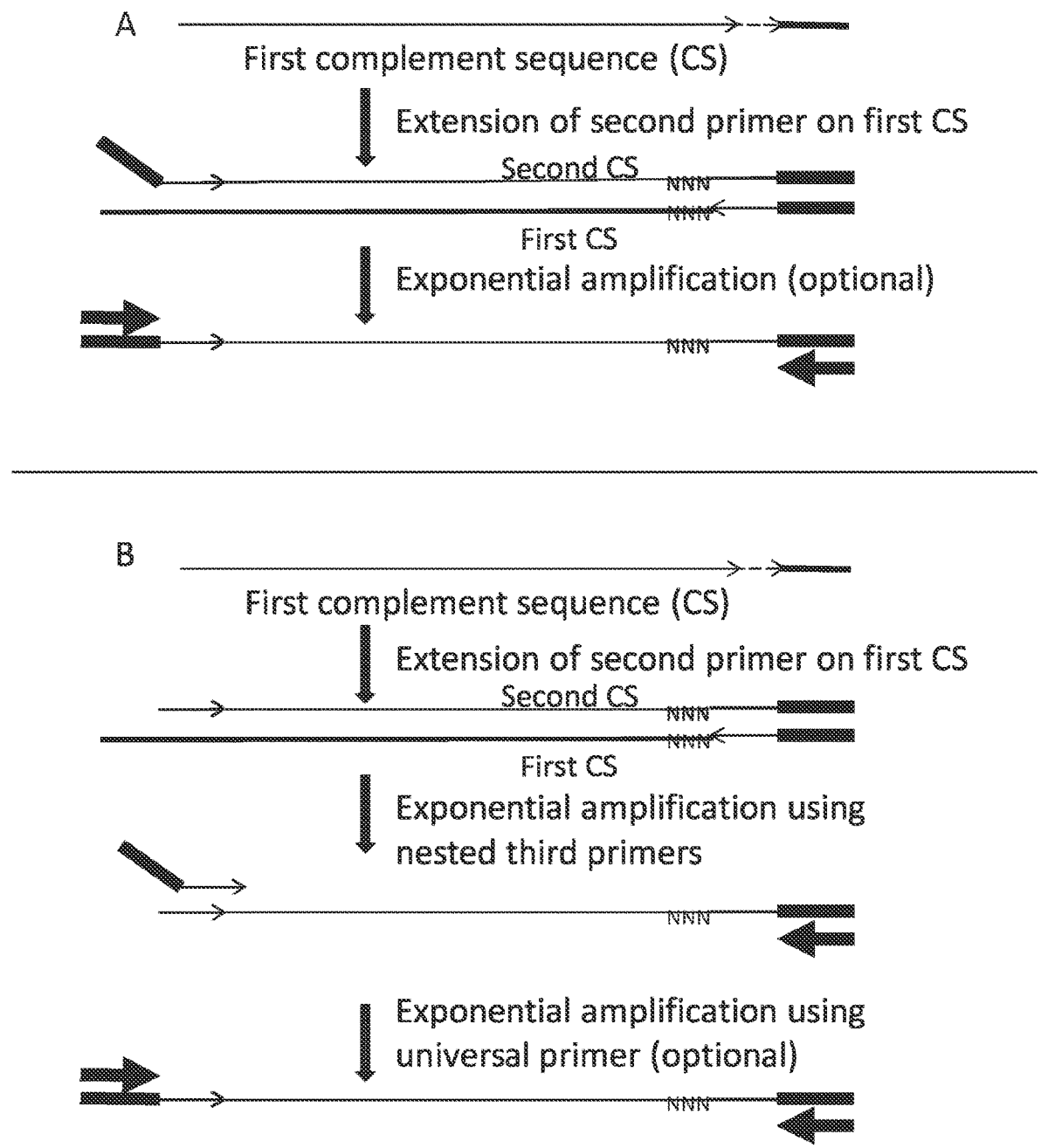
FIG. 2 depicts a schematic of an illustrative embodiment.
Figure 2:
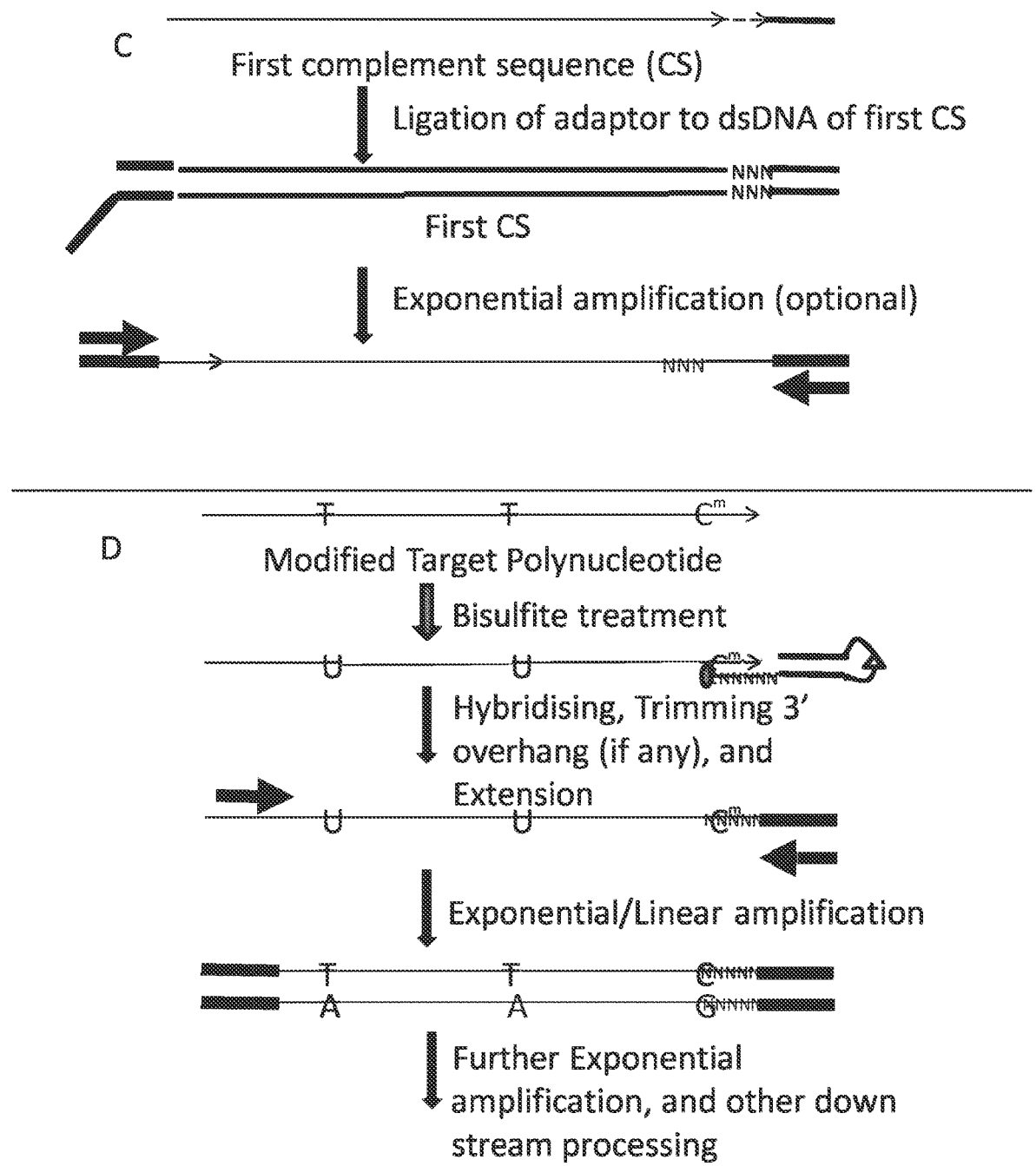
Figure 2:
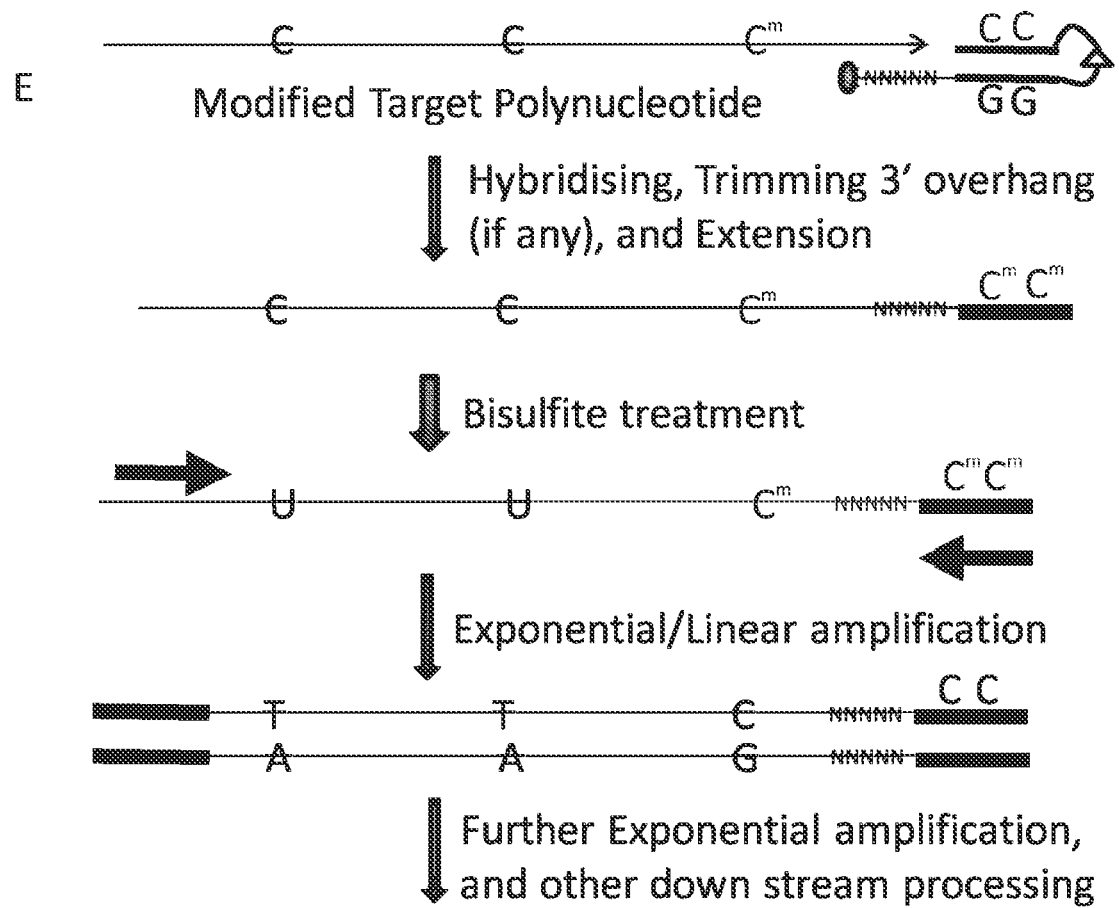
Figure 2:
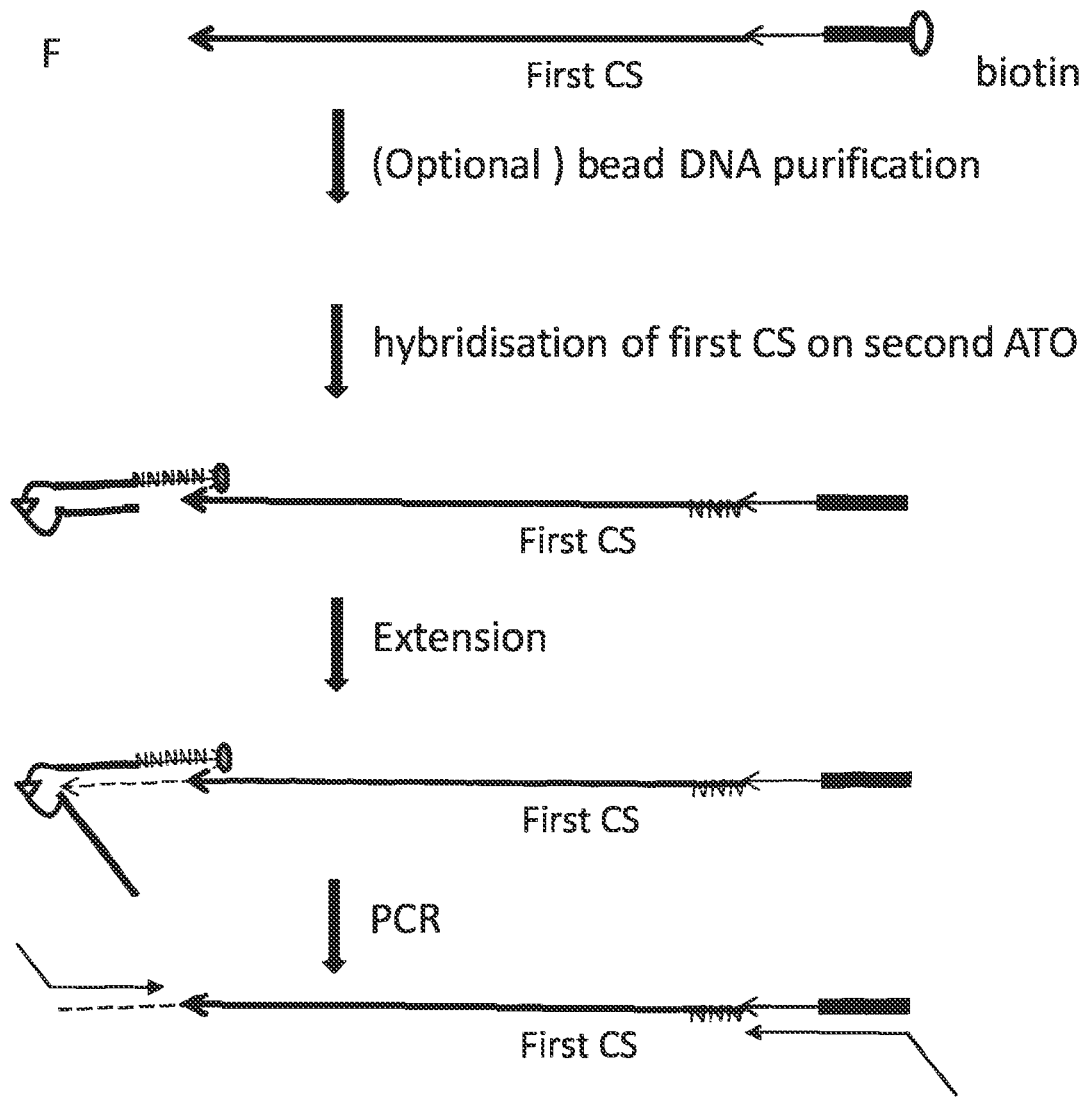
Figure 2:
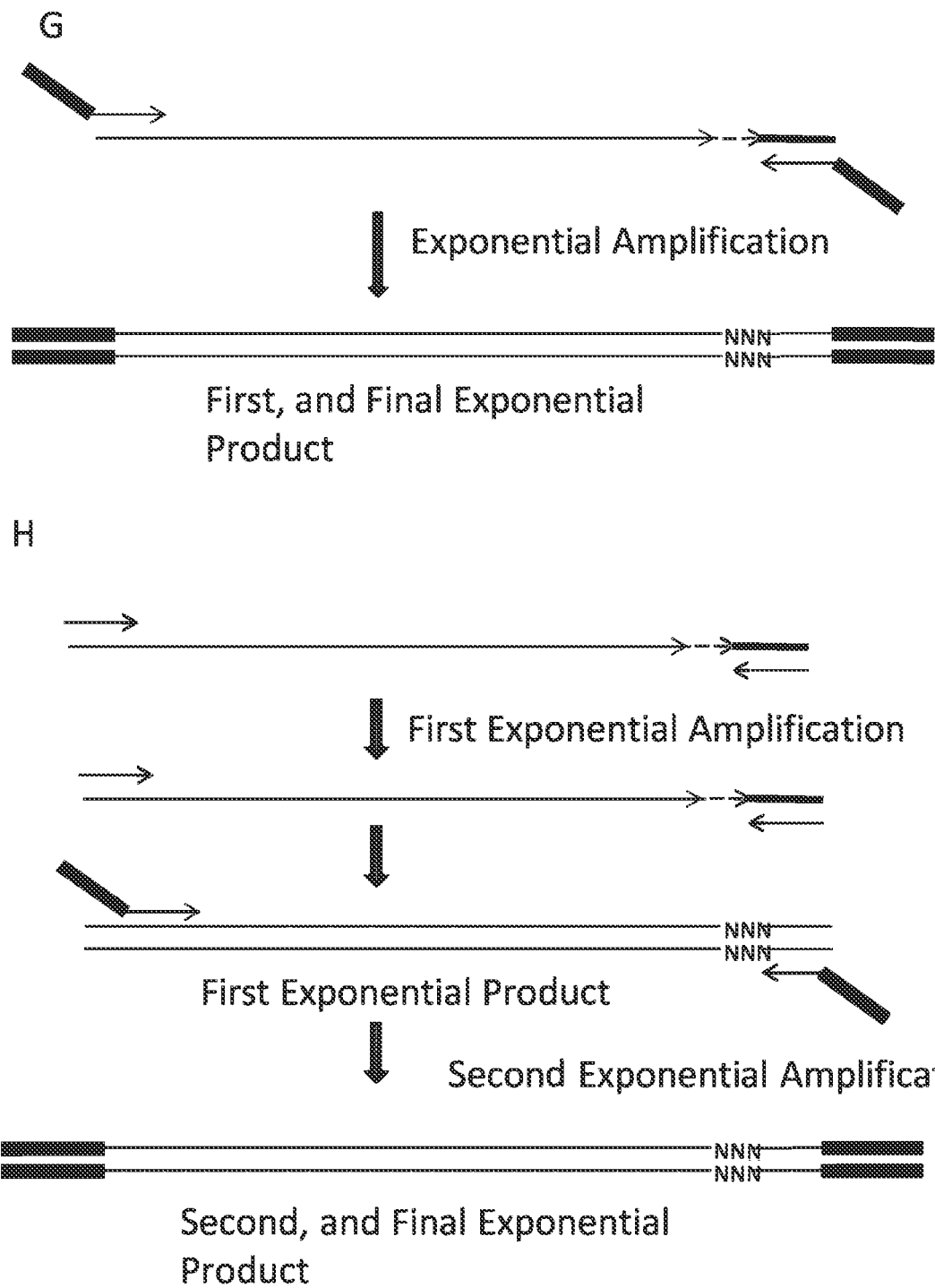

(A) Target specific second primers are provided to hybridise the first CS and are extended to generate a second CS. The target specific second primer comprises a 3' target specific portion and a 5' universal portion. The extending can be one pass extension, or multiple cycles of linear amplification, or PCR amplification using both first primer and second primer. Optionally, the second CS may be further PCR amplified using universal primers compatible for NGS platform.

(B) Target specific second primers are provided to hybridise the first CS and are extended to generate a second CS. The target specific second primer comprises a 3' target specific portion with or without 5' universal portion. The extending can be one pass extension, or multiple cycles of linear amplification, or PCR amplification using both first primer and second primer. The second CS is further PCR amplified using nested target specific third primers and universal primers compatible for NGS platform. Optionally, the second CS may be further PCR amplified using universal primers compatible for NGS platform.

(C) the first primer annealing to the added adaptor sequence of the target polynucleotide and is extended to generate a double-stranded DNA of first CS. Double-stranded DNA of first CS is ligated to an adaptor through double-strand ligation by a DNA ligase. Only the CS strand needs to be ligated. The ligation product can be optionally affinity captured to a solid support. After ligation, the production can be amplified by two universal primers.

(D) the target polynucleotide is bisulfite treated, which converts unmethylated cytosine (C) to uracil and leaves methylated cytosine intact. ATO are hybridised to single-stranded target polynucleotide sequences at one or more locations. The 3' end of one strand of the target polynucleotide hybridises to the 3' random sequence portion of ATO, is trimmed if any 3' overhang is present, and is extended using ATO as template. The extension generates a modified target polynucleotide, which comprises a random sequence as UID, and a 3' universal sequence as a priming site. The ATO may be digested after the first reaction. The modified target polynucleotide hybridises with a universal primer, the 3' of this primer is designed to hybridise to the universal sequence of the modifier target polynucleotide with or without an additional 5' universal sequence, and a pool or one or target specific primers, which comprise a 3' target specific portion with or without an additional 5' universal portion. The two mix is the amplified with one or more cycles of PCR amplification using both the universal primer and a target specific primer(s). The product of this amplification can directly be used for next generation sequencing, or can be further processed resulting in a product suitable for next generation sequencing.

(E) ATO are hybridised to single-stranded target polynucleotide sequences at one or more locations. The 3' end of one strand of the target polynucleotide hybridises to the 3' random sequence portion of ATO, is trimmed if any 3' overhang is present, and is extended using ATO as template. The extension generates a modified target polynucleotide, which comprises a random sequence as UID, and a 3' universal sequence as a priming site. The ATO may be digested after the first reaction. The modified target polynucleotide subsequently undergoes bisulphate treatment. The modified target polynucleotide hybridises with a universal primer, the 3' of this primer is designed to hybridise to the universal sequence of the modifier target polynucleotide with or without an additional 5' universal sequence, and a pool or one or target specific primers, which comprise a 3' target specific portion with or without an additional 5' universal portion. The two mix is the amplified with one or more cycles of PCR amplification using both the universal primer and a target specific primer(s). The product of this amplification can directly be used for next generation sequencing, or can be further processed resulting in a product suitable for next generation sequencing.

(F) The first CS is hybridised to a second ATO and generates a modified first CS with adaptor sequence added to the 3' end of the first CS. The first CS may be generated by linear amplification using a first primer comprising a biotin. Optionally following the linear amplification, the first CS is affinity captured by avidin, and the non-first CS is removed by washing. The second ATO is added and the extension reaction was repeated as the first reaction. Following the extension reaction, the non-reacted product was washed away, and the product is amplified by two universal primers targeting both ends of universal sequence. The universal primer targeting to the 5' end of the first CS can be a nest primer.

(G) The modified target polynucleotide is divided into one or more aliquots, each aliquot is combined with a universal primer, the 3' portion of this primer is designed to hybridise to the universal sequence of the modifier target polynucleotide and has a 5' tail containing sequences necessary for next generation sequencing, a different target specific primer or pool of target specific primers is added, the primers are designed to amplify target regions of the target polynucleotide. The target specific primers comprise a 3' target specific portion with a 5' universal portion containing sequences necessary for next generation sequencing. The mix is amplified with one or more cycles of PCR amplification using both the universal primer and target specific primer(s). The product of this amplification will be PCR products each of which has amplified target regions of the original polynucleotide, and will include all necessary sequences for compatibility with next generation sequencing.

(H) The modified target polynucleotide is combined with a universal primer, the primer is designed to hybridise to the universal sequence of the modifier target polynucleotide, with or without an additional 5' universal sequence, a target specific primer or pool of target specific primers is added. The target specific primers comprise a 3' target specific sequence with or without a 5' universal sequence. The mix is amplified with one or more cycles of PCR amplification using both the universal primer and target specific primer(s). The product of this amplification will be PCR fragments which have amplified target regions of the original polynucleotide, with or without '3 and 5' universal sequences. The first amplification product may be purified to remove no longer necessary reagents from the first PCR reaction. The PCR products are combined with a second, nested universal primer, the 3' portion of this primer is designed to hybridise to universal sequence of the first PCR product and has a 5' tail containing sequences necessary for next generation sequencing, and a different nested target specific primer or pool of nested target specific primers which comprise a 3' target specific portion with a 5' universal portion containing sequences necessary for next generation sequencing. The mix is amplified with one or more cycles of PCR amplification using both the universal primer and target specific primer(s). The product of this amplification is PCR products which have amplified target region of the original polynucleotide, and will include all necessary sequences for compatibility with next generation sequencing.

Figure 3:
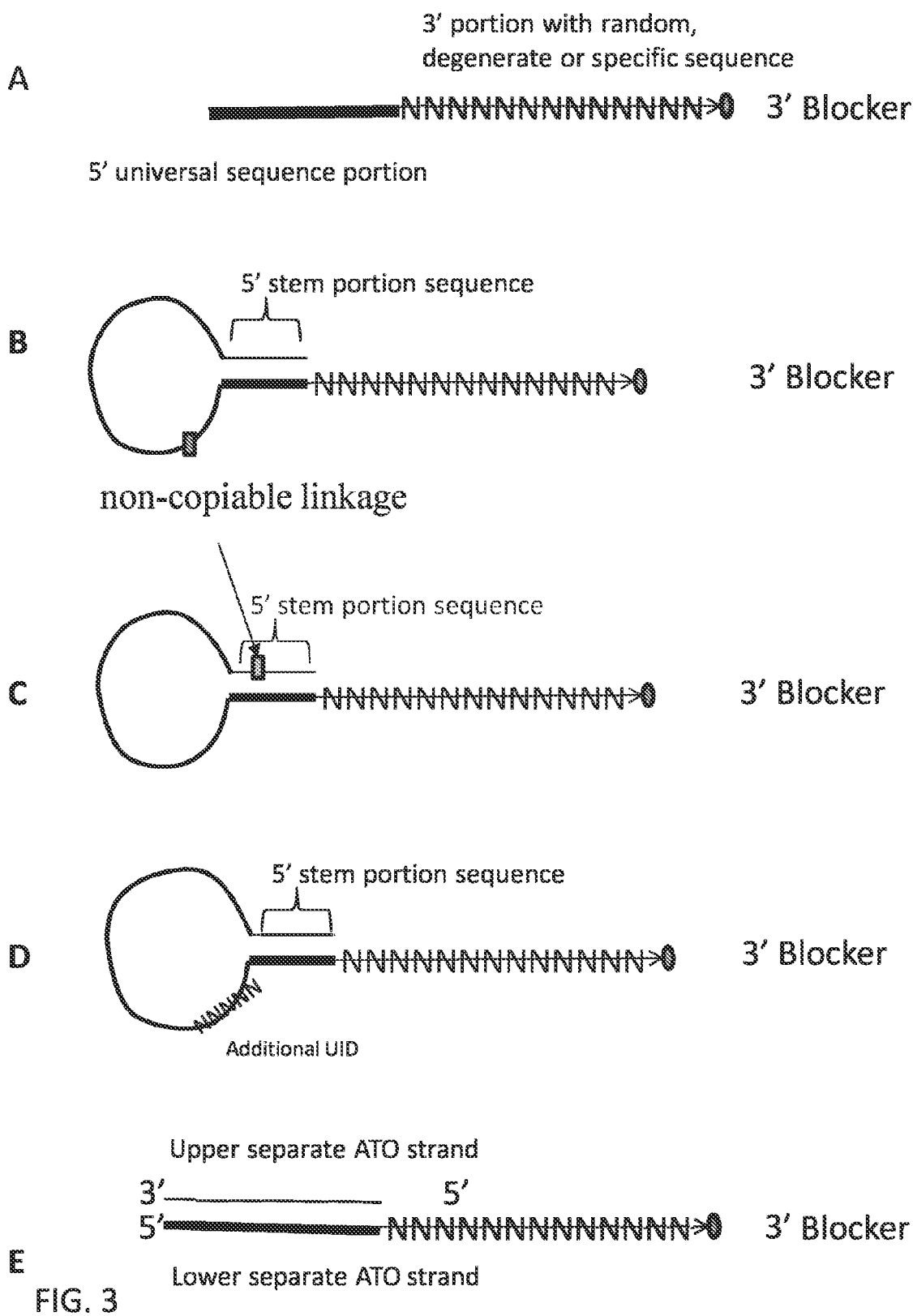
Figure 3:
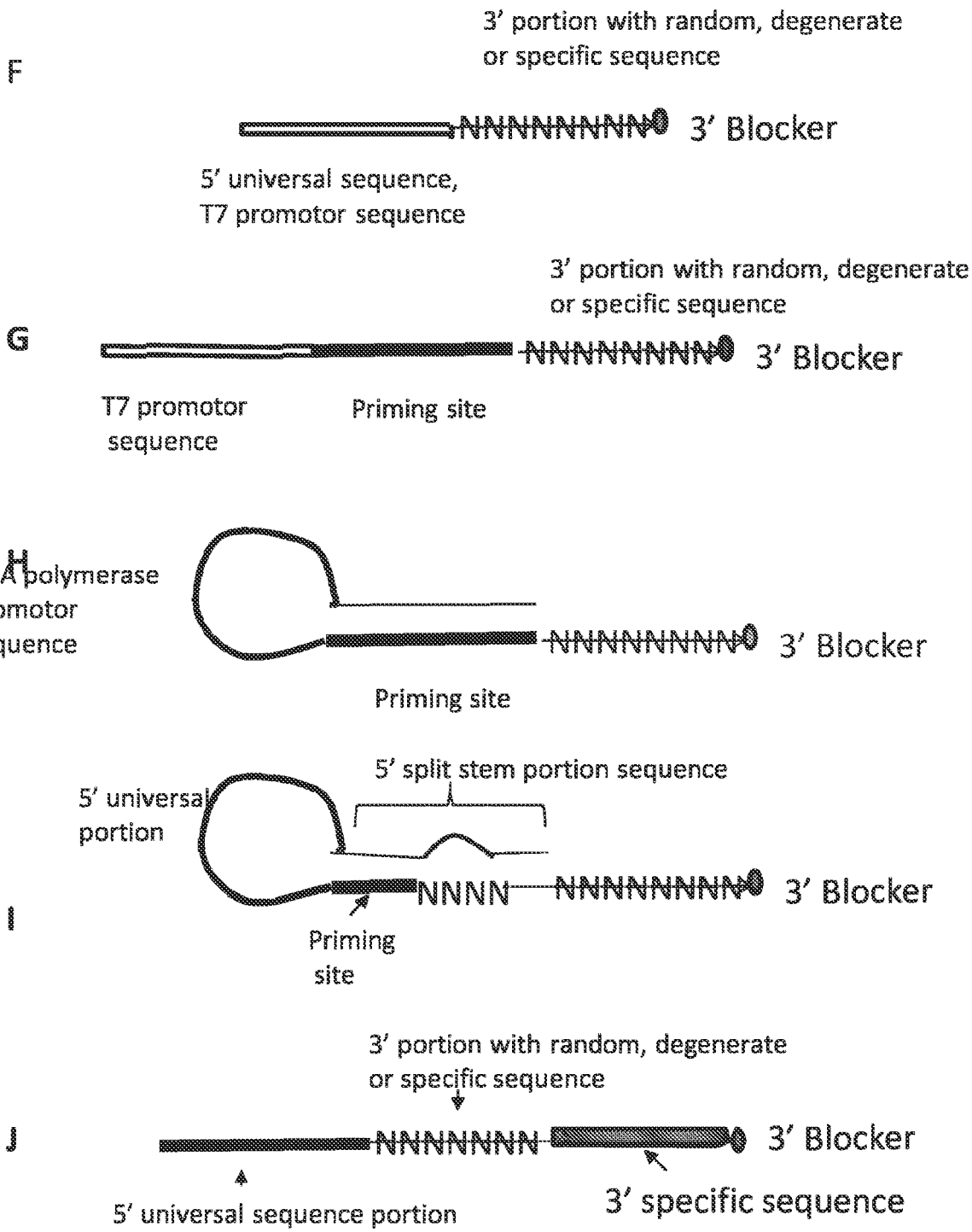
Figure 3:
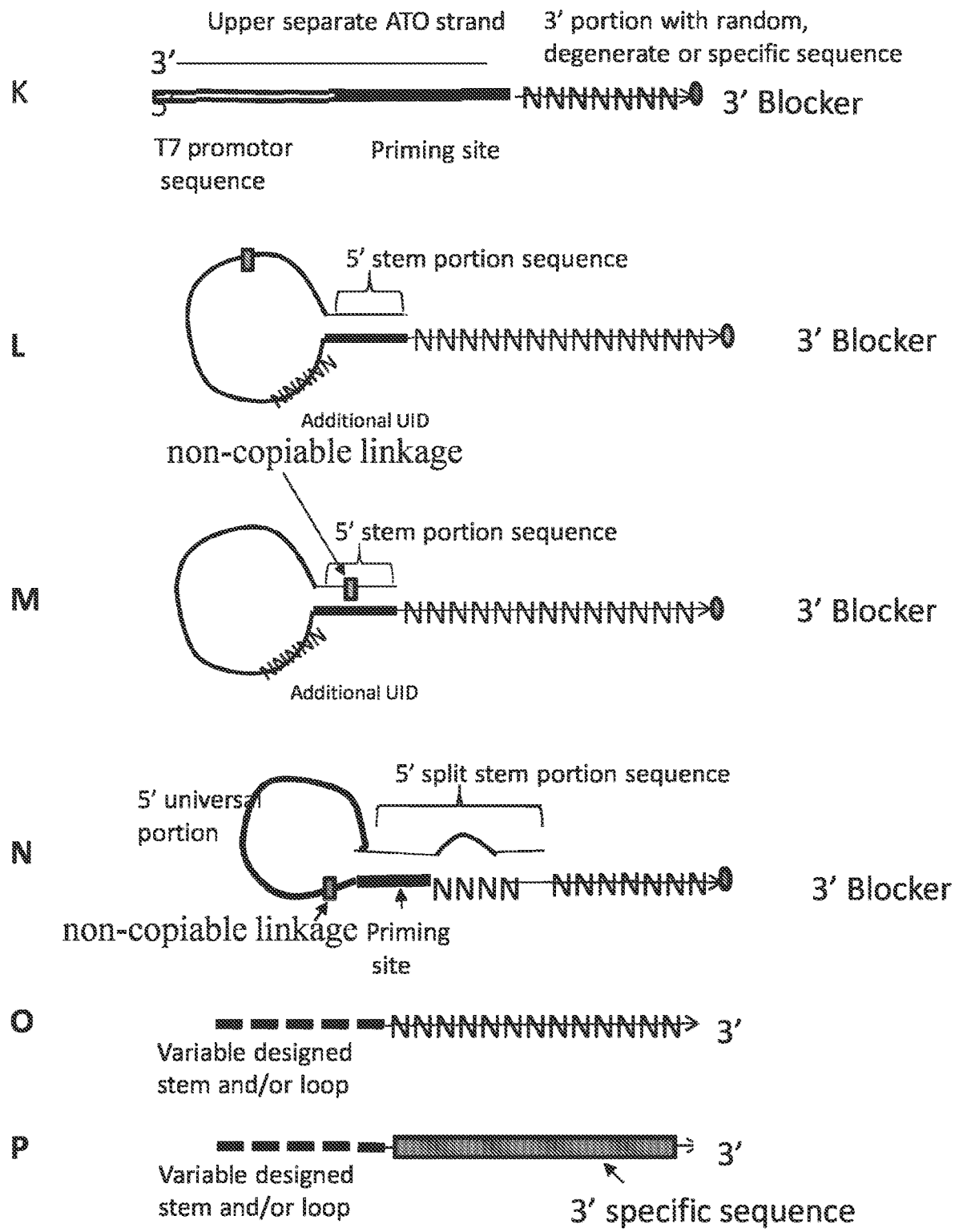
Figure 3:
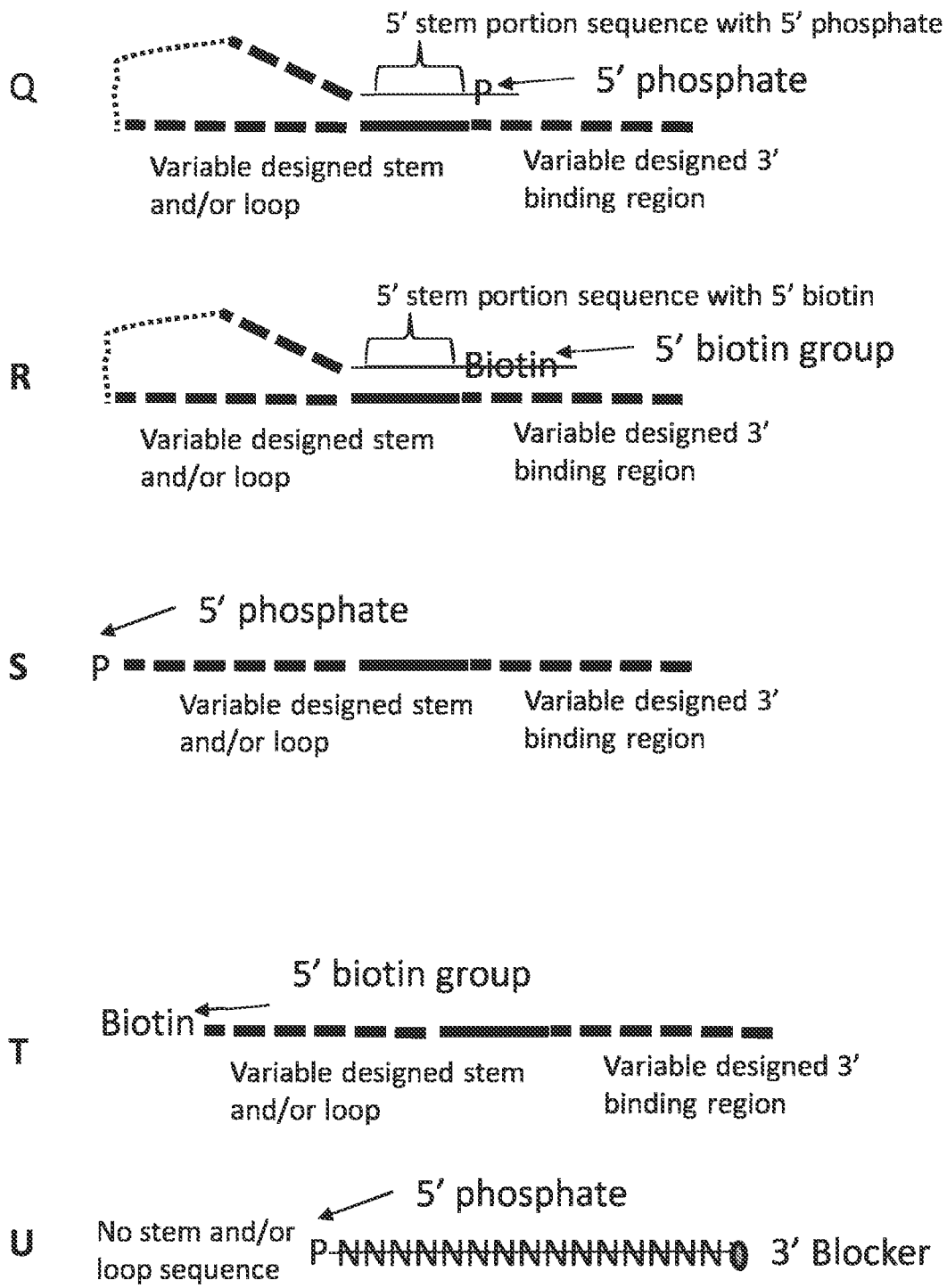

FIG. 3 depicts a schematic of an illustrative embodiment. Adaptor template oligos include (A) in addition to any combination of design components mentioned in (A-T) an ATO which comprises a 3' random sequence, a degenerate sequence, a random sequence with nucleotide bias, or a target specific sequence; the very 3' end is attached with a blocker moiety, which makes ATO unextendable; a universal sequence, 5' to the random sequence; and moiety(s) which can be nucleotide sequence/modification (NSM) recognisable by an agent.

(B) in addition to any combination of design components mentioned in (A-T) an ATO which comprises a hairpin/stem-loop structure, wherein the stem portion sequence is indicated. The loop portion may comprise of an uncopiable linkage, or cleavable nucleotide(s).

(C) in addition to any combination of design components mentioned in (A-T) an ATO which comprises hairpin/stem-loop structure, wherein the stem portion sequence is indicated. The stem portion may comprise of an uncopiable linkage(s) or cleavable nucleotide(s).

(D) in addition to any combination of design components mentioned in (A-U) an ATO which comprises hairpin/stem-loop structure, wherein the stem portion sequence is indicated. The stem portion may comprise uncopiable linkage(s) or cleavable nucleotide(s). The loop region may contain random sequence, a degenerate sequence, a random sequence with nucleotide bias, or a target specific sequence capable of acting as a unique identifier.

(E) in addition to any combination of design components mentioned in (A-J) an ATO designed with two separate strands which comprises an upper separate strand which is complementary or substantially complementary to the whole or part of the lower strand of ATO, the lower part of ATO is equivalent to the ATO in (A).

(F) in addition to any combination of design components mentioned in (A-U) an ATO where the universal site is composed either entirely or partially of a sequence designed to function as an RNA polymerase promoter (G) in addition to any combination of design components mentioned in (A-U) an ATO where the universal site is composed partially of a sequence designed to function as an RNA polymerase promoter and a separate sequence designed to function as a priming site.
(H) in addition to any combination of design components mentioned in (A-U) an ATO which comprises hairpin/stem-loop structure, wherein the stem portion sequence is indicated, the loop portion may include an uncopiable linkage, cleavable nucleotide(s), and has a sequence designed to function as an RNA polymerase promoter.
(I) in addition to any combination of design components mentioned in (A-U) an ATO which comprises hairpin/stem-loop structure, where the stem portion is separated into two or more regions separated by a random sequence, a degenerate sequence, or a random sequence with nucleotide bias, that is spanned by an uncopiable linkage or an equivalent length of random sequence, a degenerate sequence, or a random sequence with nucleotide bias. (J) in addition to any combination of design components mentioned in (A-U) an ATO which comprises of a 3' sequence designed to be target specific, a random sequence, a degenerate sequence, or a random sequence with nucleotide bias 5' to the target specific sequence, and a universal sequence, 5' to the random sequence.
(K) in addition to any combination of design components mentioned in (A-U) an ATO where, the lower strand, contains a universal site is composed partially of a sequence designed to function as an RNA polymerase promoter and a separate sequence designed to function as a priming site, and the upper strand is a second oligo partially or fully complementary to lower strand capable of forming a double strand RNA polymerase promoter.
(L) in addition to any combination of design components mentioned in (A-U) an ATO which comprises hairpin/stem-loop structure, wherein the stem portion sequence is indicated. The loop region may contain random sequence, a degenerate sequence, a random sequence with nucleotide bias, or a target specific sequence capable of acting as a unique identifier, and comprise of an uncopiable linkage, or cleavable nucleotide(s).
(M) in addition to any combination of design components mentioned in (A-U) an ATO which comprises hairpin/stem-loop structure, wherein the stem portion sequence is indicated. The stem portion may comprise of an uncopiable linkage(s) or cleavable nucleotide(s). The loop region may contain random sequence, a degenerate sequence, a random sequence with nucleotide bias, or a target specific sequence capable of acting as a unique identifier.
(N) in addition to any combination of design components mentioned in (A-U) an ATO which comprises hairpin/stem-loop structure, where the stem portion is separated into two or more regions separated by a random sequence, a degenerate sequence, or a random sequence with nucleotide bias, that is spanned by an uncopiable linkage or an equivalent length of random sequence, a degenerate sequence, or a random sequence with nucleotide bias. The loop portion may comprise of an uncopiable linkage, or cleavable nucleotide(s).
(O) in addition to any combination of design components mentioned in (A-U) an ATO which has a 3' random sequence, a degenerate sequence, or a random sequence with nucleotide bias, and a very 3' end suitable for use as a primer to allow extension of the ATO.
(P) in addition to any combination of design components mentioned in (A-U) an ATO which has a 3' target specific sequence, and a very 3' end suitable for use as a primer to allow extension of the ATO.
(Q) in addition to any combination of design components mentioned in (A-U) an ATO which comprises a hairpin/stem-loop structure, wherein the stem portion sequence is indicated. The loop portion may comprise of an uncopiable linkage, or cleavable nucleotide(s). The 5' of the ATO comprises of a ligation acceptor, such as a phosphate.
(R) in addition to any combination of design components mentioned in (A-U) an ATO which comprises a hairpin/stem-loop structure, wherein the stem portion sequence is indicated. The loop portion may comprise of an uncopiable linkage, or cleavable nucleotide(s). The 5' of the ATO comprises of an affinity purification moiety, such as biotin.
(S) in addition to any combination of design components mentioned in (A-U) a linear ATO with a 5' comprising of a ligation acceptor, such as a phosphate.
(T) in addition to any combination of design components mentioned in (A-U) a linear ATO with a 5' comprises of an affinity purification moiety, such as biotin.
(U) in addition to any combination of design components mentioned in (A-U) a linear ATO composed only of a random sequence with a 3' blocked to prevent extension, and a 5' phosphate.

Figure 4:
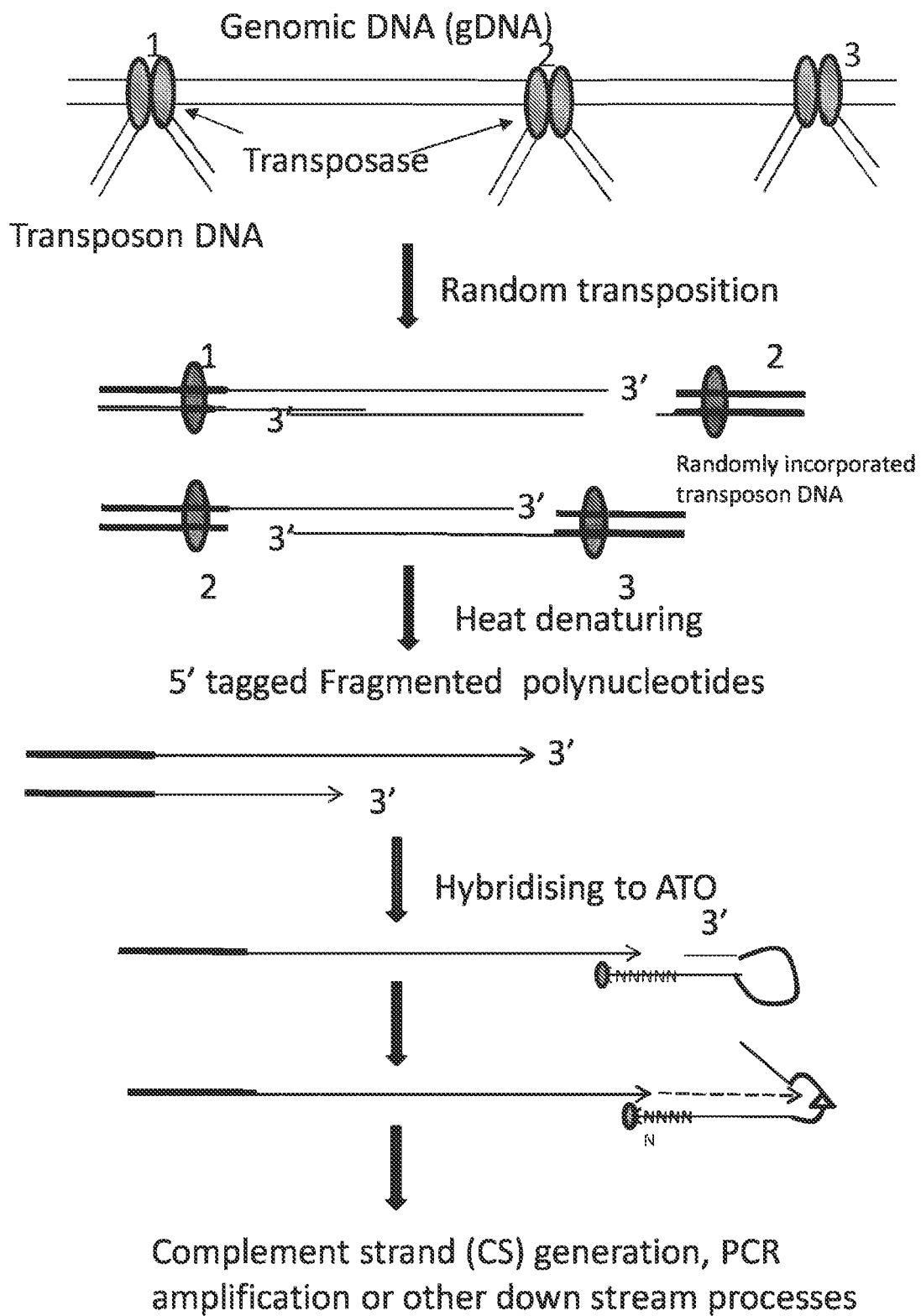

FIG. 4 depicts a schematic of an illustrative embodiment. The process of enzymatic fragmentation using nucleases, or physical shearing of DNA by sonication can be replace by fragmentation with the use of a transposase. In the step (i) a target double strand polynucleotide (DNA) is incubated with transposon DNA and a transposase. Once the random transposition reaction has completed, the target polynucleotide will now contain multiple copies of the transposon DNA which generates free 3' ends on the target polynucleotide, and free 5' ends of the transposon DNA. In the step (ii), ATO molecules are hybridised to single-stranded target polynucleotide sequences at one or more locations. The free 3' ends generated as the result of the random transposition of one strand of the target polynucleotide hybridises to the 3' random sequence portion of ATO, is trimmed if any 3' overhang is present, and is extended using ATO as template. The extension generates a modified target polynucleotide, which comprises a 5' universal sequence from the transposon DNA, a region of target polynucleotide 3' to the transposon DNA, a random sequence as UID 3' to the target polynucleotide, and a 3' second universal sequence as priming site. Following step (ii), the ATOs are digested or removed by affinity capture. In some embodiment, the ATO is not digested or removed. In the step (iii) the modified target polynucleotide are used as starting material for Complement strand (CS) generation, PCR amplification or other downstream processes.

Figure 5:
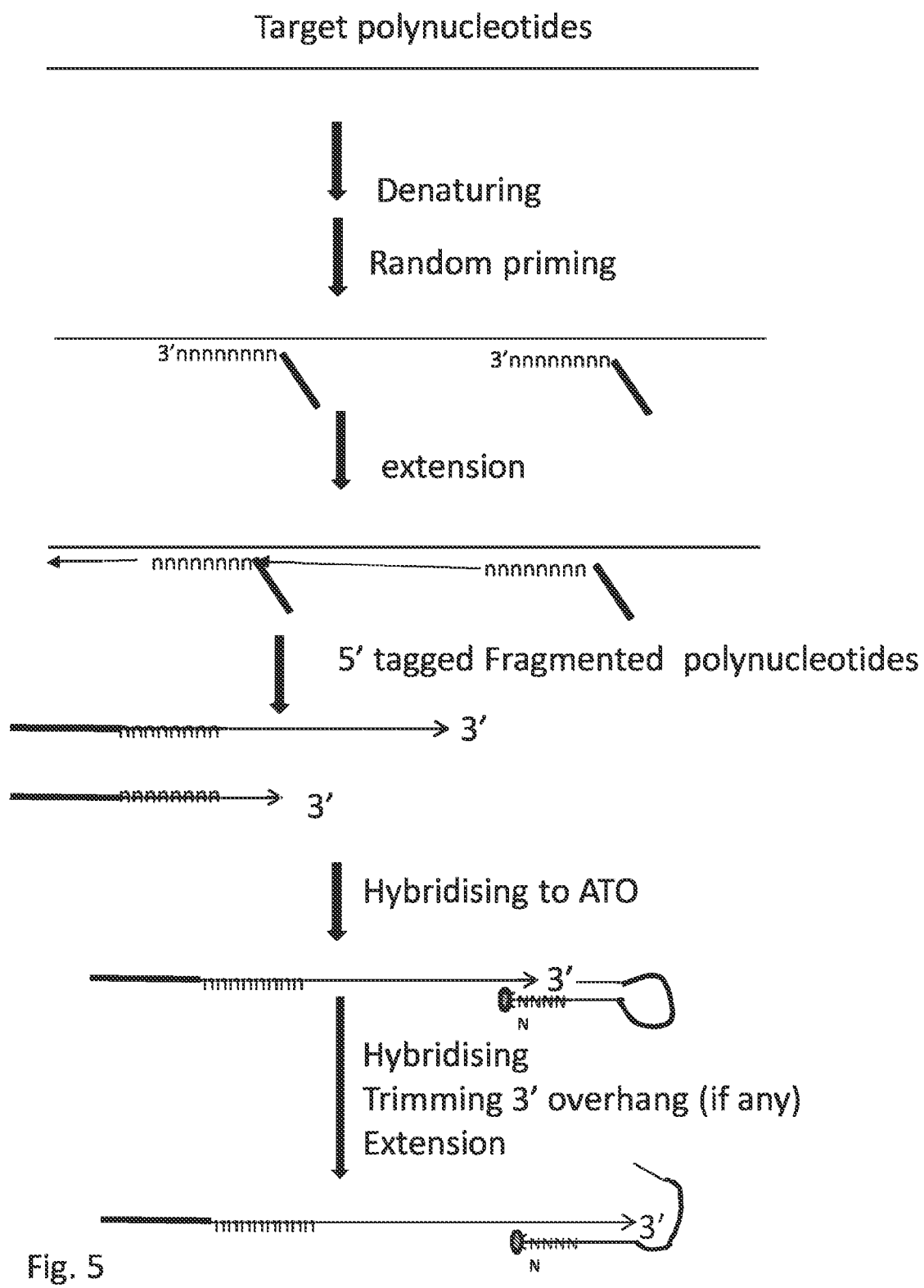

FIG. 5 depicts a schematic of an illustrative embodiment. A target polynucleotide (PCR products, or DNA, or RNA of any source, or any mixture thereof) may be double-stranded, only one of two strands is shown (forward strand). In the step (i), ATO molecules are randomly hybridised to single-stranded target polynucleotide sequences at one or more locations. In the step (ii) the 3' end of the ATO molecules are extended using the target polynucleotide as template. The extension generates a modified target polynucleotide copy, which comprises a 5' universal sequence, a random sequence as UID, and at the 3' end a copy of the target polynucleotide. Following step (ii) the modified target polynucleotide copy is purified to remove unused ATO. In some embodiment, the ATO is not digested or removed. In the step (iii) a second ATO is hybridised to the modified target polynucleotide at one or more locations. The 3' end of the modified target polynucleotide copy hybridises to the 3' random sequence portion of ATO, is trimmed if any 3' overhang is present, and is extended using ATO as template. The extension generates a dual modified target polynucleotide, which comprises 3' and 5' universal sites which can act as priming sites, internal to these are two different random sequences as UID, and centrally, a copy of the target polynucleotide.

Figure 6:
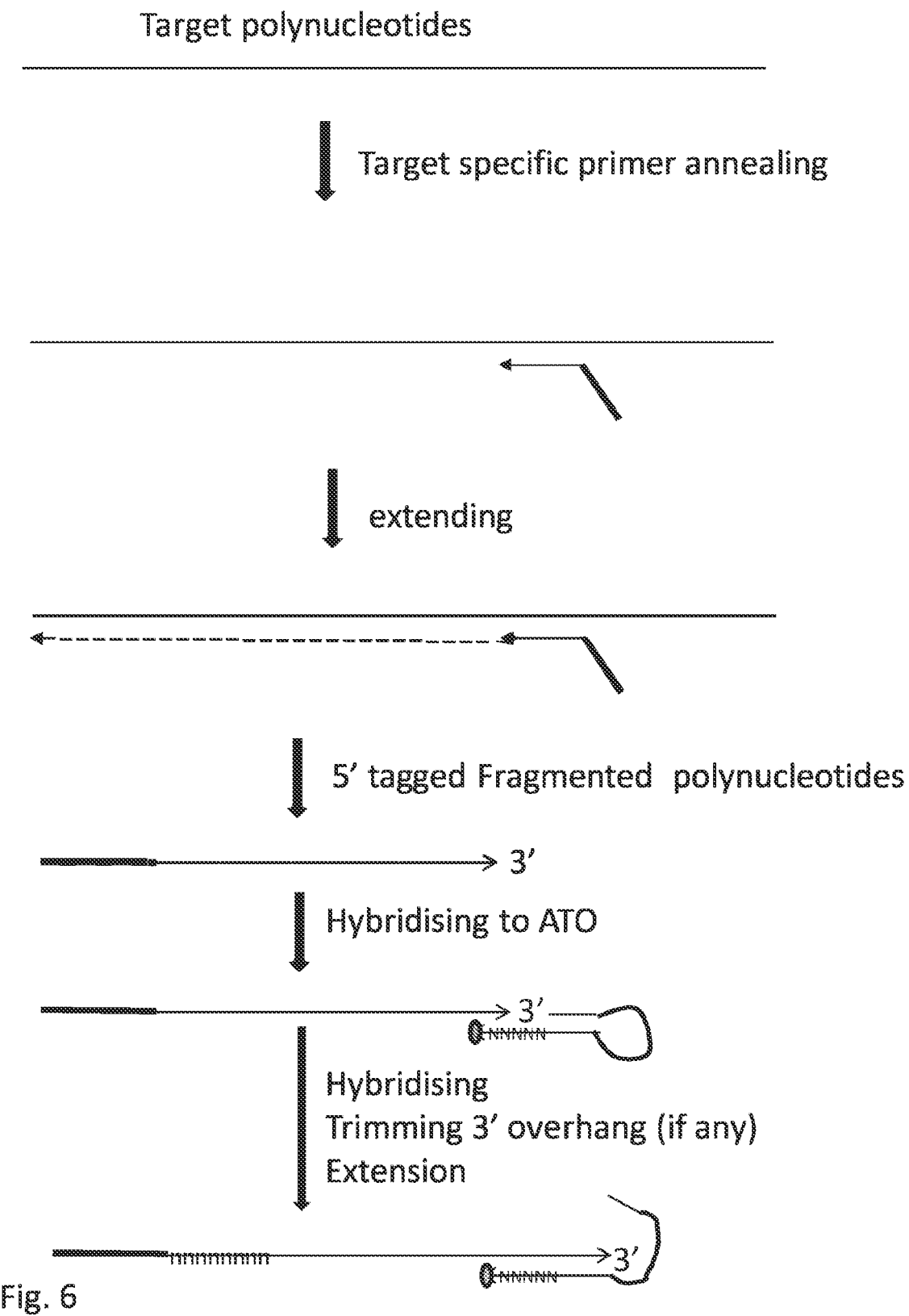

FIG. 6 depicts a schematic of an illustrative embodiment. A target polynucleotide (PCR products, or DNA, or RNA of any source, or any mixture thereof) may be double-stranded, only one of two strands is shown (forward strand). In the step (i), ATO molecules designed with target specific sequences are hybridised to single-stranded target polynucleotide sequences at one or more locations. In the step (ii) the 3' ends of the ATO molecules are extended using the target polynucleotide as template. The extension generates a modified target polynucleotide copy, which comprises a 5' universal sequence, a random sequence as UID, and at the 3' end a copy of the target polynucleotide. Following step (ii) the modified target polynucleotide copy is purified to remove unused ATO. In some embodiment, the ATO is not digested, or removed. In the step (iii) a second ATO is hybridised to the modified target polynucleotide at one or more locations. The 3' end of the modified target polynucleotide copy hybridises to the 3' random sequence portion of ATO, is trimmed if any 3' overhang is present, and is extended using ATO as template. The extension generates a dual modified target polynucleotide, which comprises 3' and 5' universal sites which can act as priming sites, internal to these are two different random sequences as UID, and centrally, a copy of the target polynucleotide.

Figure 7:
Figure 7:
Figure 7:
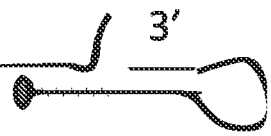
Figure 7:
Figure 7:
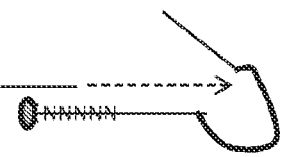

FIG. 7 depicts a schematic of an illustrative embodiment. A target polynucleotide (PCR products, or DNA, or RNA of any source, or any mixture thereof) may be double-stranded, only one of two strands is shown (forward strand). In the step (i), target polynucleotides are fragmented before single-stranded target polynucleotide randomly hybridise to ATO molecules at one or more locations. The 3' end of the target polynucleotide hybridises to the 3' random sequence portion of ATO, is trimmed if any 3' overhang is present, and is extended using ATO as template. The extension generates a modified target polynucleotide, which comprises a random sequence as UID and a 3' universal sequence as priming site.

Figure 8:
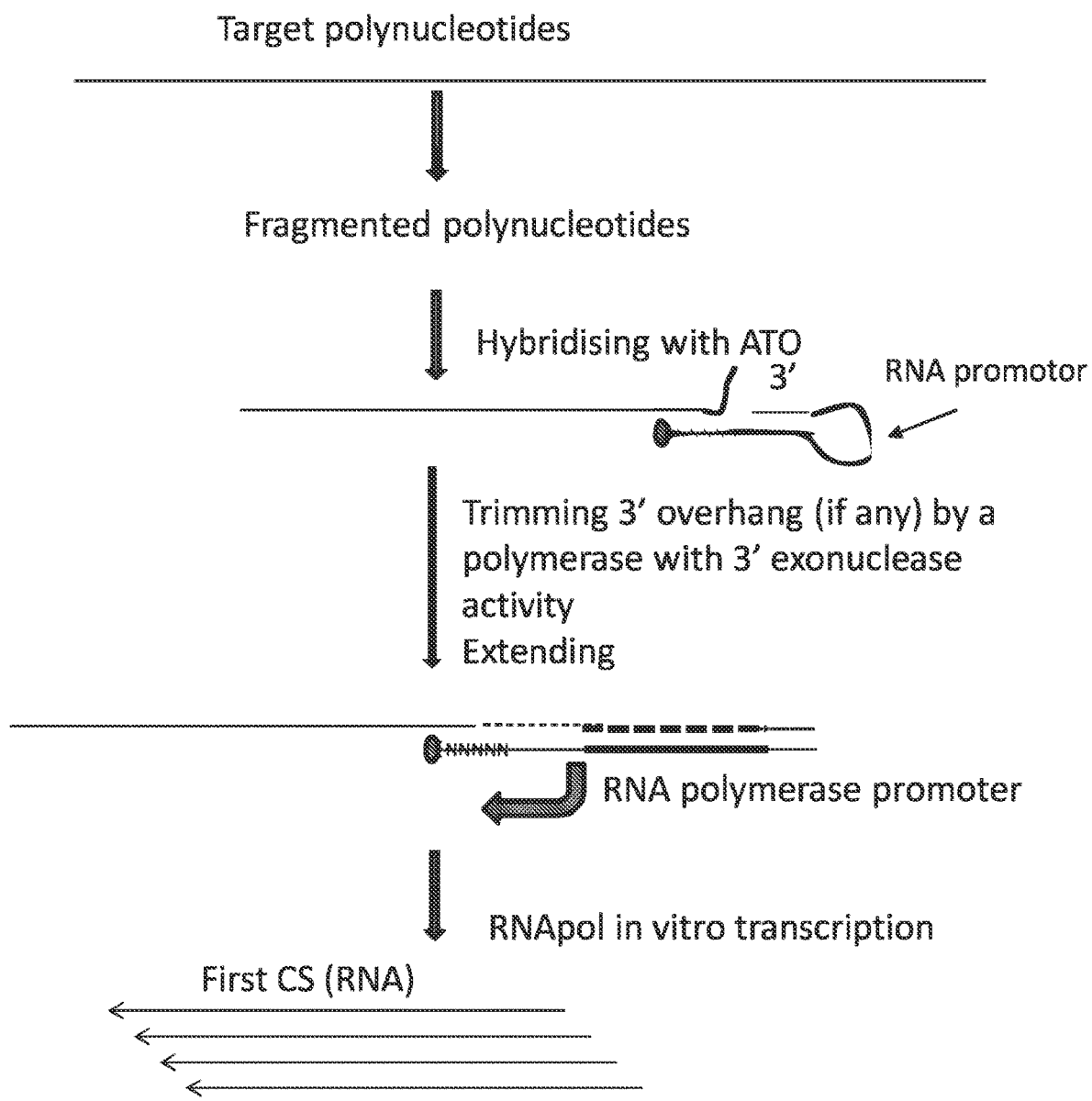
Figure 8:
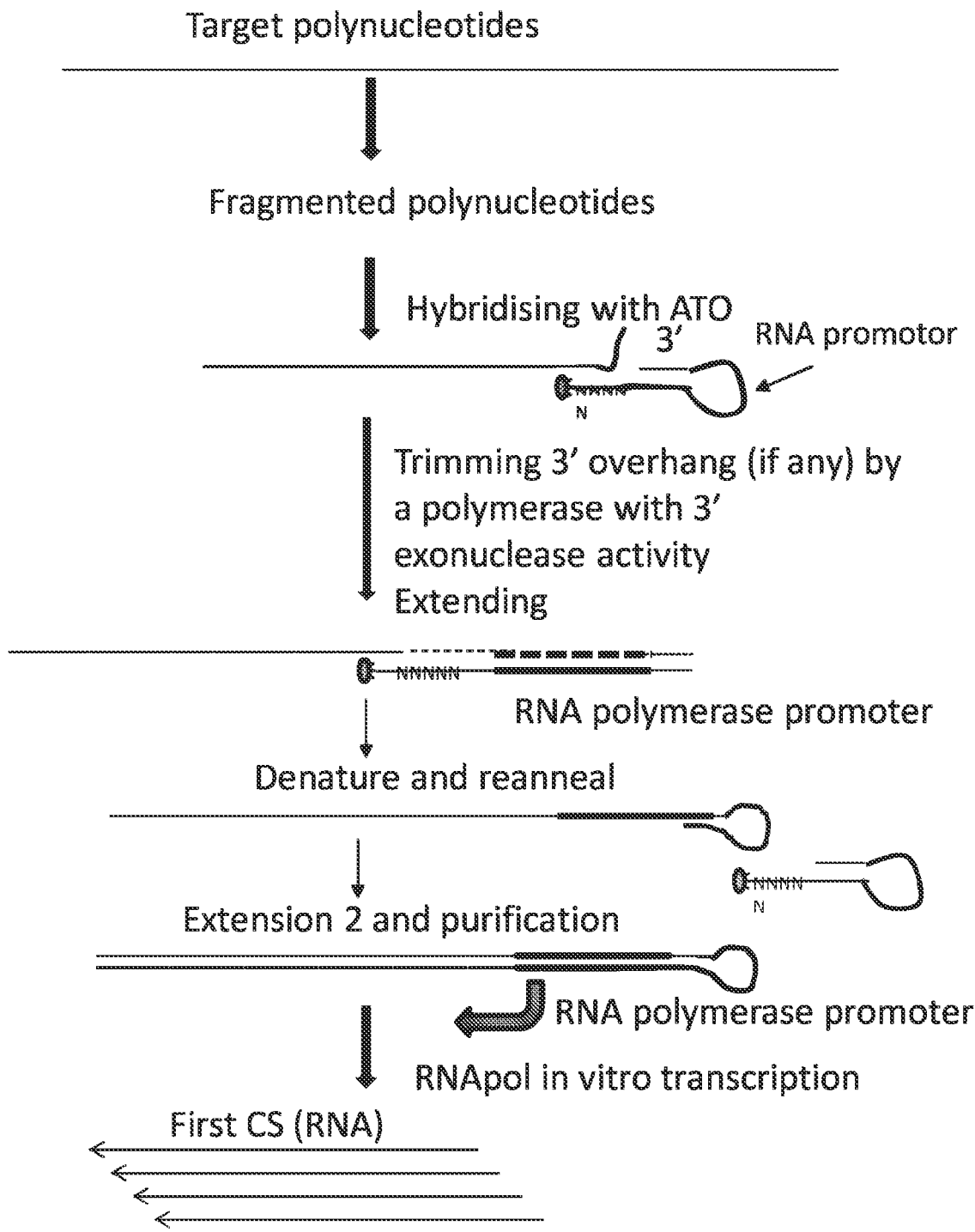

FIG. 8 depicts a schematic of an illustrative embodiment. (a) A target polynucleotide (PCR products, or DNA, or RNA, or any mixture thereof) may be double-stranded, only one of two strands is shown (forward strand). In the step (i), target polynucleotides are fragmented before single-stranded target polynucleotide randomly hybridise to ATO molecules at one or more locations, the ATO contains a RNA polymerase promoter sequence. The 3' end of the target polynucleotide hybridises to the 3' random sequence portion of ATO, is trimmed if any 3' overhang is present, and is extended using ATO as template. The extension generates a modified target polynucleotide including a region of double strand sequence between the target polynucleotide and the ATO, which comprises a random sequence as UID, and a 3' universal sequence including a RNA polymerase promoter. Following step (i) the modified target polynucleotide is optionally purified to remove unused ATO. In some embodiments, the ATO is not digested, or removed. In the step (ii) the double strand RNA polymerase promoter of the modified target polynucleotide is used to generate RNA copies (first complement sequence) of the modified target polynucleotide.

(b) A target polynucleotide (PCR products, or DNA, or RNA of any source, or any mixture thereof) may be double-stranded, only one of two strands is shown (forward strand). In the step (i), target polynucleotides are fragmented before single-stranded target polynucleotide randomly hybridise to ATO molecules at one or more locations, the ATO contains a RNA polymerase promoter sequence. The 3' end of the target polynucleotide hybridises to the 3' random sequence portion of ATO, is trimmed if any 3' overhang is present, and is extended using ATO as a template. The extension generates a modified target polynucleotide, which comprises a random sequence as UID and a 3' universal sequence as priming site which includes complementary regions capable of forming a hairpin at the 3' end of the modified target polynucleotide. Following step (i), the ATOs are digested or removed by affinity capture. In some embodiments, the ATO is not digested or removed. In the step (ii) the 3' end of the modified target polynucleotide is allowed to form a small hairpin by annealing to itself, the 3' end then acts as a primer which once extended will generate the first complement sequence, including a double strand RNA polymerase promoter. In the step (iii) the double strand RNA polymerase promoter of the modified target polynucleotide is used to generate RNA copies (first complement sequence) of the modified target polynucleotide.

Figure 9:
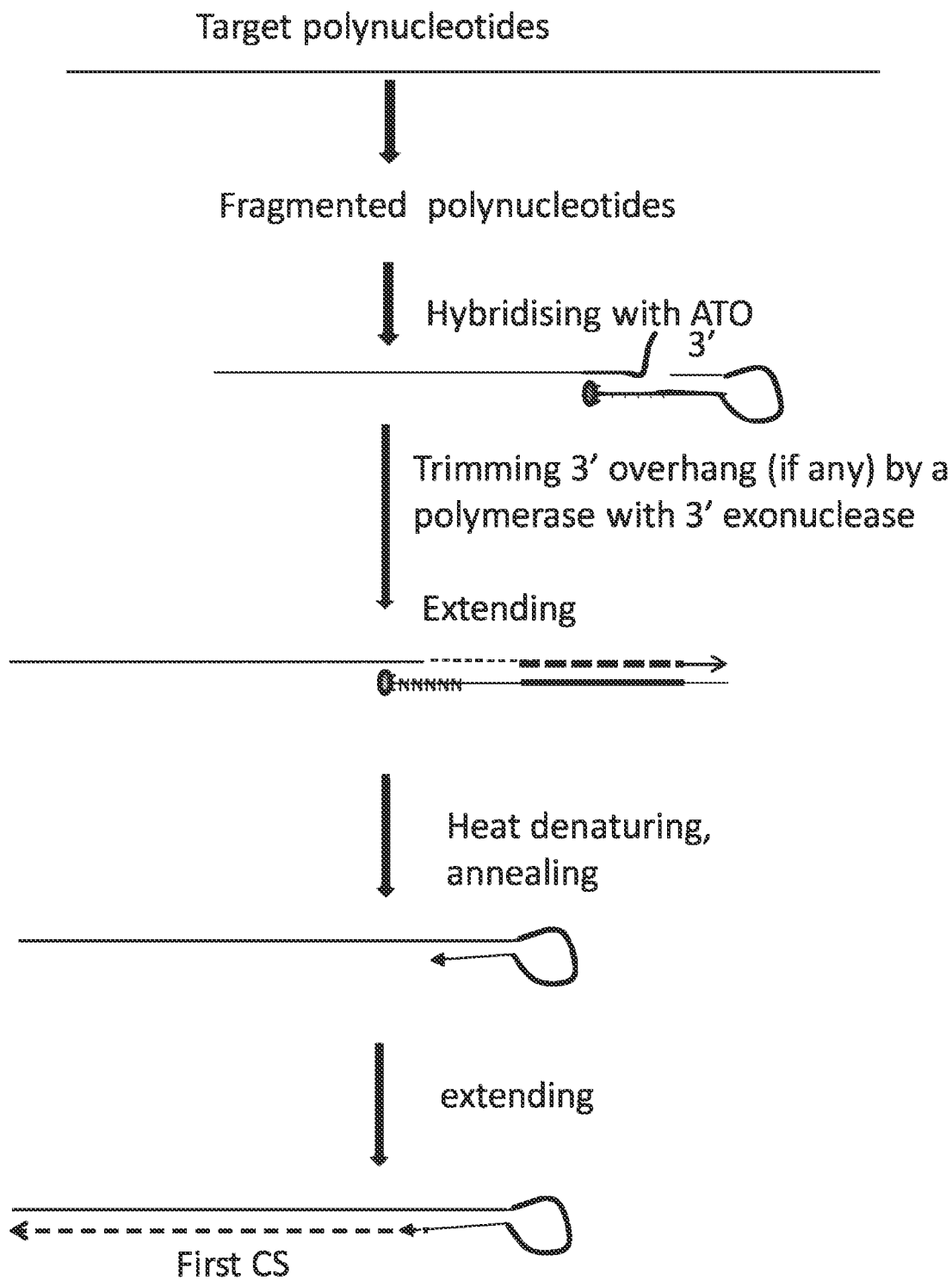

FIG. 9 depicts a schematic of an illustrative embodiment. A target polynucleotide (PCR products, or DNA, or RNA of any source, or any mixture thereof) may be double-stranded, only one of two strands is shown (forward strand). In the step (i), target polynucleotides are fragmented before single-stranded target polynucleotide randomly hybridise to ATO molecules at one or more locations. The 3' end of the target polynucleotide hybridises to the 3' random sequence portion of ATO, is trimmed if any 3' overhang is present, and is extended using ATO as a template. The extension generates a modified target polynucleotide, which comprises a random sequence as UID and a 3' universal sequence as priming site which includes complementary regions capable of forming a hairpin at the 3' end of the modified target polynucleotide. Following step (i), the ATOs are digested or removed by affinity capture. In some embodiment, the ATO is not digested or removed. In the step (ii) the 3' end of the modified target polynucleotide is allowed to form a small hairpin by annealing to itself, the 3' end then acts as a primer which once extended will generate the first complement sequence.

Figure 10:
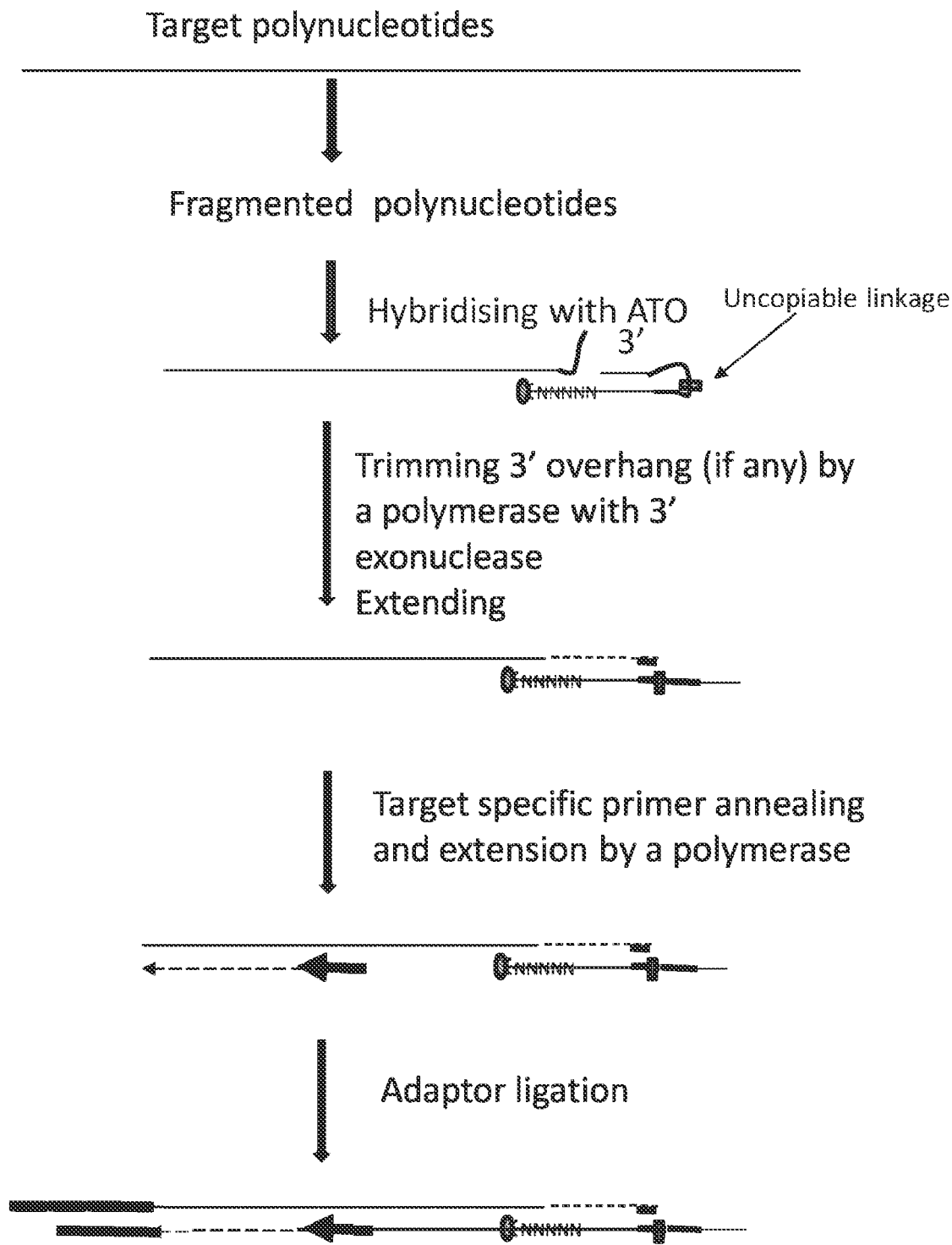

FIG. 10 depicts a schematic of an illustrative embodiment. A target polynucleotide (PCR products, or DNA, or RNA of any source, or any mixture thereof) may be double-stranded, only one of two strands is shown (forward strand). In the step (i), target polynucleotides are fragmented before single-stranded target polynucleotide randomly hybridise to ATO molecules at one or more locations. The 3' end of the target polynucleotide hybridises to the 3' random sequence portion of ATO, is trimmed if any 3' overhang is present, and is extended using ATO as a template. The extension generates a modified target polynucleotide, which comprises a random sequence as UID and a 3' universal sequence as priming site. Following step (i), the ATOs are digested or removed by affinity capture. In some embodiment, the ATO is not digested or removed. In the step (ii) target specific primers are added to the modified target polynucleotide which are extended by a polymerase until reaching the 5' end of the modified target polynucleotide. In the step (iii), double strand adaptors are mixed with the modified target polynucleotide along with suitable enzymes, and the adaptors are subsequently ligated to the 5' double strand DNA of the modified target polynucleotide.

Figure 11:
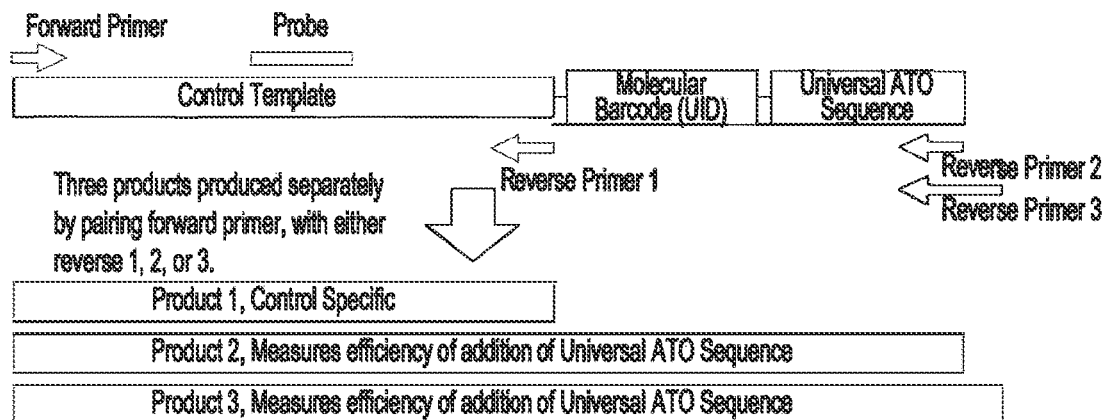
Figure 11:
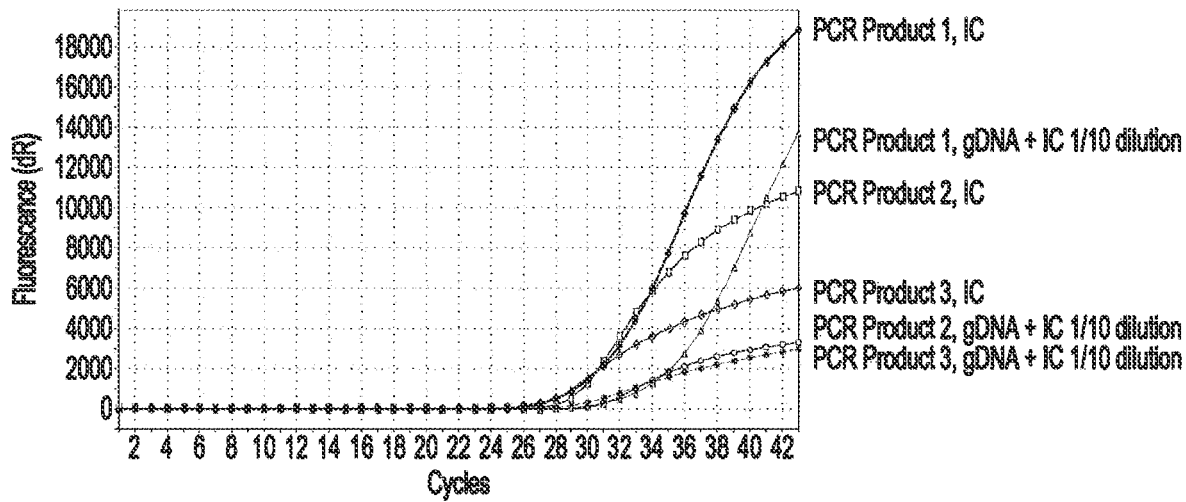

FIG. 11 depicts a schematic of an illustrative embodiment. To measure the efficiency at which 3' extension of the target polynucleotide occurs to generate the modified target, polynucleotide quantitative PCR (qPCR) was used. The target polynucleotide used was a single strand DNA oligo of known length and sequence, the internal control (IC). The target polynucleotide used was also genomic DNA mixed with 10% the quantity of single strand DNA oligo of known length and sequence, the internal control (IC). Once the modified target polynucleotide has been produced they were both independently used as a template for 3 different qPCR reactions, one with two primers located within the target polynucleotide sequence (Forward Primer and Reverse Primer 1), one with a primer located within the target polynucleotide sequence and one present in the universal sequenced added to the modified target polynucleotide (Forward Primer and Reverse Primer 2), and another with a primer located within the target polynucleotide sequence and one present at the end of the universal sequence added to the modified target polynucleotide with a tail which was not homologous with the modified target polynucleotide (Forward Primer and Reverse Primer 3), all of these reactions included a dual labelled qPCR probe located within the target polynucleotide (Probe). The 'CT' value at which a fluorescent amplification single was detected for the IC control specific primers when compared to the 'CT' value at which a fluorescent amplification single was detected for primer pairs located within the IC and the universal sequence gives a proportional indication of the efficiency of the target polynucleotide 3' extension. As the 'CT' values are very similar the efficiency can be interpreted as between 50-100%.

Figure 12:
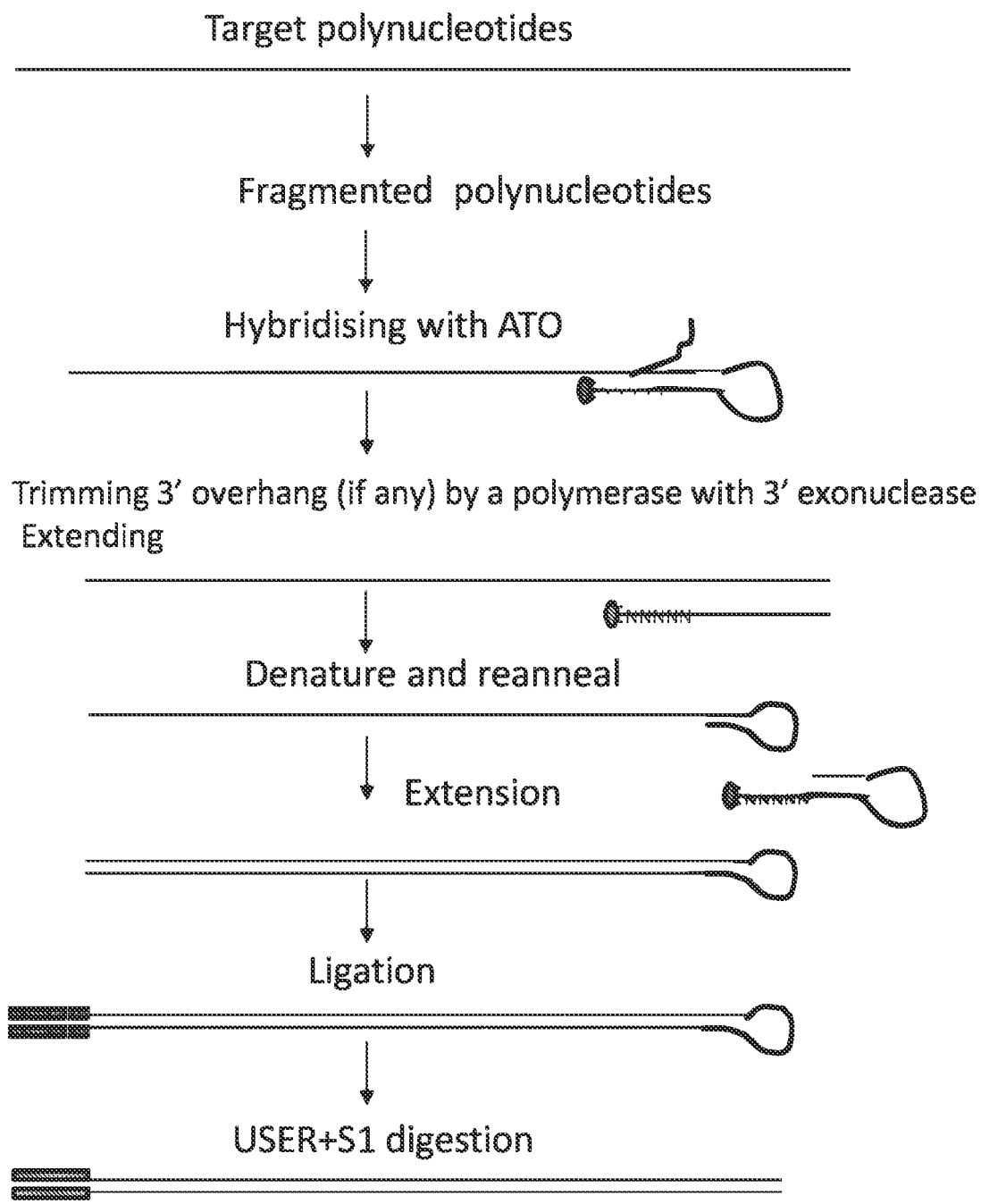

FIG. 12 depicts a schematic of an illustrative embodiment. A target polynucleotide (PCR products, or DNA, or RNA of any source, or any mixture thereof) may be double-stranded, only one of two strands is shown (forward strand). In the step (i), target polynucleotides are fragmented before single-stranded target polynucleotide randomly hybridise to ATO molecules at one or more locations. The 3' end of the target polynucleotide hybridises to the 3' random sequence portion of ATO, is trimmed if any 3' overhang is present, and is extended using ATO as a template. The extension generates a modified target polynucleotide, which comprises a random sequence as UID and a 3' universal sequence as priming site which includes complementary regions capable of forming a hairpin at the 3' end of the modified target polynucleotide. In the step (ii) the 3' end of the modified target polynucleotide is allowed to form a small hairpin by annealing to itself. In the step (iii) the 3' end then acts as a primer which once extended will generate the first complementary strand. Following step (iii), the ATOs are digested or removed by affinity capture. In some embodiment, the ATO is not digested or removed. In the step (iv) the double-stranded DNA of first CS is ligated to an adaptor through double-strand ligation by a DNA ligase. In the step (v) the remaining ATO are digested and the hairpin broken by incubation of the reaction mixture with a mixture of dU-glycosylase, an apurinic/apyrimidinic endonuclease, and S1 nuclease. The final double strand product and then directly be used for sequencing on a compatible Next Generation Sequencer (e.g. MiSeq).

Figure 13:
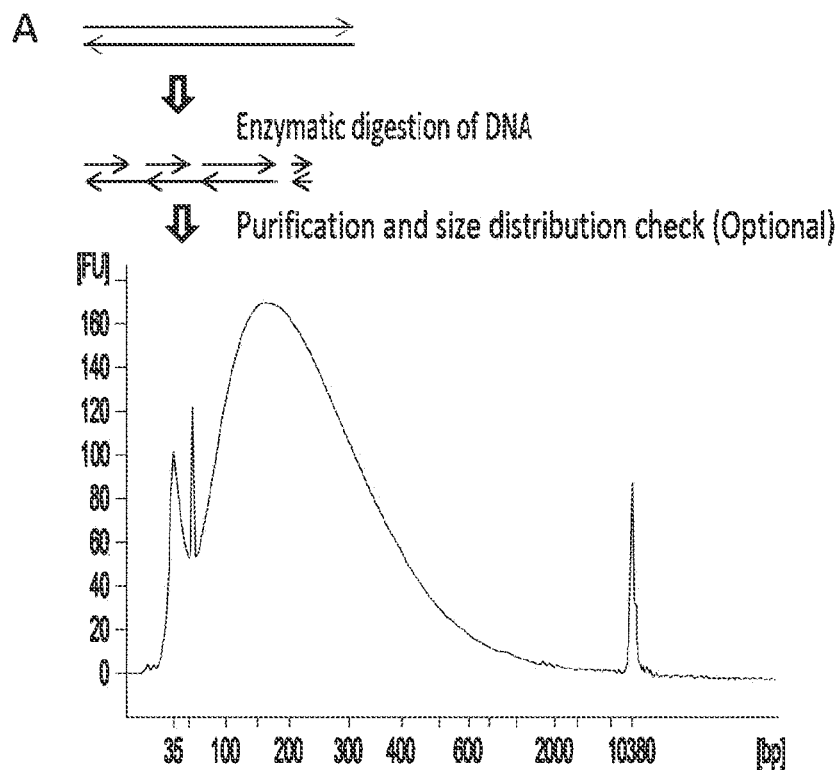
Figure 13:
Figure 13:
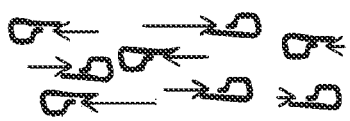
Figure 13:
Figure 13:
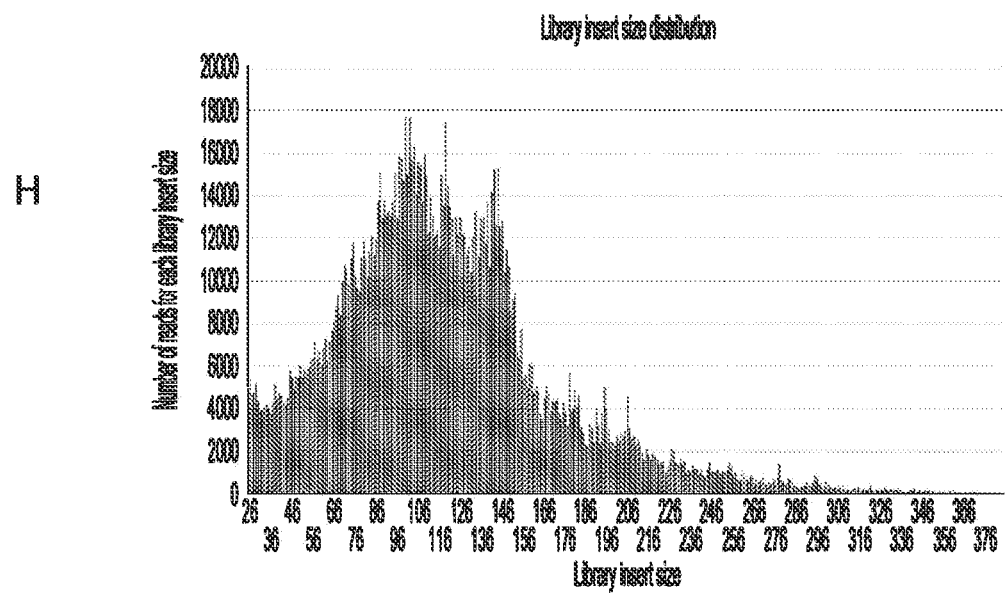
Figure 13:
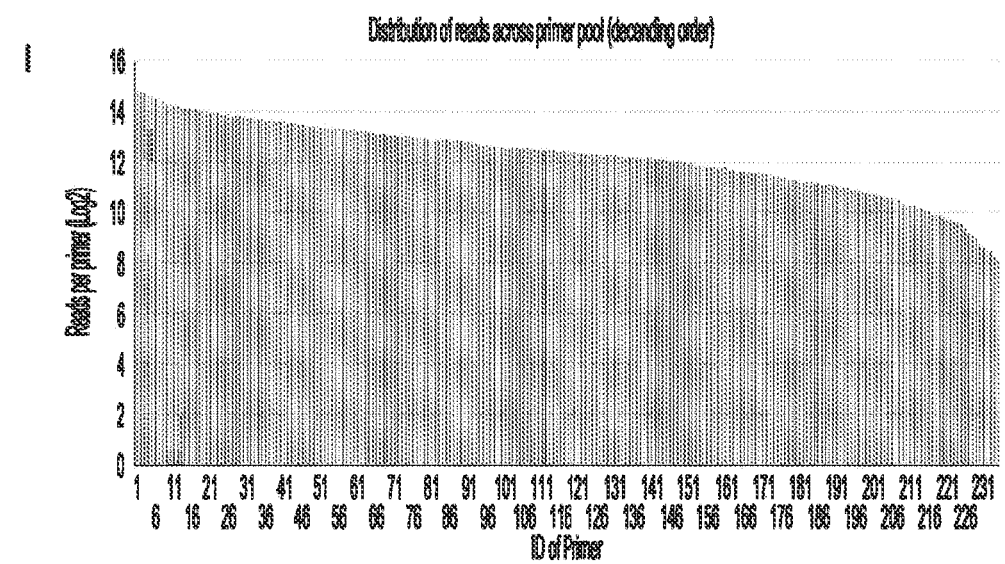
Figure 13:
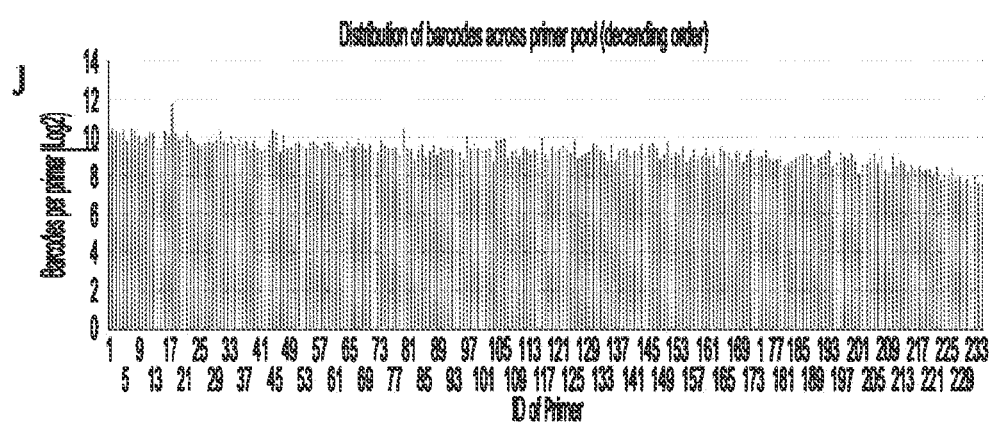

FIG. 13 depicts a schematic of an illustrative embodiment. Depicted are all the steps used in generation of a targeted amplicon next generation sequencing panel from starting material to analysis of sequencing data. A target polynucleotide (PCR products, or DNA, or RNA, or any mixture thereof) may be double-stranded, only one of two strands is shown (forward strand). In the step (i), target polynucleotides are enzymatically fragmented. In the step (II) the size distribution of the fragmented target polynucleotide was determined using a high sensitivity bioanalyzer chip. In the step (iii), fragmented target polynucleotides are randomly hybridised to ATO molecules at one or more locations. The 3' end of the target polynucleotide hybridises to the 3' random sequence portion of ATO, is trimmed if any 3' overhang is present, and is extended using ATO as template. The extension generates a modified target polynucleotide, which comprises a 3' random sequence as UID, a 3' universal sequence as priming site. In the step (iii) the ATOs are digested or removed by affinity capture. In some embodiment, the ATO is not digested or removed. In the step (iv) the modified target polynucleotide, a universal primer designed to bind to the universal site on the ATO, a pool of gene specific primers, suitable buffers, suitable enzymes, dNTPs and other additives are combined and used to exponentially amplify the modified target polynucleotide. In the step (v) the PCR products are purified. In the step (vi) the first PCR product, a second universal primer designed to bind to the universal site in the PCR product, a second, nested, pool of gene specific primers, suitable buffers, suitable enzymes, dNTPs and other additives are combined and used to exponentially amplify the modified target polynucleotide. In the step (vii) the second PCR products are purified. In step (viii) the size distribution of the final sequencing library was determined using a high sensitivity bioanalyzer chip. The library was then sequenced using a MiSeq sequencer with 150 bp pair-end sequencing. The sequencing data was subsequently analysed using a combination of the bwa aligner and custom data filtering python scripts. Data figure (H) represents the distribution of the sizes of the insert demined from the sequencing data generated by the MiSeq, (I) represents the distribution of the reads across all of the primers present in the pools used in the exponential amplifications, (J) shows the number of 'barcode families' identified in the sequencing data of a family size with at least 3 reads.

Figure 14:
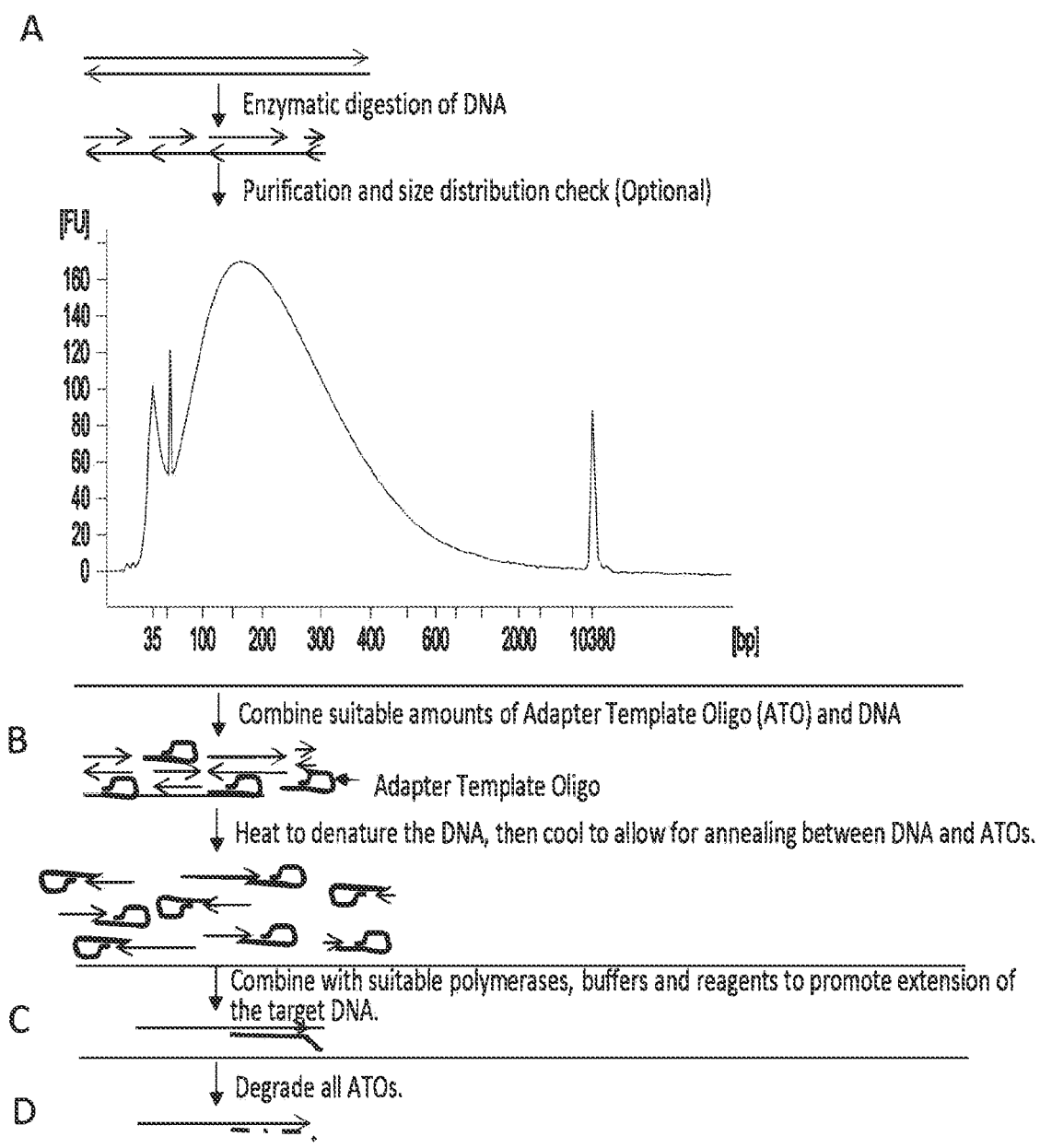

FIG. 14 depicts a schematic of an illustrative embodiment. Depicted are all the steps used in generation of a whole genome DNA library from starting material to final library. A target polynucleotide (PCR products, or DNA, or RNA, or any mixture thereof) may be double-stranded, only one of two strands is shown (forward strand). In the step (i), target polynucleotides are enzymatically fragmented. In the step (II) the size distribution of the fragmented target polynucleotide was determined using a high sensitivity bioanalyzer chip. In the step (iii), fragmented target polynucleotides are randomly hybridised to ATO molecules at one or more locations. The 3' end of the target polynucleotide hybridises to the 3' random sequence portion of ATO, is trimmed if any 3' overhang is present, and is extended using ATO as template. The extension generates a modified target polynucleotide, which comprises a 3' random sequence as UID, a 3' universal sequence as priming site. In the step (iii) the ATOs are digested or removed by affinity capture. In some embodiment, the ATO is not digested or removed. In the step (iv) the modified target polynucleotide, a universal primer designed to bind to the universal site on the ATO, suitable buffers, suitable enzymes, dNTPs and other additives are combined and used to linearly amplify the modified target polynucleotide to generate first CS (complement sequence). The products are then optionally purified. In the step (v) the linear CS are randomly hybridised to ATO molecules at one or more locations. The 3' end of the linear CS hybridises to the 3' random sequence portion of ATO, is trimmed if any 3' overhang is present, and is extended using ATO as template. The extension generates a modified CS, which at each end comprises a random sequence as UID, a different 3' and 5'universal sequences as priming sites. In the step (vi) the ATOs are digested or removed by affinity capture. In some embodiment, the ATO is not digested or removed. In the step (vii) the modified CS product, two different universal primers designed to bind to the universal sites at the 5' and 3' ends of the modified CS product, necessary buffers, enzymes, dNTPs and other additives are combined and used to exponentially amplify the modified CS product. In the step (viii) the second PCR products are purified. In step (ix) the size distribution of the final sequencing library was determined using a high sensitivity bioanalyzer chip.

Figure 15:
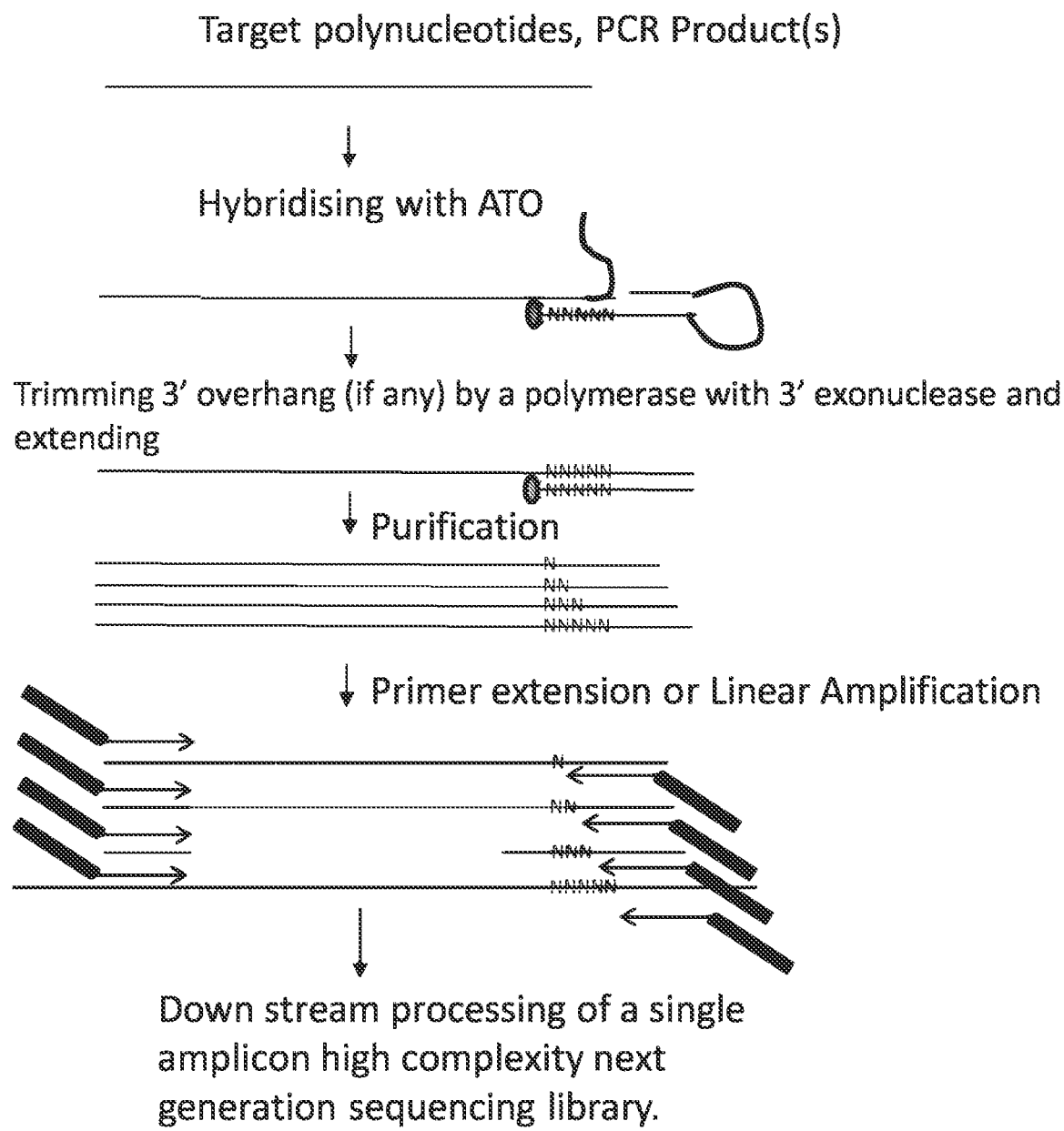

FIG. 15 depicts a schematic of an illustrative embodiment. A target polynucleotide (PCR products, or DNA, or RNA, or any mixture thereof) may be double-stranded, only one of two strands is shown (forward strand). In the step (i), single-stranded target polynucleotides are randomly hybridised to ATO molecules at one or more locations. The 3' end of the target polynucleotide hybridises to the 3' random sequence portion of ATO, is trimmed if any 3' overhang is present, and is extended using ATO as template. The extension generates a modified target polynucleotide, which comprises a variable length random sequence as UID, a 3' universal sequence as priming site. In the step (ii) the modified target polynucleotide is purified to remove unused ATO. In some embodiment, the ATO is not digested, or removed. In the step (iii) the modified target polynucleotide, a universal primer designed to bind to the universal site in the PCR product, a gene specific primer, suitable buffers, suitable enzymes, dNTPs, and other additives are combined and used to exponentially amplify the modified target polynucleotide.

Figure 16:
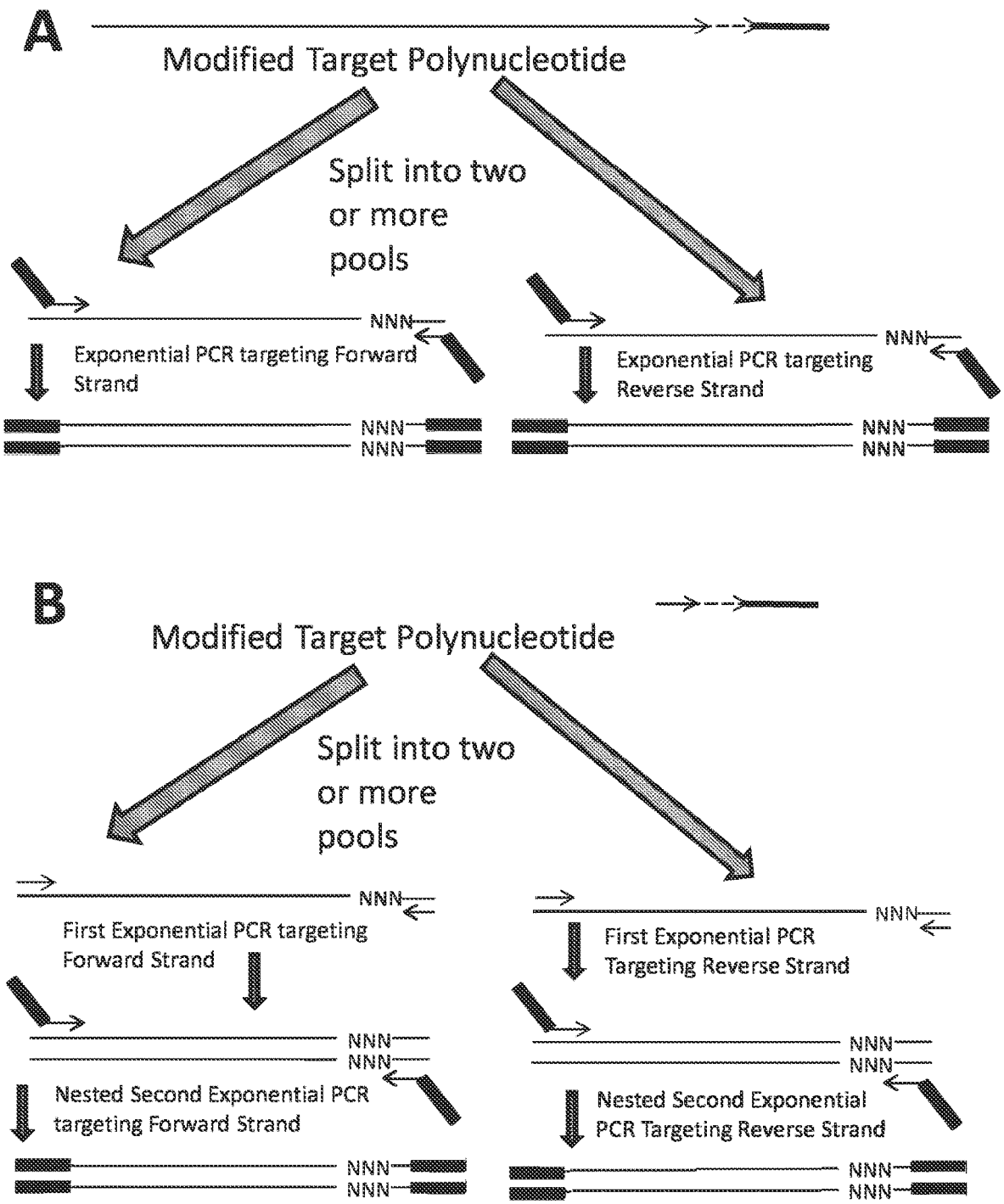
Figure 16:
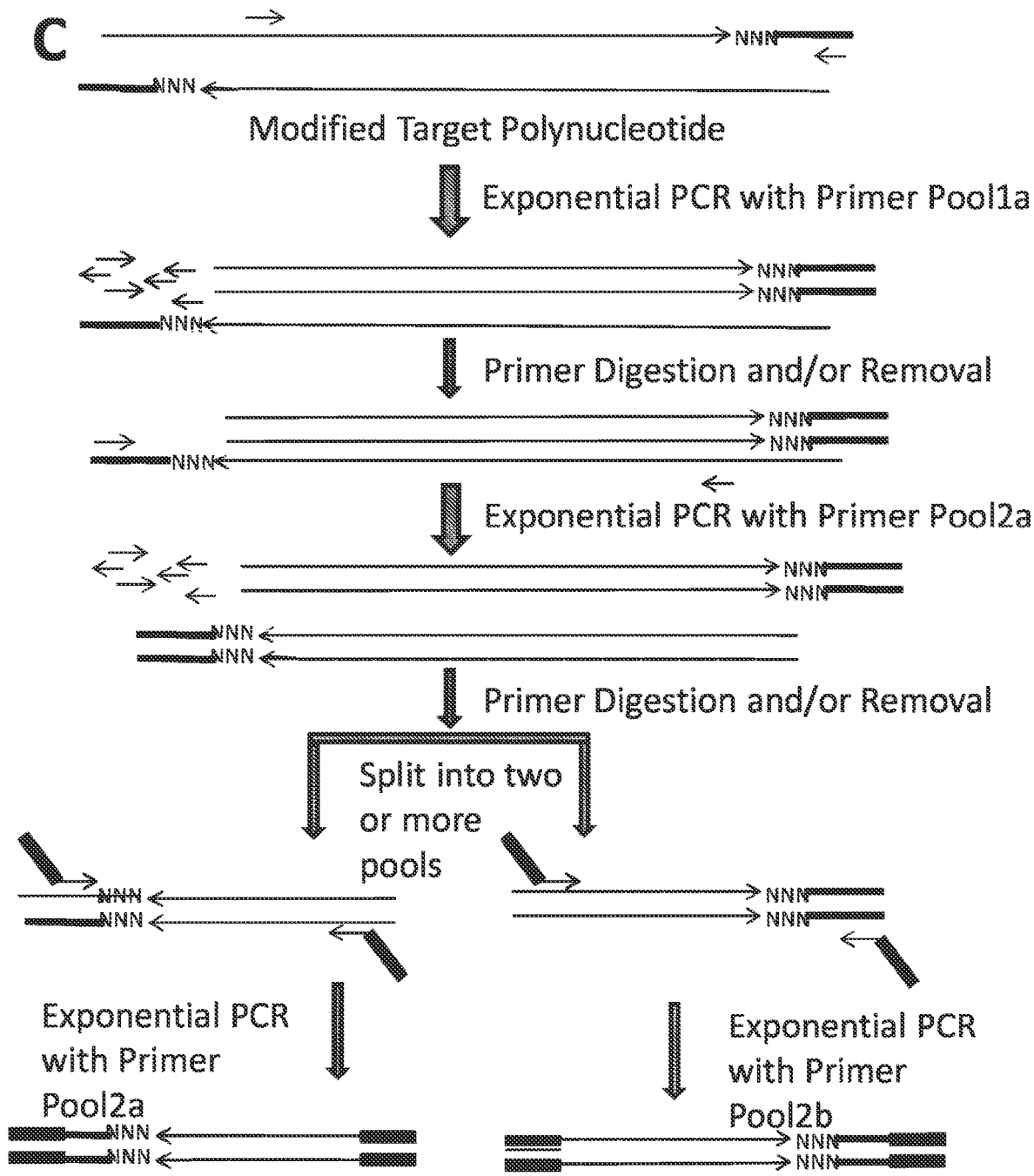
Figure 16:
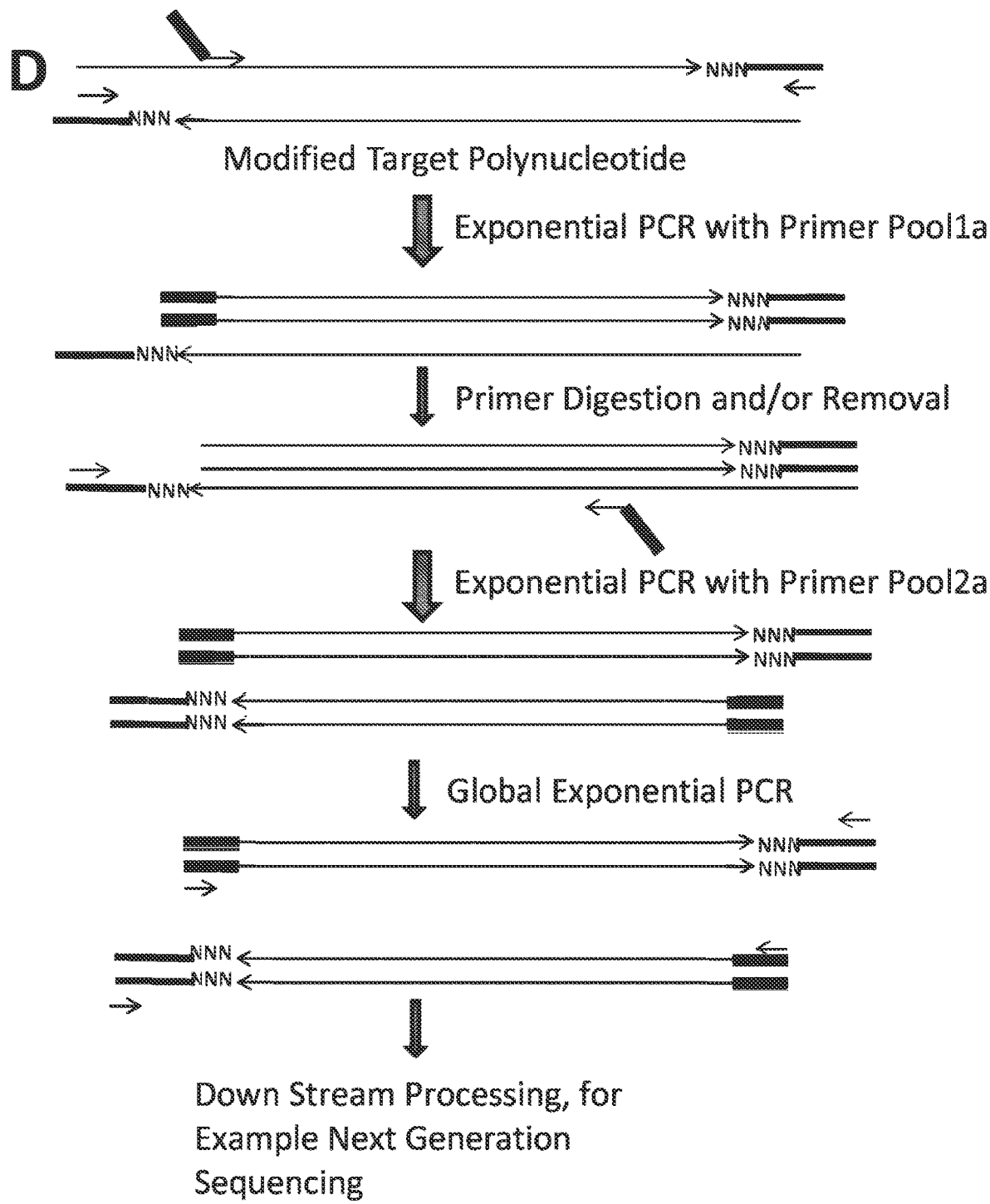

FIG. 16 depicts a schematic of an illustrative embodiment. A target polynucleotide (PCR products, or DNA, or RNA, or any mixture thereof) may be double-stranded, only one of two strands is shown (forward strand).

(A) The modified target polynucleotide is divided into two approximately equal aliquots. To each of these aliquots is added a universal primer, the 3' of this primer is designed to hybridise to the universal sequence of the modifier target polynucleotide and has a 5' tail containing sequences necessary for next generation sequencing. To each aliquot a different target specific primer or pool of target specific primers is added, the primers in each pool are designed to amplify either the forward or reverse strand of target regions of the target polynucleotide. The target specific primers comprise a 3' target specific portion with a 5' universal portion containing sequences necessary for next generation sequencing. The two separate mixes are amplified with multiple cycles of PCR amplification using both the universal primer and a target specific primer(s). The product of this amplification will be two separate pools of PCR products each of which has amplified one or other of the strands of the original polynucleotide, and will include all necessary sequences for compatibility with next generation sequencing.

(B) The modified target polynucleotide is divided into two approximately equal aliquots. To each of these aliquots is added a universal primer, the primer is designed to hybridise to the universal sequence of the modifier target polynucleotide, with or without an additional 5' universal sequence. To each aliquot a different target specific primer or pool of target specific primers is added, the primers in each pool are designed to amplify either the forward, or reverse strand of target regions of the target polynucleotide. The target specific primers comprise a 3' target specific sequence with or without a 5' universal sequence. The two separate mixes are amplified with multiple cycles of PCR amplification using both the universal primer and a pool of target specific primers. The product of this amplification will be two separate pools of PCR products each of which has amplified one or other of the strands of the original polynucleotide, with or without '3 and 5' universal sequences. The first amplification product may be purified to remove no longer necessary reagents from the first PCR reaction. Each of the two separate pools of PCR products are combined with a second universal primer, the universal primer used in first PCR or nested universal primer, the 3' of this primer is designed to hybridise to universal sequence of the first PCR product and has a 5' tail containing sequences necessary for next generation sequencing, and a different nested target specific primer or pool of nested target specific primers which comprise a 3' target specific portion with a 5' universal portion containing sequences necessary for next generation sequencing. The two separate mixes are amplified with multiple cycles of PCR amplification using both the universal primer and a pool of target specific primers. The product of this amplification will be two separate pools of PCR products each of which has amplified one or other of the strands of the original polynucleotide, and will include all necessary sequences for compatibility with next generation sequencing.

(C) The modified target polynucleotide is combined with a universal primer, the primer is designed to hybridise to universal the sequence of the modifier target polynucleotide, with or without an additional 5' universal sequence. The modified target polynucleotide is then linear amplified by one or more rounds of amplification. The linear amplification product may be purified to remove no longer necessary reagents from the linear amplification reaction. The linear amplification product is divided into two approximately equal aliquots. To each of these aliquots is added a universal primer, the 3' of this primer is designed to hybridise to the universal sequence of the modifier target polynucleotide and has a 5' tail containing sequences necessary for next generation sequencing. To each aliquot a different target specific primer or pool of target specific primers is added, each pool contains primers designed to amplify target regions of either the forward or reverse strand of the target polynucleotide. The target specific primers comprise a 3' target specific portion with a 5' universal portion containing sequences necessary for next generation sequencing. The two separate mixes are amplified with multiple cycles of PCR amplification using both the universal primer and a pool of primers. The product of this amplification will be two separate pools of PCR products each of which has amplified one or other of the strands of the original polynucleotide, and will include all necessary sequences for compatibility with next generation sequencing.

(D) The modified target polynucleotide is combined with a universal primer, the primer is designed to hybridise to universal the sequence of the modifier target polynucleotide, with or with an additional 5' universal sequence. The modified target polynucleotide is then linear amplified by one or more rounds of amplification. The linear amplification product may be purified to remove no longer necessary reagents from the first PCR reaction. The linear amplification product is divided into two approximately equal aliquots. To each of these aliquots is added a universal primer, the primer is designed to hybridise to the universal sequence of the modifier target polynucleotide, with or with an additional 5' universal sequence. To each aliquot a different target specific primer or pool of target specific primers is added, each pool contains primers designed to amplify target regions of either the forward or reverse strand of the target polynucleotide. The target specific primers comprise a 3' target specific sequence with or without a 5' universal sequence. The two separate mixes are amplified with multiple cycles of PCR amplification using both the universal primer and a pool of primers. The product of this amplification will be two separate pools of PCR products each of which has amplified one or other of the strands of the original polynucleotide, with or without '3 and 5' universal sequences. The first amplification product may be purified to remove no longer necessary reagents from the first PCR reaction. Each of the two separate pools of PCR products are combined with a second, nested universal primer or the universal primer used in the first amplification, the 3' of this primer is designed to hybridise to universal sequence of the first PCR product and has a 5' tail containing sequences necessary for next generation sequencing, and a different nested target specific primer or pool of nested target specific primers which comprise a 3' target specific portion with a 5' universal portion containing sequences necessary for next generation sequencing. The two separate mixes are amplified with multiple cycles of PCR amplification using both the universal primer and a pool of primers. The product of this amplification will be two separate pools of PCR products each of which has amplified one or other of the strands of the original polynucleotide, and will include all necessary sequences for compatibility with next generation sequencing.

(E) The modified target polynucleotides are combined with a universal primer, the primer is designed to hybridise to the universal sequence of the modifier target polynucleotide, with or without an additional 5' universal sequence, a target specific primer or pool of target specific primers is added, the primers are designed to amplify the forward, or reverse strand of the target polynucleotide. The target specific primers comprise a 3' target specific sequence with or without a 5' universal sequence. The mix is amplified with multiple cycles of PCR amplification using both the universal primer and a target specific primer(s). The product of this amplification is a pool of PCR products which has amplified one or other of the strands of the original polynucleotide, with or without '3 and 5' universal sequences. The first amplification product is purified to remove all unused single strand primer. The purified first amplification product is combined with a universal primer, the primer is designed to hybridise to the universal sequence of the modifier target polynucleotide, with or without an additional 5' universal sequence, a target specific primer or pool of target specific primers is added, the target specific primer(s) are designed to amplify the forward, or reverse strand of the target polynucleotide which was not targeted in the first amplification reaction. If forward strand was targeted in the first reaction, then reverse is targeted in the second. The target specific primers comprise a 3' target specific sequence with or without a 5' universal sequence. The mix is amplified with multiple cycles of PCR amplification using both the universal primer and a target specific primer(s). The second amplification product is purified to remove all unused primers. The second amplification product is divided into two approximately equal aliquots. To each of these aliquots is added a second universal primer, the 3' of this primer is designed to hybridise to the universal sequence of the modifier target polynucleotide and has a 5' tail containing sequences necessary for next generation sequencing. To each aliquot a different target specific nested primer or pool of target specific nested primers is added, the primers are designed to amplify either the forward or reverse strand of the target polynucleotide. The target specific primers comprise a 3' target specific portion with a 5' universal portion containing sequences necessary for next generation sequencing. The two separate mixes are amplified with multiple cycles of PCR amplification using both the universal primer and a target specific primer(s). The product of this amplification will be two separate pools of PCR products each of which has amplified one or other of the strands of the original polynucleotide, and will include all necessary sequences for compatibility with next generation sequencing.

(F) The modified target polynucleotides are combined with a universal primer, the primer is designed to hybridise to the universal sequence of the modifier target polynucleotide, with an additional 5' universal sequence, a target specific primer or pool of target specific primers is added, the primers are designed to amplify the forward, or reverse strand of the target polynucleotide. The target specific primers comprise a 3' target specific sequence with a 5' universal sequence. The mix is amplified with multiple cycles of PCR amplification using both the universal primer and a target specific primer(s). The product of this amplification will be a pool of PCR products each which has amplified one or other of the strands of the original polynucleotide, with a 5' and 3' universal sequence. The first amplification product is purified to remove all unused primers. The purified first amplification product is combined with a universal primer, the primer is designed to hybridise to the universal sequence of the modifier target polynucleotide, with an additional 5' universal sequence, a target specific primer or pool of target specific primers is added, the target specific primer(s) are designed to amplify the forward, or reverse strand of the target polynucleotide whichever was not targeted in the first amplification reaction. If forward strand was targeted in the first reaction, then reverse is targeted in the second. The target specific primers comprise a 3' target specific sequence with a 5' universal sequence. The mix is amplified with multiple cycles of PCR amplification using both the universal primer and a target specific primer(s). The second amplification product is purified to remove all unused primers. The second amplification product is mixed with two universal primers, the 3' of the primers are designed to hybridise to the universal sequences at the 3' and 5' of the amplification products and have a 5' tail containing sequences necessary for next generation sequencing. The two mix is amplified with multiple cycles of PCR amplification using both universal primers. The product of this amplification will be a pool of PCR products each of which have amplified both strands of the original polynucleotide independently, and will include all necessary sequences for compatibility with next generation sequencing.

Figure 17:
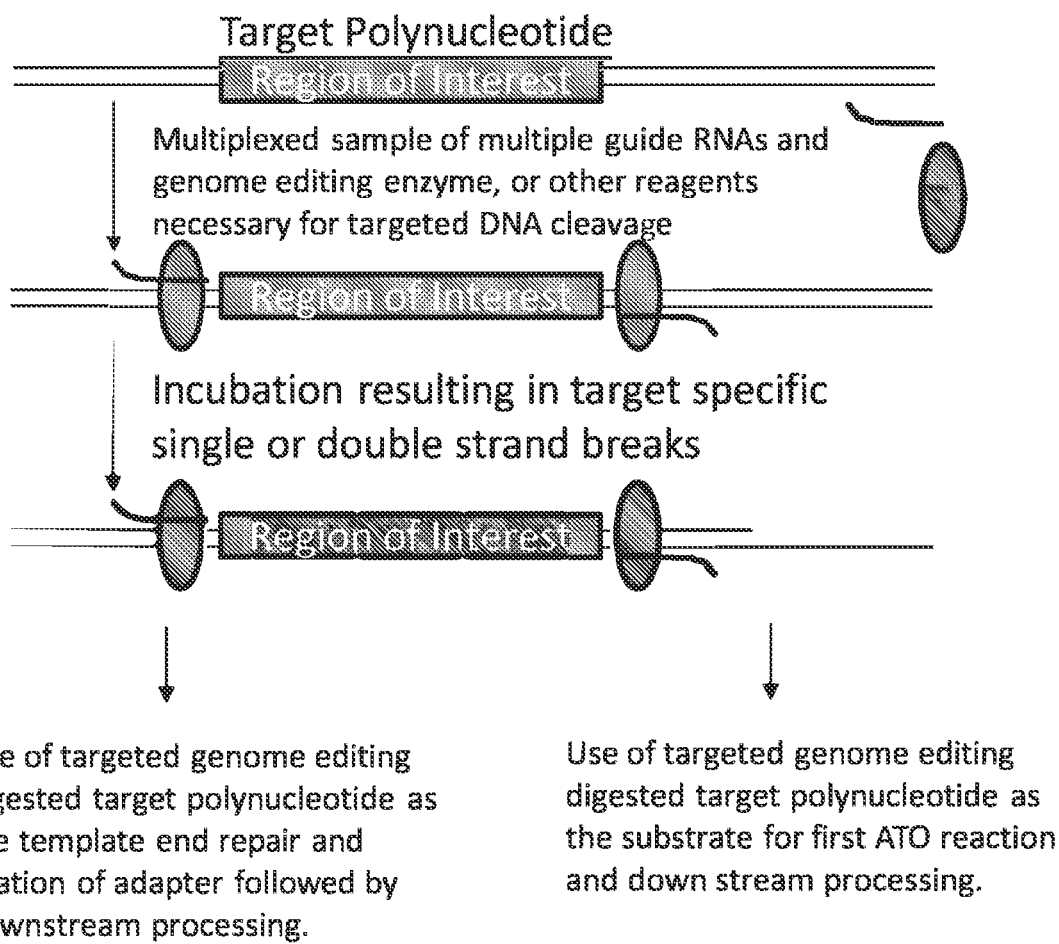

FIG. 17 depicts a schematic of an illustrative embodiment. A DNA target polynucleotide is shown. The process of enzymatic fragmentation using nucleases, or physical shearing of DNA by sonication, or by the use of a transposase, can be replaced by individual or multiplexed targeting of genome editing tools, such as a Type I, Type II, Type III, or combinations thereof of Cas genes and CRISPR subtypes of enzymes. As an example, CRISPR/Cas9 enzymes are incubated with DNA and a mixture of one or more guide RNAs. This results in an association of the DNA, CRISPR/Cas9 enzyme, and guide RNA, whereby the guide RNA targets the double or single strand cleavage of the DNA. The targeted fragmented DNA can then be purified and used in any subsequent downstream processes, such as a first ATO reaction.

Figure 18:
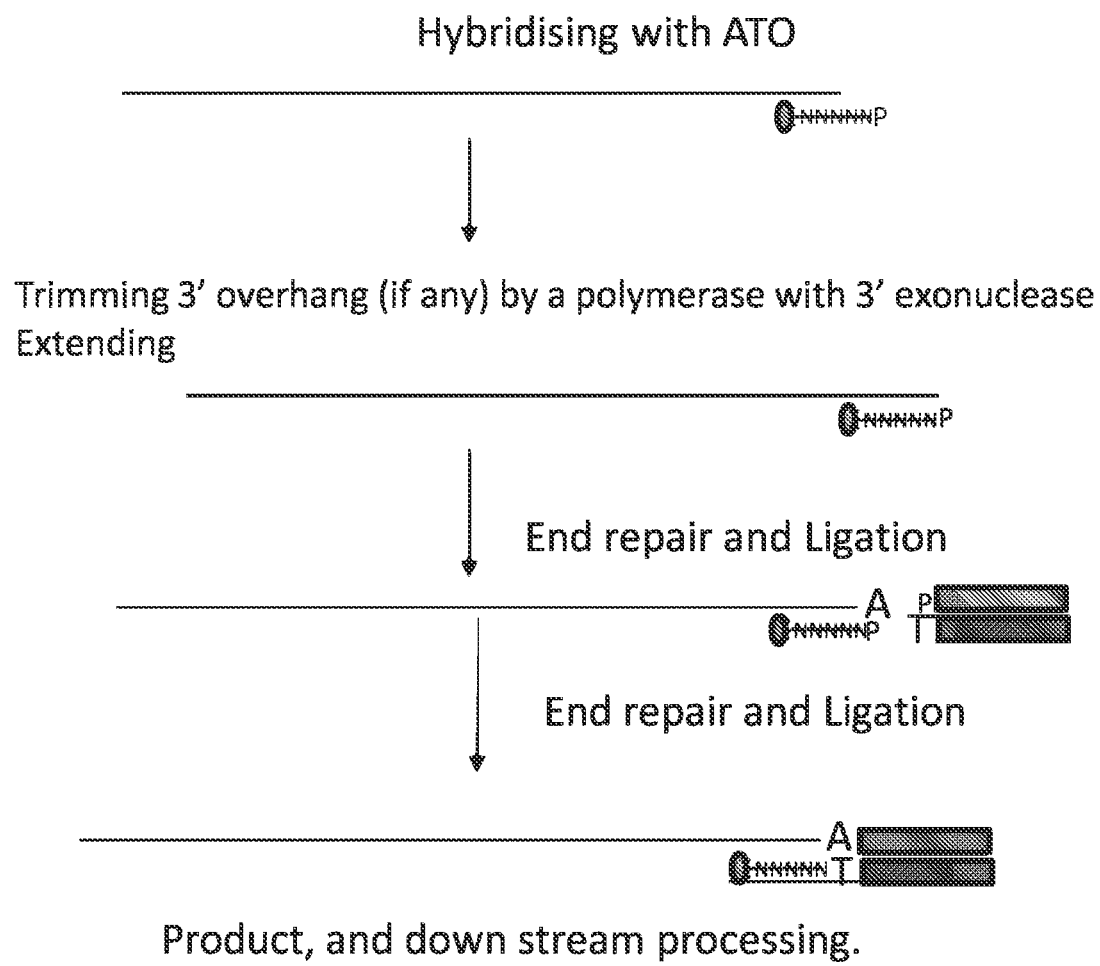

FIG. 18 depicts a schematic of an illustrative embodiment. A target polynucleotide (PCR products, or DNA, or RNA, or any mixture thereof) may be double-stranded, only one of two strands is shown (forward strand). In the step (i), ATO molecules are hybridised to single-stranded target polynucleotide sequences at one or more locations. The 3' ends of the target polynucleotide hybridises to the 3' random sequence portion of ATO, is trimmed if any 3' overhang is present, and is extended using ATO as template. The extension generates a modified target polynucleotide, which comprises a random sequence as UID. Following step (i), the ATOs are digested or removed by affinity capture. In some embodiment, the ATO is not digested or removed. In the step (ii) the target polynucleotide undergoes an end repair process followed by ligation with double strand adaptor. The product of this ligation reaction will be a modified target polynucleotide with contains a short 5' ligated sequence, and a longer universal '3 ligated sequence. This can then be used in downstream processes.

Figure 19:
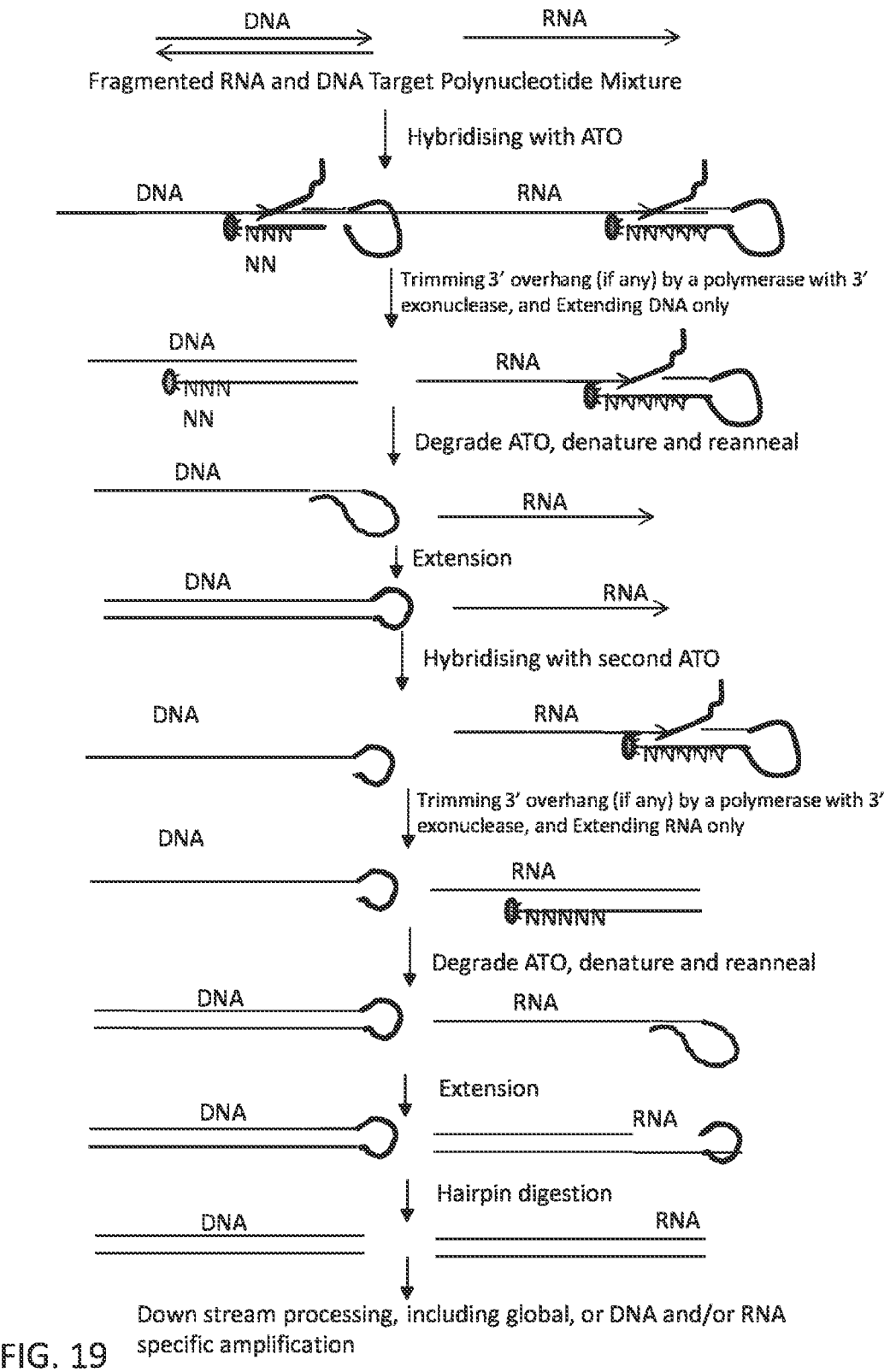

FIG. 19 depicts a schematic of an illustrative embodiment. A target polynucleotide (PCR products, or DNA, or RNA, or any mixture thereof) may be double-stranded, only one of two strands is shown (forward strand). The depiction takes advantage of the ability of polymerases to only use DNA, and not RNA, as a primer for extension of the polynucleotide. The first round the ATO molecules are hybridised to single-stranded target polynucleotide sequences at one or more locations. The 3' ends of the target polynucleotide hybridises to the 3' random sequence portion of ATO, is trimmed if any 3' overhang is present, and only the DNA is extended using an ATO as template and a polymerase unable to use RNA primers. The ATOs are digested or removed by affinity capture. In some embodiment, the ATO is not digested or removed. The 3' end of the modified target DNA polynucleotide is allowed to form a small hairpin by annealing to itself, the 3' end then acts as a primer which once extended will generate the first complementary strand. The double strand DNA, with a hairpin will act to preferentially allow the duplex to reform during the second round of ATO hybridising. The 3' ends of the target RNA polynucleotide hybridises to the 3' random sequence portion of ATO, and is extended using an ATO as template and a polymerase. The 3' end of the modified target RNA polynucleotide is allowed to form a small hairpin by annealing to itself, the 3' end then acts as a primer which once extended will generate the first complementary strand. The hairpins can then be digested. The resultant DNA:DNA and RNA:DNA hybrids can then form the template for further downstream processing. Such as generating a DNA, or RNA, or DNA+RNA sequencing library by selectively amplifying DNA and/or RNA.

The following passages are provided as clauses and are not to be considered as claims.

According to a first aspect, the present invention provides:

1. A removable template oligonucleotide (RTO) for generating a library of polynucleotides comprising:
   (a) a 3' random sequence;
   (b) the 3' end is attached with a blocker moiety, which makes RTO unextendible;
   (c) a universal sequence, 5' to the random sequence; and
   (b) nucleotide sequence/modification (NSM) recognisable by an agent,
   wherein RTO serves as a template, does not incorporate into a reaction product and is destroyed/removed after a reaction,
   wherein the NSM facilitates removal of RTO.
2. The removable template oligonucleotide of Clause 1, wherein the NSM is uracil nucleotide,
   wherein uracil nucleotides are incorporated into the RTO during oligo synthesis in the place of thymine nucleotides; wherein the agent is uracil-DNA glycosylase (UNG), which is capable of destroying/removing the RTO after the reaction finishes.
3. The removable template oligonucleotide of Clause 1, wherein the NSM is ribonucleotide,
   wherein ribonucleotides are incorporated during oligo synthesis into the RTO in the place of any nucleotides or all nucleotides; wherein the agent is RNase, which is capable of destroying/removing the RTO after the reaction finishes.
4. The removable template oligonucleotide of Clause 1, wherein the NSM is restriction enzyme recognising sequence, which is located in the universal sequence; wherein the agent is restriction enzyme, which is capable of destroying/removing the RTO after reaction finishes.
5. The removable template oligonucleotide of Clause 1, wherein the NSM is an affinity binding moiety, which is attached at any point of the RTO; wherein the agent is a protein or antibody, which is capable of removing the RTO after the reaction finishes.
6. The removable template oligonucleotide of Clause 5, wherein the affinity binding moiety is biotin; wherein the agent is avidin.
7. The removable template oligonucleotide of any one of Clauses 1-6, wherein the RTO comprises additional unique identification (UID) sequence located in the universal sequence.
8. The removable template oligonucleotide of any one of Clauses 1-7, wherein the RTO comprises a portion which forms stem loop structure.
9. A method for generating a library of polynucleotides comprising:

(i) generating a modified target polynucleotide using a target polynucleotide from a sample as a primer and a removable template oligonucleotide (RTO) of any one of Clauses 1-8 as a template;
(ii) removing the RTO; and
(iii) generating a first complement sequence (CS) of the modified target polynucleotide using a first primer, the first primer comprising the universal sequence,
wherein generating comprise extending primer is hybridised to a template by a polymerase.

10. The method of Clause 9, further comprising: generating a modified first CS using the first complement sequence as a primer and a second removable template oligonucleotide (RTO) of any one of Clauses 1-8 as a template.

11. The method of Clause 9 or 10, further comprising: extending a second primer hybridized to the first CS or modified first CS, thereby forming a second CS, wherein the second primer comprises a target-specific portion or universal sequence, or both 3' target specific and 5' universal sequence.

12. The method of Clause 11, wherein when a target polynucleotide in a sample is double stranded, extending a second primer hybridized to the first CS comprises dividing the first CS into two separate reactions, where the first reaction comprises a target-specific second primer complementary to the first strand of a target sequence, and the second reaction comprises a target-specific second primer complementary to the second strand of the target sequence,
wherein the first strand and second strand of the target sequence are complementary.

13. The method of Clause 11 or 12, wherein extending comprises linear amplification using first primer or second primer.

14. The method of Clause 11 or 12, wherein extending comprises exponential amplification using the first primer and second primer.

15. The method of any one of Clauses 9-14, wherein the first primer comprises a sample barcode (SBC) sequence and additional universal sequence compatible with a NGS platform.

16. The method of any one of Clauses 9-15, wherein when the second primer is a target-specific primer, after linear or exponential amplification using the second primer, a nested target-specific third primer is used for a further amplification.

17. A method of accurately determining the sequence of a target polynucleotide comprising:
(i) sequencing at least one of the amplified second CSs of any one of Clauses 9-16;
(ii) aligning at least two sequences containing the same UID from (i) and/or aligning same target sequences of two reactions, wherein each reaction generates sequence information of one strand or complementary strand of a duplex target sequence; and
(iii) determining a consensus sequence and/or identical variant sequence of two reactions based on (ii), wherein the consensus sequence and/or variant sequence accurately represents the target polynucleotide sequence.

18. A kit for generating a library of polynucleotides comprising a removable template oligonucleotide (RTO) of any one of Clauses 1-8, and primers compatible with a NGS platform.

According to a second aspect, the present invention provides:

1. An adaptor template oligonucleotide (ATO) for generating a library of polynucleotides comprising:
(a) a 3' random sequence;
(b) the 3' end is attached with a blocker moiety, which makes the ATO non-extendible;
(c) a universal sequence, 5' to the random sequence; and
(b) nucleotide sequence/modifications (NSM), which makes the ATO non-interfering and non-competing;
wherein the ATO serves as a template to direct a first extension reaction and does not incorporate into the reaction product.

2. The adaptor template oligonucleotide of Clause 1, wherein the NSM is a non-canonical nucleotide (non-dA, Non-dG, Non-dT, non-dC), which is a naturally occurring or artificial nucleotide.

3. The adaptor template oligonucleotide of Clause 2, wherein the non-canonical nucleotide is a universal nucleotide.

4. The adaptor template oligonucleotide of Clause 2, wherein the non-canonical nucleotide comprises an inosine base, wherein the inosine is used to replace the usual guanine position in the sequence of the ATO, wherein the deoxyInosine preferentially directs incorporation of dC in the growing nascent strand by DNA polymerase.

5. The adaptor template oligonucleotide of Clause 1, wherein the NSM is recognisable by an agent, which facilitates digestion/removal of the ATO.

6. The adaptor template oligonucleotide of Clause 5, wherein the NSM is uracil nucleotide,
wherein uracil nucleotides are incorporated into the ATO during oligo synthesis in the place of thymine nucleotides; wherein the agent is uracil-DNA glycosylase (UNG), which is capable of destroying/removing the ATO after the first extension reaction finishes.

7. The adaptor template oligonucleotide of Clause 5, wherein the NSM is ribonucleotide,
wherein ribonucleotides are incorporated during oligo synthesis into the ATO in the place of any nucleotides or all nucleotides; wherein the agent is RNase, which is capable of destroying/removing the ATO after the first extension reaction finishes.

8. The adaptor template oligonucleotide of Clause 5, wherein the NSM is a restriction enzyme recognising sequence which is located in the universal sequence; wherein the agent is a restriction enzyme which is capable of destroying/removing the ATO after the first extension reaction finishes.

9. The adaptor template oligonucleotide of Clause 5, wherein the NSM is an affinity binding moiety, which is attached at any point of the ATO; wherein the agent is a protein or antibody, which is capable of removing the ATO after the first extension reaction finishes.

10. The adaptor template oligonucleotide of Clause 9, wherein the affinity binding moiety is biotin; wherein the agent is avidin.

11. The adaptor template oligonucleotide of any one of Clauses 1-10, wherein the ATO comprises an additional unique identification (UID) sequence located in the universal sequence.

12. The adaptor template oligonucleotide of any one of Clauses 1-10, wherein the ATO comprises a portion which forms a stem loop structure.

13. A method for generating a library of polynucleotides comprising:
(i) generating a modified target polynucleotide by using a target polynucleotide from a sample as a primer and an adaptor template oligonucleotide (ATO) of any one of Clauses 1-12 as template; and (ii) generating a first complement sequence (CS) of the modified target polynucleotide using a first primer, which comprises the universal sequence, and the modified target polynucleotide as template, wherein generating comprise extending primer hybridised to a template by a polymerase.

14. The method of Clause 13, further comprising: generating a modified first CS by using the first complement sequence as a primer and a second adaptor template oligonucleotide (ATO) of any one of Clauses 1-12 as template and extending the first CS on the ATO template.

15. The method of Clause 13, wherein the step (i) further comprises removing the ATO.

16. The method of Clause 13, 14 or 15, further comprising: extending a second primer hybridized to the first CS or modified first CS, thereby forming a second CS, wherein the second primer comprises a target-specific portion or universal sequence, or both 3' target specific and 5' universal sequence.

17. The method of Clause 16, wherein when the target polynucleotides in a sample are double stranded, extending a second primer hybridized to the first CS comprises dividing the first CS into two separate reactions, where the first reaction comprises a target-specific second primer complementary to the first strand of a target sequence, and the second reaction comprises a target-specific second primer complementary to the second strand of the target sequence, wherein the first strand and second strand of the target sequence are complementary.

18. The method of Clause 13, 14, 16 or 17, wherein extending comprises linear amplification.

19. The method of Clause 16, wherein extending comprises exponential amplification using first primer and second primer.

20. The method of any one of Clauses 13-19, wherein the first primer comprises a sample barcode (SBC) sequence and additional universal sequence compatible with a NGS platform.

21. The method of any one of Clauses 13-19, wherein when the second primer is a target-specific primer, after linear or exponential amplification using the second primer, a nested target-specific third primer is used for a further amplification.

22. A method of accurately determining the sequence of a target polynucleotide comprising:

(i) sequencing at least one of the amplified second CSs of any one of Clauses 13-21;

(ii) aligning at least two sequences containing the same UID from (i) and/or aligning the same target sequences of two reactions, wherein each reaction generates sequence information of one strand or a complementary strand of a duplex target sequence; and (iii) determining a consensus sequence and/or identical variant sequence of two reactions based on (ii), wherein the consensus sequence and/or variant sequence accurately represents the target polynucleotide sequence.

23. A kit for generating a library of polynucleotides comprising an adaptor template oligonucleotide (ATO) of any one of Clauses 1-12, and primers compatible with a NGS platform.

According to a third aspect, the invention provides:

1. An adaptor template oligonucleotide (ATO) for generating a library of polynucleotides comprising:

(a) a 3' random sequence;

(b) the 3' end is attached with a blocker moiety, which renders the ATO non-extendible;

(c) a universal sequence, 5' to the random sequence; and (b) nucleotide sequence/modifications (NSM);

wherein the ATO serves as a template to direct a first reaction and all or part of the ATO does not incorporate into the first reaction product, wherein the NSM renders the ATO non-interfering and non-competing in the reaction after the first reaction.

2. The adaptor template oligonucleotide of Clause 1, wherein the NSM is a non-canonical nucleotide (non-dA, Non-dG, Non-dT, non-dC), which is a naturally occurring or artificial nucleotide.

3. The adaptor template oligonucleotide of Clause 2, wherein the non-canonical nucleotide is a universal nucleotide.

4. The adaptor template oligonucleotide of Clause 2, wherein the non-canonical nucleotide comprises an inosine base, wherein the inosine is used to replace a guanine position in the sequence of the ATO, wherein the deoxyInosine preferentially directs incorporation of dC in the growing nascent strand by a DNA polymerase.

5. The adaptor template oligonucleotide of Clause 1, wherein the NSM is recognisable by an agent, which facilitates digestion/removal of the ATO.

6. The adaptor template oligonucleotide of Clause 5, wherein the NSM is a uracil nucleotide, wherein the uracil nucleotides are incorporated into the ATO during oligo synthesis in the place of thymine nucleotides; wherein the agent is uracil-DNA glycosylase (UNG), which is capable of destroying/removing the ATO after the first extension reaction finishes.

7. The adaptor template oligonucleotide of Clause 5, wherein the NSM is ribonucleotide, wherein ribonucleotides are incorporated during oligo synthesis into the ATO in the place of any nucleotides or all nucleotides; wherein the agent is RNase, which is capable of destroying/removing the ATO after the first extension reaction finishes.

8. The adaptor template oligonucleotide of Clause 5, wherein the NSM is a restriction enzyme recognising sequence, which is located in the universal sequence; wherein the agent is a restriction enzyme, which is capable of destroying/removing the ATO after the first extension reaction finishes.

9. The adaptor template oligonucleotide of Clause 5, wherein the NSM is an affinity binding moiety, which is attached at any point of the ATO; wherein the agent is a protein or antibody, which is capable of removing the ATO after the first extension reaction finishes.

10. The adaptor template oligonucleotide of Clause 9, wherein the affinity binding moiety is biotin; wherein the agent is avidin.

11. The adaptor template oligonucleotide of any one of Clauses 1-10, wherein the ATO comprises an additional unique identification (UID) sequence located in the universal sequence.

12. The adaptor template oligonucleotide of Clause 1, wherein the ATO comprises a 5' stem portion sequence which is complementary to a part of the universal sequence, which is capable of forming a stem-loop structure.

13. The adaptor template oligonucleotide of Clause 12, wherein the loop part comprises a non-copiable linkage.

14. The adaptor template oligonucleotide of Clause 13, wherein the non-copiable linkage is a C3 Spacer phosphoramidite, or a triethylene glycol spacer, or an 18-atom hexa-ethyleneglycol spacer, or 1',2'-Dideoxyribose (dSpacer).
15. The adaptor template oligonucleotide of Clause 12, wherein the loop part comprises nucleotides which can be digested.
16. The adaptor template oligonucleotide of Clause 12, wherein the 5' end of the stem portion sequence comprises a phosphate group.
17. The adaptor template oligonucleotide of Clause 1, wherein the ATO comprises an upper separate strand which is complementary to a part of the universal sequence, which is capable of forming a partially double-stranded structure.
18. The adaptor template oligonucleotide of Clause 17, wherein the upper separate strand comprises nucleotides which can be digested.
19. The adaptor template oligonucleotide of Clause 17, wherein the 5' end of the upper separate strand comprises a phosphate group.
20. The adaptor template oligonucleotide of Clause 17, wherein the 3' end of the upper separate strand comprises a biotin.
21. A method for generating a library of polynucleotides comprising:
(i) generating a modified target polynucleotide by using a target polynucleotide from a sample hybridising to the 3' random sequence of the adaptor template oligonucleotide (ATO) of any one of Clauses 1-20 (first ATO) in an enzymatic first reaction which adds an adaptor sequence to the 3' end of the target polynucleotide; and
(ii) generating a first complement sequence (CS) of the modified target polynucleotide using a first primer, which comprises the universal sequence, and the modified target polynucleotide as a template, wherein the first primer is hybridised to the template and is extended by a polymerase.
22. The method of Clause 21, wherein the first reaction is a primer extension reaction, wherein the target polynucleotide serves as a primer and is extended on the ATO template by a DNA polymerase.
23. The method of Clause 22, wherein the DNA polymerase has strand displacement activity,
wherein during the extension the stem-loop structure is opened or the upper ATO strand is displaced.
24. The method of Clause 22, wherein the first reaction is an extension-ligation reaction, wherein a DNA polymerase extends the target and a DNA ligase ligates the extended target sequence to the 5' stem portion of the ATO or the upper strand of the ATO.
25. The method of Clause 22, wherein the first reaction is a ligation reaction, wherein a DNA ligase ligates the target sequence to the 5' stem portion of the ATO or the upper strand of the ATO.
26. The method of Clause 21, further comprising, after the first reaction, digesting part of the ATO or removing part of the ATO by affinity capturing.
27. The method of Clause 21, further comprising generating a modified first CS by using the first CS hybridising to the 3' random sequence of the second ATO of any one of Clauses 1-20 in an enzymatic reaction which adds an adaptor sequence to the 3' end of the first CS, wherein the second ATO comprises a different 5' universal sequence compared to the first ATO.
28. The method of Clause 21, further comprising generating a modified first CS by ligating double-stranded adaptors into the products of step (ii).
29. The method of Clause 21, 27 or 28, further comprising extending a second primer hybridized to the first CS or modified first CS, thereby forming a second CS, wherein the second primer comprises a target-specific portion or universal sequence, or both 3' target specific and 5' universal sequence.
30. The method of Clause 29, wherein when the target polynucleotides in a sample are double-stranded and the second primers are target specific primers, extending the second primer hybridized to the first CS comprises dividing the first CS into two separate reactions, where the forward reaction comprises a target-specific second primer complementary to the forward strand of a target sequence, and the reverse reaction comprises a target-specific second primer complementary to the reverse strand of the target sequence, wherein the forward strand and reverse strand of the target sequence are complementary.
31. The method of any one of Clauses 21-30, wherein generating the first CS comprises linear amplification with 1-30 cycles.
32. The method of any one of Clauses 21-31, wherein generating the first CS comprises a reverse transcription reaction using reverse transcriptase if the target is RNA.
33. The method of any one of Clauses 21-32, wherein extending comprises exponential amplification using first primer and second primer.
34. The method of any one of Clauses 21-33, wherein when the second primer is a target-specific primer, and after linear or exponential amplification using the second primer, a nested target-specific third primer is used for a further amplification.
35. The method of any one of Clauses 21-34, wherein the first primer or fourth primer which targets the universal adaptor sequence comprises a sample barcode (SBC) sequence and an additional universal sequence compatible with a NGS platform.
36. A method of accurately determining the sequence of a target polynucleotide comprising:
(i) sequencing at least one of the amplified first CSs or second CSs of any one of Clauses 21-35;
(ii) aligning at least two sequences containing the same UID from (i) and/or aligning same target sequences of two reactions, where each reaction generates sequence information of one strand or a complementary strand of a duplex target sequence; and
(iii) determining a consensus sequence and/or identical variant sequence of two reactions based on (ii), wherein the consensus sequence and/or variant sequence accurately represents the target polynucleotide sequence.
37. A kit for generating a library of polynucleotides comprising an adaptor template oligonucleotide (ATO) of any one of Clauses 1-36, and primers compatible with a NGS platform.

According to a fourth aspect, the invention provides:
1. An adaptor template oligonucleotide (ATO) for extending polynucleotides comprising:
(a) a 3' random sequence;
(b) the 3' end is attached with a blocker, which renders ATO non-extendible; and
(c) a universal sequence, 5' to the random sequence;
wherein ATO serves as a template to direct a extension reaction by a polymerase.

2. The adaptor template oligonucleotide of Clause 1, further comprising moiety(s) which renders ATO degradable or non-interfering and non-competing in the reactions following the extension reaction, wherein the moiety is recognisable by an agent, which facilitates digestion/removal of ATO.
3. The adaptor template oligonucleotide of Clause 2, wherein the moieties are uracil nucleotides,
wherein the agent comprises a dU-glycosylase, which is capable of digesting/removing the ATO following the first extension reaction.
4. The adaptor template oligonucleotide of Clause 2, wherein the moieties are ribonucleotides,
wherein ribonucleotides are incorporated during oligo synthesis into the ATO in place of any nucleotides, or all nucleotides; wherein the agent is a ribonuclease, which is capable of digestion/removing the ATO following the first extension reaction.
5. The adaptor template oligonucleotide of Clause 1, wherein the ATO is RNA oligo.
6. The adaptor template oligonucleotide of Clause 1, wherein the ATO is DNA oligo.
7. The adaptor template oligonucleotide of Clause 1, wherein the ATO is a combination of DNA and RNA oligo.
8. The adaptor template oligonucleotide of Clause 2, wherein the moiety is restriction enzyme recognising sequence, wherein the agent is restriction enzyme.
9. The adaptor template oligonucleotide of Clause 1, wherein the universal sequence comprises a sequence capable of acting as an RNA polymerase promoter.
10. The adaptor template oligonucleotide of Clause 9, wherein the RNA polymerase is T7 RNA polymerase, T3 RNA polymerase, or SP6 RNA polymerase.
11. The adaptor template oligonucleotide of Clause 9, wherein the universal sequence comprises a 5' RNA polymerase promoter sequence, and a priming site, which is located at the 3' of the RNA polymerase promotor sequence.
12. The adaptor template oligonucleotide of Clause 1, wherein the universal sequence is double-stranded or partially double stranded.
13. The adaptor template oligonucleotide of Clause 12, wherein the ATO comprises a 5' stem portion sequence which is complementary or partially complementary to part of or all of the universal sequence, which are capable of forming a stem-loop structure.
14. The adaptor template oligonucleotide of Clause 13, wherein the ATO comprises in 5' to 3' order: 5' stem portion, an RNA polymerase sequence, priming site sequence and 3' random/degenerated sequence.
15. The adaptor template oligonucleotide of Clause 13, wherein the RNA polymerase sequence is located in the loop part.
16. The adaptor template oligonucleotide of Clause 13, wherein the loop part comprises a non-copiable linkage.
17. The adaptor template oligonucleotide of Clause 13, wherein the loop part does not comprise a non-copiable linkage.
18. The adaptor template oligonucleotide of Clause 13, wherein if the 5' of the stem portion comprises an additional sequence, a non-copiable linkage is present between the stem portion and the additional sequence.
19. The adaptor template oligonucleotide of Clause 13, wherein the 5' stem portion comprises a non-copiable linkage.
20. The adaptor template oligonucleotide of Clauses 13-19, wherein the non-copiable linkage is C3 Spacer phosphoramidite, or a triethylene glycol spacer, or an 18-atom hexa-ethyleneglycol spacer, or 1',2'-Dideoxyribose (dSpacer).
21. The adaptor template oligonucleotide of Clause 13, wherein the double-stranded stem part comprises a non-complementary region, wherein the non-complementary region in the universal sequence strand comprises a random sequence.
22. The adaptor template oligonucleotide of Clause 13, wherein the stem portion forms two or more split sections separated by one or more non-copiable linkage.
23. The adaptor template oligonucleotide of Clause 13, wherein the stem portion forms two or more split sections separated by one or a region of mismatched base pairs.
24. The adaptor template oligonucleotide of Clause 12, wherein the ATO comprises an upper separate strand which is complementary or partially complementary to the universal sequence.
25. The adaptor template oligonucleotide of Clause 24, wherein the 5' end of the upper separate strand comprises a phosphate group.
26. The adaptor template oligonucleotide of Clause 1, wherein the ATO further comprises an affinity binding moiety, which is attached in any place of ATO.
27. The adaptor template oligonucleotide of Clause 26, wherein the affinity binding moiety is biotin.
28. The adaptor template oligonucleotide of any one of the preceding Clauses, wherein the 5' end comprises a phosphate group.
29. The adaptor template oligonucleotide of any one of the preceding Clauses, wherein the universal sequence comprises a random sequence which acts as an additional unique identification (UID) sequence.
30. The adaptor template oligonucleotide of Clause 29, wherein the ATO comprises an additional UID within the loop section.
31. The adaptor template oligonucleotide of Clause 29, wherein the ATO comprises an additional UID within the stem section.
32. The adaptor template oligonucleotide of Clause 1, wherein the ATO sequence comprises a non-canonical nucleotide (non-dA, non-dG, non-dT, non-dC), which is naturally occurring or an artificial nucleotide.
33. The adaptor template oligonucleotide of Clause 32, wherein the non-canonical nucleotide is a universal nucleotide.
34. The adaptor template oligonucleotide of Clause 32, wherein the non-canonical nucleotide comprises an inosine base.
35. The adaptor template oligonucleotide of Clause 32, wherein the 3' random sequence comprises non-canonical nucleotides.
36. The adaptor template oligonucleotide of Clause 32, wherein the universal sequence comprises non-canonical nucleotides.
37. The adaptor template oligonucleotide of Clause 1, wherein the 3' end comprises modified nucleotide(s) or linkages which make the ATO resistant to 3' exonuclease activity of a DNA polymerase.
38. The adaptor template oligonucleotide of Clause 37, wherein the modified linkages are phosphorothioate linkages.

39. The adaptor template oligonucleotide of Clause 1, further comprising a specific sequence 3' of the random sequence, wherein the specific sequence is capable of hybridising to a specific sequence of the polynucleotide, and part of the 3' random/degenerated sequence serves as a template on which the polynucleotide is extended by a polymerase.
40. A composition comprising at least one nucleic acid polymerase and an adaptor template oligonucleotide (ATO) of any one of the preceding Clauses.
41. The composition of Clause 40, wherein nucleic acid polymerase is a DNA polymerase.
42. The composition of Clause 41, wherein the DNA polymerase has strand-displacement activity.
43. The composition of Clause 41, wherein the DNA polymerase has 3' to 5' exonuclease activity.
44. The composition of Clause 41, wherein the DNA polymerase is a template-dependent polymerase and is not a template-independent polymerase.
45. A method for extending target polynucleotides comprising:
(i) generating a modified target polynucleotide by incubating target polynucleotides with the composition of any of the preceding Clauses, wherein the 3' end of the target polynucleotide hybridises to the 3' random sequence of an adaptor template oligonucleotide (first ATO) in a enzymatic first ATO reaction, in which the 3' end of the target polynucleotide is extended using ATO as template, wherein if a 3' overhanging end is present, the 3' end of the target polynucleotide is trimmed before extension takes place.
46. The method of Clause 45, further comprising (ii) generating a first complement sequence (CS) of the modified target polynucleotide.
47. The method of Clause 46, wherein generating the first CS comprises extension using a first primer, and using the modified target polynucleotide as template, wherein the first primer is hybridised to the template and is extended by a polymerase.
48. The method of Clause 46, wherein generating the first CS comprises in vitro transcription using an RNA polymerase from the double-stranded promotor region in the modified target polynucleotide generated by extending on ATO containing an RNA polymerase promotor.
49. The method of Clause 46, wherein generating the first CS comprises heat denaturing the modified target polynucleotide, annealing the 3' stem-loop structure of the modified target polynucleotide and self-priming to extend to form the first CS.
50. The method of Clause 46, wherein generating the first CS comprises target specific primer annealing to the modified target polynucleotide and extension by a polymerase.
51. The method of any one of Clauses 46-50, further comprising digesting the ATO before or after generating a first complement sequence (CS) of the modified target polynucleotide.
52. The method of any one of Clauses 46-51, further comprising affinity capturing before or after generating a first complement sequence (CS) of the modified target polynucleotide.
53. The method of Clause 45, wherein the first ATO reaction comprises extension and ligation, wherein a DNA polymerase extends the 3' end of the target, and a DNA ligase ligates the extended target sequence to the 5' stem portion of the ATO or upper separate strand of the ATO.
54. The method of Clause 46, further comprising generating a modified first CS by incubating the first CS with the composition of any of the Clauses 35-39, wherein the 3' end of the first CS hybridises to the 3' random sequence of an adaptor template oligonucleotide (second ATO) in an enzymatic second ATO reaction, in which the 3' end of the first CS is extended using the ATO as a template, wherein if a 3' overhang is present, the 3' end of the first CS is trimmed before extension takes place, wherein the second ATO comprises a different 5' universal sequence of the first ATO.
55. The method of Clause 46, further comprising generating a modified first CS by ligating adaptors into the products of step (ii).
56. The method of any one of Clauses 46-55, further comprising extending a second primer hybridized to the first CS or modified first CS, thereby forming a second CS, wherein the second primer comprises a target-specific portion or universal sequence, or both a 3' target specific and a 5' universal sequence.
57. The method of Clause 56, wherein when the target polynucleotides in a sample are double-stranded and second primers are target specific primers, extending the second primer hybridized to the first CS comprises dividing the first CS into two separate reactions, where the forward reaction comprises a target-specific second primer complementary to the forward strand of a target sequence and the reverse reaction comprises a target-specific second primer complementary to reverse strand of the target sequence, wherein the forward strand and the reverse strand of the target sequence are complementary.
58. The method of Clause 47, wherein generating the first CS comprises linear amplification with 1-30 cycles or more.
59. The method of any one of Clauses 47 or 49, wherein generating the first CS comprises reverse transcription reaction using reverse transcriptase if the target is RNA.
60. The method of any one of Clauses 56-59, further comprising exponential amplification using a first primer and a second primer.
61. The method of any one of Clauses 56-60, wherein when the second primer is a target-specific primer, after linear or exponential amplification using the second primer, a nested target-specific third primer is used for a further amplification.
62. The method of any one of Clauses 56-61, wherein the first primer or third primer comprises a sample barcode (SBC) sequence and additional universal sequence compatible with a NGS platform.
63. The method of Clause 45, comprising fragmenting target polynucleotides before the first ATO reaction.
64. The method of Clause 63, wherein fragmenting said target polynucleotides comprises contacting double-stranded polynucleotides with transposase bound to transposon DNA, wherein the transposon DNA comprises a transposases binding site and universal sequence, wherein the transposases/transposon DNA complex bind to target locations on the double-stranded polynucleotide and cleave the double-stranded polynucleotides into a plurality of double-stranded fragments, with each double-stranded fragment having the transposon DNA bound to each 5' end of the double-stranded fragment.

65 The method of Clause 63, wherein said fragmenting comprises use of targeted fragmentation using genome editing tool.
66. The method of Clause 65, wherein said genome editing tool comprises clustered regularly interspaced short palindromic repeats and CRISPR-associated protein 9 enzyme (CRISPR/Cas9).
67. The method of Clause 63, wherein comprising heat denaturing the fragmented target polynucleotides before the first ATO reaction.
68. The method of Clause 64, wherein the transposase is Tn5 transposase.
69. The method of Clause 63, wherein said fragmenting and tagging target polynucleotides comprises contacting single-stranded polynucleotides with random primer which comprises a 5' universal sequence and a 3' random sequence, extending the random primer on the target polynucleotide to generate 5' tagged fragmented polynucleotides.
70. The method of Clause 45, wherein the target polynucleotide comprises a free 3' hydroxyl group.
71. The method of Clause 45, wherein the target polynucleotide is single-stranded DNA, or single-stranded RNA, or a combination of single-stranded RNA and single-stranded DNA.
72. A method for extending target polynucleotides comprising:
mixing the target polynucleotide with DNA polymerase, adaptor template oligonucleotide (ATO) comprising 3' random sequence which has the 3' end blocked and modified to be resistant to 3'exonuclease activity;
incubating the mixture under conditions that promote annealing, trimming the 3' overhang if present and extending to generate modified target polynucleotide; and optionally degrading the ATO.
73. A method for generating a sequencing library comprising:
mixing the target polynucleotides with DNA polymerase and adaptor template oligonucleotide (ATO) comprising a 3' random sequence which is blocked at the 3' end and modified to be resistant to 3'exonuclease activity;
incubating the mixture under conditions that promote annealing, trimming the 3' overhang if present and extending to generate modified target polynucleotide;
optionally degrading the ATO; and
amplifying the modified target polynucleotide using primers compatible with a NGS platform.
74. The method of Clause 73, comprising fragmenting the target polynucleotide prior to mixing.
75. The method of Clause 73, wherein the target polynucleotide is naturally occurring fragmented polynucleotide.
76. The method of Clause 75, wherein the naturally occurring fragmented polynucleotide is circulating cell free nucleic acid of plasma.
77. The method of Clause 74, wherein fragmenting said target polynucleotide comprises contacting double-stranded polynucleotides with transposase bound to transposon DNA, wherein the transposon DNA comprises a transposases binding site and a universal sequence, wherein the transposases/transposon DNA complex bind to target locations on the double-stranded polynucleotide and cleave the double-stranded polynucleotides into a plurality of double-stranded fragments, with each double-stranded fragment having the transposon DNA bound to each 5' end of the double-stranded fragment.
78. A method for generating a sequencing library comprising:
adding an adaptor sequence to a single-stranded target polynucleotide as defined in any one of Clauses of 45-69 by extending the single-stranded target polynucleotide on an ATO; and
amplifying the adaptor-tagged target polynucleotide using primers compatible with a NGS platform.
79. A kit comprising the composition of any of one of Clauses 1 to 44.
80. A kit for generating a library of polynucleotides comprising an adaptor template oligonucleotide (ATO) as defined in any one of Clauses 1-41, polymerase and primers compatible with a NGS platform.

EXAMPLES

Example 1

Using deoxyribonucleic acid (DNA) as the target polynucleotide for producing a Next Generation Sequencing Library (for example and without limitation, compatible with Illumina Next Generation Sequencers) using for example and without limitation, adaptor template oligo(s) with a stem-loop structure, wherein the loop comprises a chemical spacer (for example and without limitation, a C3 spacer, a C18 spacer).

Materials
  Target polynucleotide, human gDNA (BIO-35025)
  DNA fragmenting enzyme, KAPA Frag Kit (Roche, 7962517001)
  Adaptor template oligos (ATO), 1-014, 1-015, 1-016, 1-017, 1-018 (Table 1)
  TAQ DNA polymerase (NEB, M0273L)
  TAQ DNA polymerase buffer (NEB, M0273L)
  DNA Polymerase I, Large (Klenow) Fragment (NEB, M0210L)
  DNA Polymerase I, Large (Klenow) Fragment (NEB, M0212L)
  dNTPs (NEB, N0447s)
  USER® Enzyme (NEB, M5505S)
  Phusion® High-Fidelity DNA Polymerase (NEB, M0530S)
  Phusion buffer (NEB, M0530S)
  Primers, 2-001, 2-002, 2-003 (Table 2)
  Ammonium sulphate (SIGMA, A4418)
  Agencourt AMPure XP (Beckman Coulter, A63881)
  Bioanalyzer high sensitivity kit from Agilent (product ID 5067-4626)

Method
Annealing of Adaptor Template Oligo(s) to Deoxyribonucleic Acids

A suitable quantity of deoxyribonucleic acid (DNA), either fragmented or unfragmented, single or double strand, of any length, are mixed with a suitable quantity of Adaptor Template Oligo(s) (ATO(s); for example and without limitation an oligo which forms a hairpin, in a suitable buffer. In this example Human gDNA was fragmented using the Frag Kit generating fragmented DNA between 100-400 bp, as depicted in section (A) of FIG. 14. A total of 25 ng was mixed with 50 pmole of each of four ATOs (1-001, 1-002, 1-003, 1-004) for a total of 200 pmole of ATO, in $H_2O$ to a final volume of 15 ul. The mixture is heated at a suitable temperate, in this example 95° C., for a suitable time, in this example 2 minutes, or other temperatures or times which can result in denaturing of double strand nucleic acids to single strands. The nucleic acids and ATO(s) mixture are subsequently cooled, in this example to 4° C. for 2 minutes, or other suitable temperatures or times capable of promoting annealing between nucleic acids and ATO(s), as depicted in section (B) of FIG. 14.

Target Polynucleotide Extension by its Use as a Primer with the Adaptor Template Oligo(s) as a Template A suitable quantity of DNA polymerase(s), proof reading or not proof reading, with strand displacement or no strand displacement activity (for example and without limitation Bst polymerase, DNA Polymerase I, Large (Klenow) Fragment, Taq DNA polymerase, or Phusion), mixed with suitable buffer(s), and suitable dNTPs, is combined with the DNA-ATOs mixture. In this example a total of 2.5 units of Klenow and 2.5 units of TAQ DNA polymerase, 2 ul of 10×TAQ DNA polymerase buffer, and 10 nmole of each dNTP (dATP/dTTP/dCTP/dGTP), is combined with the DNA-ATO mixture to a final volume of 20 ul. To further promote target nucleic acid and ATO(s) annealing in the presence of DNA polymerase(s) and buffer(s) in this example the mixture is incubated below 25° C. for 30 minutes, or other suitable temperatures or times capable of promoting annealing between nucleic acids and ATO(s). To initiate extension of the target polynucleotides using the ATO sequence as a template in this example the incubation temperate is increased to 37° C. for 30 minutes, or other suitable temperatures capable of promoting DNA polymerase activity. The product is a modified target polynucleotide. As depicted in section (C) of FIG. 14.

Degradation of Adaptor Template Oligo(s)

Adaptor template oligo(s) are selectively degraded by the addition of a combination of, for example but not limited to, dU-glycosylase, and an apurinic/apyrimidinic endonuclease, in this example 2 units of USER enzyme, was added to the 20 ul modified target polynucleotide reaction mixture, followed by sequential incubations of, in this example, 37° C. for 30 minutes and then 25° C. for 15 minutes, or other suitable temperatures and times capable of promoting enzyme activity. The degraded ATO(s) can optionally be removed using any suitable purification method. As depicted in section (D) of FIG. 14.

One-Pass Extension or Linear Amplification of Modified Target Polynucleotide

The target polynucleotide extension product (modified target polynucleotide), purified or un-purified, is combined with a primer complementary to the conserved (universal) sequence now present on the 3' of the target DNA molecules, a DNA polymerase proof reading or not proof reading (for example and without limitation Phusion DNA polymerase), suitable buffer(s), and suitable dNTPs. In this example all the USER treated modified target polynucleotide, purified or un-purified, is combined with 50 pmoles of a primer complementary to the universal sequence now present on 3' end of target DNA molecules (2-001), 2 units of Phusion DNA polymerase, 10 ul of 5× Phusion DNA polymerase buffer, and 12 nmole of each dNTP (dATP/dTTP/dCTP/dGTP). The mixture is then thermocycled to one-pass extend or linearly amplify the target nucleic acid extension product to generate first complement sequence (CS), in this example 98° C. for 30 seconds, 5 cycles of 98° C. for 5 seconds, 60° C. for 1 minute, and 72° C. for 1 minute, followed by 72° C. for 2 minutes. The linear CS product can then be optionally purified by any suitable method, for example using magnetic beads. As depicted in section (E) of FIG. 14.

Annealing of a Second Adaptor Template Oligo(s) to First Complementary Strand

The first CS products are mixed with a suitable quantity of a second Adaptor Template Oligo(s) (for example and without limitation an oligo which forms a hairpin), in a suitable buffer. In this example first CS products are mixed with 200 pmole of ATO (1-018), in $H_2O$ to a final volume of 15 ul. The mixture is heated at a suitable temperate, in this example 95° C., for a suitable time, in this example 2 minutes, or other temperatures or times which can result in denaturing of double strand nucleic acids to single strands. The nucleic acids and ATO(s) mixture are in this example subsequently cooled to 4° C. for 2 minutes, or other suitable temperatures or times capable of promoting annealing between nucleic acids and ATO(s). As depicted in section (F) of FIG. 14.

First Complementary Strand Extension by its Use as a Primer with the Second Adaptor Template Oligo(s) as a Template to Form Modified First Complementary Strand A suitable quantity of DNA polymerase(s), proof reading or not proof reading, with strand displacement or no strand displacement activity (for example and without limitation Taq DNA polymerase, or Phusion), mixed with suitable buffer(s), and suitable dNTPs, is combined with the DNA-ATO(s) mixture. In this example a total of 2.5 units of Klenow and 2.5 units of TAQ DNA polymerase, 2 ul of 10×TAQ DNA polymerase buffer, and 10 nmole of each dNTP (dATP/dTTP/dCTP/dGTP), is combined with the DNA-ATO mixture to a final volume of 20 ul. To further promote target nucleic acid and ATO(s) annealing in the presence of DNA polymerase(s) and buffer(s) the mixture in this example is incubated below 25° C. for 30 minutes, or other suitable temperatures or times capable of promoting annealing between nucleic acids and ATO(s). To promote extension of the target nucleic acids using the ATO(s) sequence as a template in this example the incubation temperate is increased to 37° C. for 30 minutes, or other suitable temperatures capable of promoting DNA polymerase activity. As depicted in section (G) of FIG. 14.

Degradation of Adaptor Template Oligo(s)

Adaptor template oligo(s) are selectively degraded by the addition of a combination of, for example but not limited to, dU-glycosylase, and an apurinic/apyrimidinic endonuclease, in this example 2 units of USER enzyme, was added to the 20 ul modified target polynucleotide reaction mixture, followed by sequential incubations of, in this example, 37° C. for 30 minutes and then 25° C. for 15 minutes, or other suitable temperatures and times capable of promoting enzyme activity. The degraded ATO(s) can optionally be removed using any suitable purification method. As depicted in section (H) of FIG. 14.

Exponential Amplification of Modified First Complementary Strand Product by PCR

The modified first CS product, purified or un-purified, is combined with two primers, one with sequence similarity with, and designed to bind to, the extension formed with the first ATO(s) and will contain sequences compatible and necessary for sequencing using Next Generation Sequencing technologies (for example and without limitation, P5 or P7 adaptor sequences, patient/sample index sequences, Illumina or custom read 1 or read 2 sequences for compatibility with Illumina Next Generation Sequencers), and a second primer with sequence similarity with, and designed to bind to, the extension formed with the second ATO(s) and also contains sequences compatible and necessary for sequencing using Next Generation Sequencing technologies (for example and without limitation, P5 or P7 adaptor sequences, patient/sample index sequences, Illumina or custom read 1 or read 2 sequences for compatibility with Illumina Next Generation Sequencers), a proof reading polymerase (for example and without limitation Phusion DNA polymerase, Q5), suitable buffer(s), and suitable dNTPs, and other suitable or necessary additives (for example and without limitation, DMSO, betaine, and ammonium sulfate). In this example purified modified first CS products are combined with 50 pmole of each of two primers (2-002, and 2-003), 2 units of Phusion DNA polymerase, 10 ul of 5× Phusion DNA polymerase buffer, 10 nmole of each dNTP (dATP/dTTP/dCTP/dGTP), and 1 umole of ammonium sulfate in a final volume of 50 ul. The mixture is then thermocycled to exponentially amplify the modified first CS product, in this example 98° C. for 30 seconds, 12× cycles of 98° C. for 5 seconds, 60° C. for 1 minute, and 72° C. for 1 minute, followed by 72° C. for 2 minutes. The amplification product can then be purified by any suitable method, for example using magnetic beads. The final amplification product will be compatible with, for example, next generation sequencing on an Illumina platform. As depicted in section (I) of FIG. 14.

Results

Using a bioanalyzer high sensitivity kit from Agilent to assess the final complete sequencing library, we were able to demonstrate that the final product of the library preparation has a size distribution equivalent to that which would be expected given the distribution of input material.

As depicted in section (J) of FIG. 14.

Conclusion

By combining a first ATO reaction using fragmented gDNA, a process of linear amplification to generate multiple first complementary strands, a second ATO reaction using the linear amplification product as a target polynucleotide followed by global amplification we have successfully validate this technological approach for the use in generation of sequencing libraries.

Example 2

Using deoxyribonucleic acid (DNA) as the target polynucleotide for producing a Targeted Amplicon Next Generation Sequencing Library (for example and without limitation, compatible with Illumina Next Generation Sequencers) using for example and without limitation, an adaptor template oligo(s) with a hairpin produced using a chemical spacer (for example and without limitation, a C3 spacer, a C18 spacer).

Materials

Target polynucleotide, human gDNA (BIO-35025)
DNA fragmenting enzyme, KAPA Frag Kit (Roche, 7962517001)
Adaptor template oligos (ATO), 1-006 (Table 1)
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
Phusion® High-Fidelity DNA Polymerase (NEB, M0530S)
Phusion buffer (NEB, M0530S)
USER® Enzyme (NEB, M5505S)
Primers, 2-004, 2-005 (Table 2)
Ammonium sulfate (SIGMA, A4418)
Agencourt AMPure XP (Beckman Coulter, A63881)
Bioanalyzer high sensitivity kit from Agilent (product ID 5067-4626)
SYBR™ Green I nucleic acid gel stain (Invitrogen, S7563)

Method

Annealing of an Adaptor Template Oligo(s) to Deoxyribonucleic Acids

As in example 1, with a total of 25 ng of fragmented target polynucleotide, 100 pmole of ATO 1-006 for a total of 100 pmole of ATO, in $H_2O$ to a final volume of 7.5 ul. As depicted in sections (A) and (B) of FIG. 13.

Target Deoxyribonucleic Acid Extension by its Use as a Primer with the Adaptor Template Oligo(s) as a Template As in example 1, with a total of 1.25 units of Klenow and 1.25 units of TAQ DNA polymerase, 1 ul of 10×TAQ DNA polymerase buffer, and 5 nmole of each dNTP (dATP/dTTP/dCTP/dGTP), combined with the DNA-ATO mixture to a final volume of 10 ul. As depicted in section (C) of FIG. 13.

Degradation of Adaptor Template Oligo(s)

As in example 1. As depicted in section (D) of FIG. 13.

First Exponential Amplification of Modified Target Polynucleotide by PCR

The modified target polynucleotide, purified or un-purified, is combined with a universal primer complementary to the universal sequence originally on the ATO(s) and now present on the 3' end of target polynucleotide, a pool of target specific primers designed to target regions of DNA which contain mutations of interest (for example and without limitation, single nucleotide polymorphism(s), indel(s), DNA fusion(s)), a suitable quantity of DNA polymerase(s), proof reading or not proof reading (for example and without limitation Taq DNA polymerase, or Phusion), suitable buffer (s), suitable dNTPs, and other suitable or necessary additives (for example and without limitation, DMSO, betaine, and ammonium sulfate). In this example 5 ul of the modified target polynucleotide, 50 pmole of 2-004, 100 pmole of a pool of target specific primers, 12 nmole of each dNTP (dATP/dTTP/dCTP/dGTP), 2 units of Phusion DNA Polymerase, 10 ul of 5× Phusion buffer, and 1 umole of ammonium sulfate were combined in a final volume of 50 ul. The mixture is then thermocycled to amplify the chosen regions of the target nucleic acid extension product, in this example 98° C. for 1 min, 15 cycles of 98° C. for 5 seconds, 60° C. for 5 minutes, and 72° C. for 30 seconds, followed by 72° C. for 2 minutes. The amplification product can then be optionally purified by any suitable method, for example using magnetic beads, in this example PCR products were eluted in 30 ul, as depicted in section (E) of FIG. 13.

Optional Second Exponential Amplification of First Exponential Amplification Product by PCR The purified first exponential amplification product, is combined with a second nested universal primer with sequence similarity with, and designed to bind to, the universal sequence introduced by the first universal primer which will contain sequences compatible and necessary for sequencing using Next Generation Sequencing technologies (for example and without limitation, P5 or P7 adaptor sequences, patient/sample index sequences, Illumina or custom read 1 or read 2 sequences for compatibility with Illumina Next Generation Sequencers), a second pool of targeted primers designed to target regions of DNA, including or nested, relative to the first primer pool which also target regions of DNA containing mutations of interest and also contains sequences compatible and necessary for compatibility with next generation sequencing technologies (for example and without limitation, P5 or P7 adaptor sequences, patient/sample index sequences, Illumina or custom read 1 or read 2 sequencing primer sites, for compatibility with Illumina Next Generation Sequencers), a proof reading polymerase (for example and without limitation Phusion DNA polymerase, Q5), suitable buffer(s), suitable dNTPs, and other suitable or necessary additives (for example and without limitation, DMSO, betaine, and ammonium sulfate). In this example 10 ul of the purified first amplification product, 12.5 pmole of 2-005, 50 pmole of a nested pool of target specific primers, 5 nmole of each dNTP (dATP/dTTP/dCTP/dGTP), 1 unit of Phusion DNA Polymerase, 5 ul of 5× Phusion buffer, 1x SYBRgreen, and 0.5 umole of ammonium sulfate were combined in a final volume of 25 ul. The mixture is then thermocycled to amplify the chosen regions of the first exponential amplification product, in this example 98° C. for 1 min, 15 cycles of 98° C. for 5 seconds, 60° C. for 5 minutes, and 72° C. for 30 seconds, followed by 72° C. for 2 minutes, as depicted in section (F) of FIG. 13. The amplification product can then be purified by any suitable method, for example using magnetic beads, and will be suitable for Next Generation Sequencing on a compatible technology. In this example the second exponential amplification product was bead purified before, and size distribution determined, being used to generate 150 bp pair-end reads with a MiSeq, as depicted in section (G) of FIG. 13.

Results

The combination of first and second exponential amplifications were able to successfully amplify target regions of the modified target polynucleotide and produce a targeted amplicon library. The inclusion of SYBRgreen in the second exponential amplification reactions allowed for monitoring of the amplification rate of the final library products, melt curve analysis showed relative to a no template control the whole method was capable of producing substantially more high molecular weight products. Using a bioanalyzer high sensitivity kit from Agilent (product ID 5067-4626) to assess the final complete sequencing library, we were able to demonstrate that the final product of the library preparation has a size distribution equivalent to that which would be expected given the distribution of input material. Using this library for generating sequencing data as part of a pooled run with a MiSeq we produced slightly more than 3.6 million reads. The reads were mapped to a reference sample using bwa resulting in a 98% mapping rate. Examining the insert size for the mapped pared end reads reveals an insert distribution from 26 bp (inserts 25 bp or below were filtered out) up to almost 400 bp. With a peak insert size of approximately 100 bp, as depicted in section (H) of FIG. 13. Examination of the efficiency for each target specific primer was done by counting the numbers of reads in the sequencing results which map to each of the primer sites, as depicted in section (I) of FIG. 13. This revealed an even coverage across the target sites. Due to the incorporation of UID we were able to generate 'barcode families' and count the number of families per target site, as depicted in section (J). This revealed a maximum count just in excess of 1000 barcode families.

Conclusion

By combining a first ATO reaction using fragmented gDNA, a process of two rounds of exponential amplification using a pool of target specific primers and a second nested pool of target specific we successfully validated this technological approach for the use in generation of strand specific targeted amplicon based sequencing libraries. Successful sequencing of the final library product on an Illumina MiSeq sequencer confirmed that the final library product contained the components we had designed into it in the correct order necessary for sequencing. Analysing the data revealed successful multiplexed amplification of more than 200 different target regions with similar levels of enrichment for all primers. Comparing the numbers of barcode families for each of the primer sites reveals very little variation across all sites indicating there is little to no bias based on the target sequences in the ATO reaction.

Example 3

Using deoxyribonucleic acid (DNA) as the target polynucleotide for incorporating a promoter for an RNA polymerase to drive amplification of DNA in to RNA using, for example and without limitation, an adaptor template oligo(s) containing sequence compatible with and capable of working as an RNA polymerase promoter as well as a hairpin produced by a nucleotide sequence.

Materials

Target polynucleotide, human gDNA (BIO-35025)
DNA fragmenting enzyme, KAPA Frag Kit (Roche, 7962517001)
Adaptor template oligos (ATO), 1-012 (Table 1)
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
USER® Enzyme (NEB, M5505S)
T7-Scribe Standard RNA IVT kit (CELLSCRIPT, C-AS3107)

Method

Annealing of an Adaptor Template Oligo(s) to Deoxyribonucleic Acids

As in example 1, except the ATO contains sequence(s) compatible with and capable of acting as an RNA polymerase promoter (for example and without limitation a T7, T3, or SP6 promoter sequence), in this example ATO 1-012 which contains a T7 promoter.

Target Deoxyribonucleic Acid Extension by its Use as a Primer with the Adaptor Template Oligo as a Template As in example 1.

In Vitro Transcription Using an RNA Polymerase

The target deoxyribonucleic acid extension (the modified polynucleotide) product, purified or un-purified, is combined with a suitable buffer, suitable NTPs, other suitable additives (for example and without limitation, DTT), and a suitable RNA polymerase (for example and without limitation, a T7 RNA polymerase if a T7 RNA polymerase promoter has been used), for a suitable time and temperature to promote activity of the RNA polymerase. In this example 5 ul of purified modified target polynucleotide, and a commercial kit was used following the manufactures instruction, CELLSCRIPT™ T7-Scribe™ Standard RNA IVT kit, which was incubated at 37° C. for 18 hours in a final volume of 20 ul. The RNA produced was quantified using a high sensitivity Qubit3 reagent, a total of 107 ng/µl was measured, resulting in a total quantity of 2035 ng of RNA produced from the overnight, 18 hour, incubation. The RNA can then form the input material for any suitable RNA based downstream applications, for example and without limitation, RNA Next Generation Sequencing, cDNA synthesis, in situ hybridisation, qPCR, or any other suitable downstream process.

Results

The ATO containing a sequence designed to function as a promoter for an RNA polymerase when double stranded was used in a first ATO reaction for producing a modified target polynucleotide. This first reaction can be judged to be successful as the product of it was used in an invitro transcription reaction which generated a total of 2 ug of RNA.

Conclusion

A nucleotide sequence designed to function as an RNA polymerase promoter can be successfully incorporated into the design of the ATO. After the first ATO extension a portion of the modified target polynucleotide will be double stranded and contain an RNA polymerase promoter. This double strand RNA polymerase promoter can then be used to amplify the target polynucleotide into RNA, rather than DNA. This has the possibility to quickly and robustly greatly amplify a small quantity of DNA into RNA which can then be used as a template for any of a number of downstream applications including RNA-Seq, and cDNA syntheses.

Example 4

Using deoxyribonucleic acid (DNA) as the target polynucleotide for incorporating a promoter for an RNA polymerase to drive amplification of DNA in to RNA using, for example and without limitation, an adaptor template oligo(s) containing sequence compatible with and capable of working as an RNA polymerase promoter as well as a hairpin produced nucleotide sequence, and a second oligo with complementarity to the ATO.

Materials
  Target polynucleotide, human gDNA (BIO-35025)
  DNA fragmenting enzyme, KAPA Frag Kit (Roche, 7962517001)
  Adaptor template oligos (ATO), 1-019, 1-020 (Table 1)
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  dNTPs (NEB, N0447s)
  USER® Enzyme (NEB, M5505S)
  Agencourt AMPure XP (Beckman Coulter, A63881)
  T7-Scribe Standard RNA IVT kit (CELLSCRIPT, C-AS3107)

Method
Annealing of an Adaptor Template Oligo(s) to Deoxyribonucleic Acids
  As in example 3, except using ATO 1-019.
Target Deoxyribonucleic Acid Extension by its Use as a Primer with the Adaptor Template Oligo(s) as a Template
  As in example 1.
Degradation of Adaptor Template Oligo(s)
  As in example 1.
Producing a Double Stranded RNA Polymerase Promoter The target deoxyribonucleic acid extension product, purified or un-purified, is combined with a sequence complementary to the conserved sequence(s) originally on the ATO(s) and now present on target DNA molecules. In this example 15 ul of purified modified target polynucleotide, 100 pmole of 1-020 in H$_2$O of a final volume of 20 ul. The mixture is heated at a suitable temperate, in this example 95° C., and for a suitable time, necessary to facilitate denaturing of double strand nucleic acids to single strands, in this example 2 minutes. The mixture is then cooled to allow formation of a double stranded complex between the modified target polynucleotide and target deoxyribonucleic extension complementary oligo(s), in this example room temperature (25° C.) for at least 5 minutes.

In Vitro Transcription Using RNA Polymerase
  As in example 3.
Results

The ATO containing a sequence designed to function as a promoter for an RNA polymerase when double stranded was used in a first ATO reaction for producing a modified target polynucleotide. This first reaction can be judged to be successful as the product of it was used in an invitro transcription reaction which generated RNA.

Conclusion

A nucleotide sequence designed to function as an RNA polymerase promoter can be successfully incorporated into the design of the ATO. After the first ATO extension, the ATO is digested and removed and complementary oligo is hybridised to the modified target polynucleotide, a portion of the modified target polynucleotide will be double stranded and contain an RNA polymerase promoter. This double strand RNA polymerase promoter can then be used to amplify the target polynucleotide into RNA, rather than DNA. This has the possibility to quickly and robustly greatly amplify a small quantity of DNA into RNA which can then be used as a template for any of a number of downstream applications including RNA-Seq, and cDNA syntheses.

Example 5

Using deoxyribonucleic acid (DNA) as the target polynucleotide for incorporating a promoter for an RNA polymerase to produce amplification of DNA in to RNA using for example and without limitation, an adaptor template oligo(s) with a hairpin (stem-loop) structure produced with two short stem regions of partial or complete complementarity separated by a random, specifically designed, or specifically chosen sequence.

Materials
  Target polynucleotide, human gDNA (BIO-35025)
  DNA fragmenting enzyme, KAPA Frag Kit (Roche, 7962517001)
  Adaptor template oligos (ATO), 1-021 (Table 1)
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  dNTPs (NEB, N0447s)
  Phusion® High-Fidelity DNA Polymerase (NEB, M0530S)
  Phusion buffer (NEB, M0530S)
  USER® Enzyme (NEB, M5505S)
  S1 Nuclease (ThermoFisher, EN0321)
  Agencourt AMPure XP (Beckman Coulter, A63881)
  T7-Scribe Standard RNA IVT kit (CELLSCRIPT, C-AS3107)

Method
Annealing of an Adaptor Template Oligo(s) to Deoxyribonucleic Acids
  As in example 3, except the ATO has in addition to a sequence designed to function as an RNA polymerase promoter contains a hairpin produced with two short regions of partial or complete complementarity separated by a random, specifically designed, or specifically chosen sequence, 1-021.
Target Deoxyribonucleic Acid Extension by its Use as a Primer with the Adaptor Template Oligo(s) as a Template
  As in example 3.
Generating a Double Strand Target Deoxyribonucleic Acid Extension Product Including a Double Strand RNA Polymerase Promoter The modified target polynucleotide reaction mixture is combined with additional heat stable DNA polymerase(s), proof reading or not proof reading (for example and without limitation Taq DNA polymerase, or Phusion), mixed with suitable buffer(s), and suitable dNTPs. In this example the 20 ul modified target polynucleotide reaction, 2 units of Phusion DNA Polymerase, 6 ul of 5× Phusion buffer, 5 nmole of each dNTP (dATP/dTTP/dCTP/dGTP), in a final volume of 30 ul. The mixture is heated at a suitable temperate, in this example 95° C., for a suitable time, in this example 2 minutes, or other temperatures or times which can result in denaturing of double strand nucleic acids to single strands. The sample is then cooled to allow the regions of complementarity (for example and without limitation a nucleotide sequence which forms a hairpin due to the inclusion two regions of partial or complete complementarity) within the target deoxyribonucleic acid extension product and ATO(s) oligo to self-anneal, in this example room temperature (25° C.) for 5 minutes. The 3' region of the modified target deoxyribonucleic acid extension product will form a small hairpin and self-anneal. The temperature is then raised to a suitable temperature for a suitable time necessary to fully extend the 3' end which will act as a primer to initiate extension and formation of a full or partial double stranded target deoxyribonucleic acid extension product with a hairpin separating the two complementary strands, in this example 72° C. for 10 minutes.

Optional Degradation of Adaptor Template Oligo(s)
As in example 1.

In Vitro Transcription Using RNA Polymerase
As in example 3.

Results

The ATO containing a sequencing designed to function as a promoter for an RNA polymerase when double stranded as well as a sequence which would form an internal hairpin was used in a first ATO reaction for producing a modified target polynucleotide. This first reaction can be judged to be successful as the product of it was used in an invitro transcription reaction which generated RNA.

Conclusion

A nucleotide sequence designed to function as an RNA polymerase promoter can be successfully incorporated into the design of the ATO in combination with the internal hairpin and extension. After the first ATO extension, we showed that after the ATO is digested and removed, the regions of complementarity are able reanneal and extend to produce a double strand modified target polynucleotide with a hairpin. This double strand RNA polymerase promoter can then be used to amplify the target polynucleotide into RNA, rather than DNA. This has the possibility to quickly and robustly greatly amplify a small quantity of DNA into RNA which can then be used as a template for any of a number of downstream applications including RNA-Seq, and cDNA syntheses.

Example 6

Using deoxyribonucleic acid (DNA) as the target polynucleotide for producing a Next Generation Sequencing Library (for example and without limitation, compatible with Illumina Next Generation Sequencers) using for example and without limitation, an adaptor template oligo(s) with a hairpin produced with two short regions of partial or complete complementarity separated by a random, specifically designed, or specifically chosen sequence.

Materials
Target polynucleotide, human gDNA (BIO-35025)
DNA fragmenting enzyme, KAPA Frag Kit (Roche, 7962517001)
Adaptor template oligos (ATO), 1-013, 1-022 (Table 1)
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
Phusion® High-Fidelity DNA Polymerase (NEB, M0530S)
Phusion buffer (NEB, M0530S)
USER® Enzyme (NEB, M5505S)
S1 Nuclease (ThermoFisher, EN0321)
Agencourt AMPure XP (Beckman Coulter, A63881)
Primers 2-002, 2-003 (Table 2)

Method

Annealing of an Adaptor Template Oligo to Deoxyribonucleic Acids

As in example 1, except the ATO has in addition to a sequence designed to function as a hairpin produced with two short regions of partial or complete complementarity separated by a random, specifically designed, or specifically chosen sequence, 1-013.

Target Deoxyribonucleic Acid Extension by its Use as a Primer with the Adaptor Template Oligo(s) as a Template
As in example 1.

Generating a Double Strand Modified Target Polynucleotide
As in example 5.

Degradation of Adaptor Template Oligo and Hairpin Degradation

As in example 5, with the addition of the S1 Nuclease. This may require an extra inactivation step in which S1 is inactivated by the addition of EDTA and incubating at 70° C. for 10 minutes, or similar temperatures and times which result in inactivation of the S1 Nuclease.

One-Pass Extension or Linear Amplification of Double Strand Modified Target Polynucleotide to Generate First CS
As in example 1.

Annealing of a Second Adaptor Template Oligo to the First CS

As in example 1, except the ATO has in addition to a sequence designed to function as a hairpin produced with two short regions of partial or complete complementarity separated by a random, specifically designed, or specifically chosen sequence, 1-022.

First CS Extension by its Use as a Primer with the Second Adaptor Template Oligo as a Template to Form a Modified First CS
As in example 1.

Generating a Double Strand Modified Target Polynucleotide
As in example 5.

Degradation of Adaptor Template Oligo and Hairpin Degradation
As above.

Exponential Amplification of Modified First CS by PCR
As in example 1.

Results

Using this example, we can show that using self-annealing and extension of a modified target polynucleotide and the modified first CS produces a template for the final exponential amplification which results in a complete whole genome next generation sequencing library.

Conclusion

By combining a first ATO reaction using fragmented gDNA, a process of self-annealing and extending to generate double strand DNA, one-pass extension or linear amplification to generate multiple first complementary strands, a second ATO reaction using the linear amplification product as a target polynucleotide, followed by global amplification we have successfully validate this technological approach for the use in generation of sequencing libraries.

Example 7

Using deoxyribonucleic acid (DNA) as the target polynucleotide for producing a Next Generation Sequencing Library (for example and without limitation, compatible with Illumina Next Generation Sequencers) using for example and without limitation, an adaptor template oligo(s) with a hairpin produced with two short regions of partial or complete complementarity separated by a random, specifically designed, or specifically chosen sequence, and a double-stranded or partially double-stranded ordinary adaptor.

Materials

Target polynucleotide, human gDNA (BIO-35025)

DNA fragmenting enzyme, KAPA Frag Kit (Roche, 7962517001)

Adaptor template oligos (ATO), 1-022 (Table 1)

TAQ DNA polymerase (NEB, M0273L)

TAQ DNA polymerase buffer (NEB, M0273L)

DNA Polymerase I, Large (Klenow) Fragment (NEB, M0210L, M0212L)

dNTPs (NEB, N0447s)

Phusion® High-Fidelity DNA Polymerase (NEB, M0530S)

Phusion buffer (NEB, M0530S)

USER® Enzyme (NEB, M5505S)

T4 DNA Ligase (NEB, M0202S)

Method

Annealing of an Adaptor Template Oligo(s) to Deoxyribonucleic Acids

As in example 1, except the ATO has in addition to a sequence designed to function as a hairpin produced with two short regions of partial or complete complementarity separated by a random, specifically designed, or specifically chosen sequence, 1-022.

Target Polynucleotide Extension by its Use as a Primer with the Adaptor Template Oligo as a Template As in example 1.

Generating a Double Strand Modified Target Polynucleotide

As in example 5.

Ligation of a Double Strand Adaptor(s) to the End of the Double Strand Target Deoxyribonucleic Acid Extension Product The double strand modified target polynucleotide, purified or un-purified, is mixed with a suitable quantity of blunt end or 3' T nucleotide over hang end, fully double strand, partially double strand, with or without a hairpin, adaptor, a suitable quantity of ligase(s) (for example and without limitation, T4 DNA ligase), suitable buffer(s), and any other necessary reagent(s). In this example 15 ul of purified double strand modified target polynucleotide, 50 nmole of adaptor, 100 units of T4 DNA ligase, 2 ul of 10× ligase buffer in a final volume of 20 ul. The mixture is incubated at a suitable temperate and suitable time to allow for complete ligation to all double strand target nucleic acid extension product ends, in this example 25° C. for 30 minutes, or other suitable temperatures and times capable of promoting enzyme activity.

Optional Degradation of Adaptor Template Oligo(s) and Hairpin Degradation

As in example 6.

Exponential Amplification of Ligated Extension Product by PCR

As in example 1.

Results

Using this example, we can show that using self-annealing and extension of a modified target polynucleotide to generate a double strand first CS and ligating an adaptor to the available end successfully produces a template for the final exponential amplification which results in a complete whole genome next generation sequencing library.

Conclusion

By combining a first ATO reaction using fragmented gDNA, a process of self-annealing and extending to generate double strand DNA, ligation of a double strand adaptor to the exposed end, to generate second double stranded DNA product, followed by global amplification we have successfully validate this technological approach for the use in generation of sequencing libraries.

Example 8

Using deoxyribonucleic acid (DNA) as the target polynucleotide to produce a 'PCR' free Next Generation Sequencing Library (for example and without limitation, compatible with Illumina Next Generation Sequencers) using for example and without limitation, an adaptor template oligo(s) with a hairpin produced with two short regions of partial or complete complementarity separated by a random, specifically designed, or specifically chosen sequence, and a double-stranded or partially double-stranded ordinary adaptor.

Materials

Target polynucleotide, human gDNA (BIO-35025)

DNA fragmenting enzyme, KAPA Frag Kit (Roche, 7962517001)

Adaptor template oligos (ATO), 1-023 (Table 1)

TAQ DNA polymerase (NEB, M0273L)

TAQ DNA polymerase buffer (NEB, M0273L)

DNA Polymerase I, Large (Klenow) Fragment (NEB, M0210L, M0212L)

dNTPs (NEB, N0447s)

Phusion® High-Fidelity DNA Polymerase (NEB, M0530S)

Phusion buffer (NEB, M0530S)

USER® Enzyme (NEB, M5505S)

Agencourt AMPure XP (Beckman Coulter, A63881)

T4 DNA Ligase (NEB, M0202S)

Method

Annealing of an Adaptor Template Oligo(s) to Deoxyribonucleic Acids

As in example 1, except the ATO has sequences which form a hairpin due to the inclusion two regions of partial or complete complementarity which comprises P5 or P7 adaptor sequences, patient/sample index sequences, Illumina or custom read 1 or read 2 sequences for compatibility with Illumina Next Generation Sequencers, 1-023.

Target Polynucleotide Extension by its Use as a Primer with the Adaptor Template Oligo(s) as a Template
    As in example 1.
Generating a Double Strand Target Deoxyribonucleic Acid Extension Product
    As in example 5.
Annealing and Ligation of an Adaptor(s) to the End of the Double Strand Target Deoxyribonucleic Acid Extension Product
    As in example 7.
Optional Degradation of Adaptor Template Oligo(s) and Hairpin Degradation
    As in example 6.
Results
    Using this example, we can show that using self-annealing and extension of a modified target polynucleotide to generate a double strand first CS and ligating an adaptor to the available end successfully produces a template for 'exponential PCR' free next generation sequencing.
Conclusion
    By combining a first ATO reaction using fragmented gDNA, a process of self-annealing and extending to generate double strand DNA, ligation of a double strand adaptor to the exposed end, to generate second double stranded DNA product, we have successfully validated this technological approach for an 'exponential PCR' free next generation sequencing.

Example 9

Using deoxyribonucleic acid (DNA) as the target polynucleotide for producing a PCR free Next Generation Sequencing Library (for example and without limitation, compatible with Illumina Next Generation Sequencers) using for example and without limitation, an adaptor template oligo(s) with a hairpin (stem-loop structure0 wherein the loop comprises a chemical spacer (for example and without limitation, a C3 spacer, a C18 spacer), and a double-stranded or partially double-stranded ordinary adaptor.
Materials
    Target polynucleotide, human gDNA (BIO-35025)
    DNA fragmenting enzyme, KAPA Frag Kit (Roche, 7962517001)
    Adaptor template oligos (ATO), 1-023 (Table 1)
    TAQ DNA polymerase (NEB, M0273L)
    TAQ DNA polymerase buffer (NEB, M0273L)
    DNA Polymerase I, Large (Klenow) Fragment (NEB, M0210L, M0212L)
    dNTPs (NEB, N0447s)
    Phusion® High-Fidelity DNA Polymerase (NEB, M0530S)
    Phusion buffer (NEB, M0530S)
    USER® Enzyme (NEB, M5505S)
    T4 DNA Ligase (NEB, M0202S)
    Agencourt AMPure XP (Beckman Coulter, A63881)
    Primer 2-006 (Table 2)
Method
Annealing of an Adaptor Template Oligo to Deoxyribonucleic Acids
    As in example 8 except the hairpin in the ATO is generated by a chemical spacer, 1-024.

Target Polynucleotide Extension by its Use as a Primer with the Adaptor Template Oligo as a Template
    As in example 1.
Degradation of Adaptor Template Oligo
    As in example 1.
Linear Extension to Generate a Double Strand Modified Target Polynucleotide.
    The purified target nucleic acid extension product is combined with an oligonucleotide primer complementary to the conserved sequence now present on the 3' end of the modified target DNA molecules, a polymerase (for example and without limitation Phusion DNA polymerase), suitable buffer(s), and suitable dNTPs. In this example 50 pmoles of a primer complementary to the conserved sequence now present on target DNA molecules (2-006), 2 units of Phusion DNA polymerase, 6 ul of 5× Phusion DNA polymerase buffer, 12 nmole of each dNTP (dATP/dTTP/dCTP/dGTP), and 15 µl of purified modified target polynucleotide, in a final volume of 30 ul. The mixture is incubated at, in this example 60-72° C. for 30 minutes, or other suitable temperatures and times capable of promoting enzyme activity to extend the oligonucleotide(s) to create a blunt end or A-Tailed double strand DNA product. The products can then be purified using any suitable purification method.
Ligation of an Ordinary Adaptor(s) to the End of the Double Stranded Target Deoxyribonucleic Acid Extension Product
    As in example 8.
Results
    Using this example, we can show that using a combination of a first ATO reaction, one round of extension and ligation of a ordinary adaptor can successfully produce a template for PCR free next generation sequencing.
Conclusion
    By combining a first ATO reaction using fragmented genomic DNA, a first ATO reaction, removal of the ATO and annealing an oligo complementary to the universal sequence, one pass linear extension, followed by ligating a double strand adaptor to the 5' end of the modified target polynucleotide, we have successfully validated this technological approach for an 'PCR' free next generation sequencing.

Example 10

Using deoxyribonucleic acid (DNA) as the target polynucleotide for producing a Next Generation Sequencing Library (for example and without limitation, compatible with Illumina Next Generation Sequencers) using for example and without limitation, a single stranded adaptor template oligo(s).
Materials
    Target polynucleotide, human gDNA (BIO-35025)
    DNA fragmenting enzyme, KAPA Frag Kit (Roche, 7962517001)
    Adaptor template oligos (ATO), 1-025, 1-026 (Table 1)
    TAQ DNA polymerase (NEB, M0273L)
    TAQ DNA polymerase buffer (NEB, M0273L)
    DNA Polymerase I, Large (Klenow) Fragment (NEB, M0210L, M0212L)
    dNTPs (NEB, N0447s)
    Phusion® High-Fidelity DNA Polymerase (NEB, M0530S)
    Phusion buffer (NEB, M0530S)
    USER® Enzyme (NEB, M5505S)
    Agencourt AMPure XP (Beckman Coulter, A63881)
    Primer 2-002, 2-003 (Table 2)

Method
Annealing of an Adaptor Template Oligo to Deoxyribonucleic Acids
As in example 1, except the ATO is single stranded, 1-025.
Target Polynucleotide Extension by its Use as a Primer with the Adaptor Template Oligo(s) as a Template
As in example 1
Degradation of Adaptor Template Oligo(s)
As in example 1
Linear Amplification of Modified Target Polynucleotide
As in example 1
Annealing of a Second Adaptor Template Oligo to First Complementary Strand
As in example 1, except the ATO is single stranded, 1-026.
First Complementary Strand Extension by its Use as a Primer with the Second Adaptor Template Oligo as a Template to Form Modified First Complementary Strand
As in example 1
Degradation of Second Adaptor Template Oligo(s)
As in example 1
Exponential Amplification of Second Adaptor Template Extension Product by PCR
As in example 1
Results
Using single strand ATO we can show successful completion of a genomic next generation sequencing library, similar to that detailed in example 1.
Conclusion
By combining a first ATO reaction using fragmented gDNA, a process of linear amplification to generate multiple first complementary strands, a second ATO reaction using the linear amplification product as a target polynucleotide followed by global amplification we have successfully validate this technological approach for the use in generation of sequencing libraries.

Example 11

Using deoxyribonucleic acid (DNA) as the target polynucleotide for producing a Next Generation Sequencing Library (for example and without limitation, compatible with Illumina Next Generation Sequencers) using for example and without limitation, an adaptor template oligo(s) separated into two complementary strands.
Materials
  Target polynucleotide, human gDNA (BIO-35025)
  DNA fragmenting enzyme, KAPA Frag Kit (Roche, 7962517001)
  Adaptor template oligos (ATO), 1-027, 1-028, 1-029, 1-030 (Table 1)
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  dNTPs (NEB, N0447s)
  Phusion® High-Fidelity DNA Polymerase (NEB, M0530S)
  Phusion buffer (NEB, M0530S)
  USER® Enzyme (NEB, M5505S)
  Agencourt AMPure XP (Beckman Coulter, A63881)
  T4 DNA Ligase (NEB, M0202S)
  Primer 2-002, 2-003 (Table 2)
Method
Annealing of an Adaptor Template Oligo to Deoxyribonucleic Acids
As in example 1, except the ATO is an equal molar mixture of two single strand oligos, 1-027, 1-028.
Target Deoxyribonucleic Acid Extension by its Use as a Primer with the Adaptor Template Oligo(s) as a Template and Ligation
As in example 1, in addition the reaction contains DNA ligase. If the 3' end of the target polynucleotide hybridise to the ATO and is located directly abutting the phosphorylated 5' end of upper strand of the ATO, the 3'end of the target polynucleotide is ligated to the 5' end upper strand of ATO without needing extension. If the 3' end of the target polynucleotide hybridise to the ATO and is located at some distance to the phosphorylated 5' end of upper strand of the ATO, the 3'end of the target polynucleotide is extended by DNA polymerase and is ligated to the 5' end upper strand of ATO, In this example the reaction contains extension components as example 1 and in addition with 100 units of T4 DNA ligase, 2.5 ul of 10×DNA ligase buffer, in a final volume of 25 ul. The mixture is incubated at a suitable temperate and suitable time to allow for ligation or extension-ligation between 3' end of target polynucleotide or its extension product and Adaptor Template Complement Oligo(s) which is upper separate strand or 5' end of stem portion of stem structure of the ATO, in this example 25° C. for 30 minutes, or other suitable temperatures and times capable of promoting enzyme activity.
Degradation of Adaptor Template Oligo(s)
As in example 1.
Optional Linear Amplification of Modified Target Polynucleotide
As in example 1.
Optional Annealing of a Second Adaptor Template Oligo to First Complementary Strand
As in example 1, except the ATO is an equal molar mixture of two single strand oligos, 1-029, 1-030.
Optional First Complementary Strand Extension by its Use as a Primer with the Second Adaptor Template Oligo as a Template to Form Modified First Complementary Strand and Ligation as in the Earlier Step in this Example
As in example 1, and above.
Degradation of Second Adaptor Template Oligo(s)
As in example 1.
Exponential Amplification of Second Adaptor Template Extension Product by PCR
As in example 1.
Results
Using an ATO divided into two complementary strands we can show successful completion of a genomic next generation sequencing library, similar to that detailed in example 1.
Conclusion
By combining a first ATO reaction using fragmented gDNA, a process of linear amplification to generate multiple first complementary strands, a second ATO reaction using the linear amplification product as a target polynucleotide followed by global amplification we have successfully validate this technological approach for the use in generation of sequencing libraries.

Example 12

Using deoxyribonucleic acid (DNA) as the target polynucleotide for producing a Targeted Amplicon Next Generation Sequencing Library (for example and without limitation, compatible with Illumina Next Generation Sequencers) using for example and without limitation, target specific adaptor template oligo(s) (ATO) with a hairpin (stem-loop) wherein the loop comprises a chemical spacer (for example and without limitation, a C3 spacer, a C18 spacer), wherein the 3' end of ATO comprises target specific sequence. The 3' target specific sequence is used to guide the hybridisation between target polynucleotide and ATO. The ATO may comprise usual 3' random sequence between the 3' target specific sequence and the 5' universal sequence as described in other examples, or may comprise short 3' random sequence because this 3' random sequence may purely function as UID not as template for annealing, or may not comprise any 3' random sequence. The 5' universal sequence may comprise RNA polymerase promoter sequence.

Materials
  Target polynucleotide, human gDNA (BIO-35025)
  DNA fragmenting enzyme, KAPA Frag Kit (Roche, 7962517001)
  Adaptor template oligos (ATO), various.
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  dNTPs (NEB, N0447s)
  Phusion® High-Fidelity DNA Polymerase (NEB, M0530S)
  Phusion buffer (NEB, M0530S)
  USER® Enzyme (NEB, M5505S)
  Ammonium sulfate (SIGMA, A4418)
  Agencourt AMPure XP (Beckman Coulter, A63881)
  Primer 2-002, 2-003 (Table 2)

Method

Annealing of an Adaptor Template Oligo Pool to Deoxyribonucleic Acids
  As in example 1, except the ATOs are a pool of 200 different ATOs whose 3' ends have target specific sequences.

Target Deoxyribonucleic Acid Extension by its Use as a Primer with the Adaptor Template Oligo(s) as a Template
  As in example 1. Since the 3' end of the target polynucleotide may be an overhang when hybridising to its ATO, the 3' exonuclease of the DNA polymerase trim the overhang before extension takes place.

Degradation of Adaptor Template Oligo(s)
  As in example 1.

First Exponential Amplification of Adaptor Template Extension Product by PCR
  As in example 1.

Second Exponential Amplification of First Exponential Amplification Product by PCR for Generating a Final Sequencing Library
  As in example 1.

Results
  By using a pool of ATO with 3' target specific sequences we can show successful completion of a targeted amplicon next generation sequencing library, similar to that detailed in example 2.

Conclusion
  By combining a first ATO reaction using fragmented gDNA and a pool of ATOs, a process of two rounds of target specific amplification, we have successfully validate this technological approach for the use in generation of target next generation sequencing libraries.

Example 13

Using deoxyribonucleic acid (DNA) as the target polynucleotide for producing a Targeted Amplicon Next Generation Sequencing Library (for example and without limitation, compatible with Illumina Next Generation Sequencers) using for example and without limitation, target specific Adaptor Template Oligo(s) with a hairpin (a stem-loop) wherein the loop comprises a chemical spacer (for example and without limitation, a C3 spacer, a C18 spacer), in a single round of PCR.

Materials
  Target polynucleotide, human gDNA (BIO-35025)
  DNA fragmenting enzyme, KAPA Frag Kit (Roche, 7962517001)
  Adaptor template oligos (ATO), 1-014, 1-015, 1-016, 1-017.
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  dNTPs (NEB, N0447s)
  Phusion® High-Fidelity DNA Polymerase (NEB, M0530S)
  Phusion buffer (NEB, M0530S)
  USER® Enzyme (NEB, M5505S)
  Primer 2-003 (Table 2)
  Agencourt AMPure XP (Beckman Coulter, A63881)
  Ammonium sulfate (SIGMA, A4418)
  SYBR™ Green I nucleic acid gel stain (Invitrogen, S7563)
  Pool of target specific primers with the following 5' tail
    AAT GAT ACG GCG ACC ACC GAG
    ATC TAC ACT CTT TCC CTA CAC GAC GCT CTT CCG ATC T Method Annealing of an Adaptor Template Oligo Pool(s) to Deoxyribonucleic Acids
  As in example 2, except a pool of 50 nmole of each ATO of 1-014, 1-015, 1-016, and 1-017 were used.

Target Polynucleotide Extension by its Use as a Primer with the Adaptor Template Oligo(s) as a Template
  As in example 2.

Degradation of Adaptor Template Oligo(s)
  As in example 2.

Exponential Amplification of Linear Extension Product by PCR for Generating a Final Sequencing Library
  The purified modified target polynucleotide, is combined with a universal primer with sequence similarity with, and designed to bind to, the conserved sequence(s) introduced by the ATO(s), which contain sequences compatible and necessary with next generation sequencing technologies (for example and without limitation, P5 or P7 adaptor sequences, patient/sample index sequences, Illumina or custom read 1 or read 2 sequences for compatibility with Illumina Next Generation Sequencers), a pool of primers designed to target regions of DNA in proximity to the pool of ATO oligos which also target regions of DNA containing mutations of interest and also contains sequences compatible and necessary for compatibility with next generation sequencing technologies (for example and without limitation, P5 or P7 adaptor sequences, patient/sample index sequences, Illumina or custom read 1 or read 2 sequencing primer sites, for compatibility with Illumina Next Generation Sequencers), a proof reading polymerase (for example and without limitation Phusion DNA polymerase, Q5), suitable buffer(s), suitable dNTPs, and other suitable or necessary additives (for example and without limitation, DMSO, betaine, and ammonium sulfate). In this example 20 ul of the purified modified target polynucleotide, 25 pmole of 2-003, a total of 100 pmole of a pool of target specific primers, 10 nmole of each dNTP (dATP/dTTP/dCTP/dGTP), 1 unit of Phusion DNA Polymerase, 10 ul of 5× Phusion buffer, 1x SYBRgreen, and 1 umole of ammonium sulfate were combined in a final volume of 50 ul. The mixture is then thermocycled to amplify the chosen regions, in this example 98° C. for 1 min, 15 cycles of 98° C. for 5 seconds, 60° C. for 5 minutes, and 72° C. for 30 seconds, followed by 72° C. for 2 minutes. The amplification product can then be purified by any suitable method, for example using magnetic beads, and will be suitable for Next Generation Sequencing on a compatible technology.

Results

Using a single round of exponential amplification as opposed to two rounds as shown in example 2, we were able to generate a target amplicon next generation sequencing library.

Conclusion

By combining a first ATO reaction using fragmented gDNA, a process of a single round of exponential amplification using a pool of target specific primers and a universal primer we successfully validated this technological approach for the use in generation of strand specific targeted amplicon based sequencing libraries.

Example 14

Using ribonucleic acid (RNA) as the target polynucleotide for producing a Next Generation Sequencing Library (for example and without limitation, compatible with Illumina Next Generation Sequencers) using for example and without limitation, an adaptor template oligo(s) with a hairpin).

Materials
- Adaptor template oligos (ATO), 1-014, 1-015, 1-016, 1-017, 1-018.
- TAQ DNA polymerase (NEB, M0273L)
- TAQ DNA polymerase buffer (NEB, M0273L)
- DNA Polymerase I, Large (Klenow) Fragment (NEB, M0210L, M0212L)
- dNTPs (NEB, N0447s)
- Phusion® High-Fidelity DNA Polymerase (NEB, M0530S)
- Phusion buffer (NEB, M0530S)
- USER® Enzyme (NEB, M5505S)
- AMV Reverse Transcriptase (NEB, M0277S)
- Antarctic Phosphatase (NEB, M0289S)
- Agencourt AMPure XP (Beckman Coulter, A63881)
- Primer 2-001, 2-002, 2-003 (Table 2)

Method

Annealing of an Adaptor Template Oligo(s) to Ribonucleic Acids

As in example 1, except 25 ng of fragmented messenger RNA was used as the target polynucleotide.

Target Ribonucleic Acid Extension by its Use as a Primer with the Adaptor Template Oligo(s) as a Template As in example 1, with the addition of making sure the chosen DNA polymerases are capable of using an RNA primer and an optional additional of 5 units of Antarctic Phosphatase.

Degradation of Adaptor Template Oligo(s)

As in example 1, with the addition of making sure any digestion/removal steps do not non-specifically degrade RNA.

One-Pass Extension or Linear Amplification of Modified Target Polynucleotide by Reverse Transcriptase The modified target polynucleotide, purified or un-purified, is combined with a primer complementary to the conserved (universal) sequence now present on the 3' end of the target RNA molecules, a reverse transcriptase (for example and without limitation, M-MuLV, or AMV Reverse Transcriptase), suitable buffer(s), and suitable dNTPs. In this example the purified modified target polynucleotide is mixed with 50 nmole of 2-001, 10 units of AMV Reverse Transcriptase, 2 ul of 10×AMV buffer, 10 nmole of each dNTP (dATP/dTTP/dCTP/dGTP). The mixture is then incubated to produce cDNA (first CS), in this example 42° C. for 30 minutes. The reverse transcription product or linear amplification product can then be purified by any suitable method, for example using magnetic beads.

Annealing of a Second Adaptor Template Oligo(s) to First Complementary Strand

As in example 1.

First Complementary Strand Extension by its Use as a Primer with the Second Adaptor Template Oligo as a Template to Form Modified First Complementary Strand As in example 1.

Degradation of Second Adaptor Template Oligo(s)

As in example 1.

Exponential Amplification of Second Adaptor Template Extension Product by PCR

As in example 1.

Results

Using RNA as the target polynucleotide, and a method similar to that in example 1, we have been able to generate a RNA sequencing library, which contains UIDs for assessing read duplication, low frequency mutation detection, and to improve molecule counting for more accurate quantitation.

Conclusion

By combining a first ATO reaction using fragmented messenger RNA, a process of linear amplification using a reverse transcriptase to generate multiple first complementary strands, a second ATO reaction using the first complementary strands as a target polynucleotide followed by global amplification we have successfully validate this technological approach for the use in generation of RNA sequencing libraries.

Example 15

Using deoxyribonucleic acid (DNA) as the target polynucleotide for producing a Next Generation Sequencing Library (for example and without limitation, compatible with Illumina Next Generation Sequencers) using for example and without limitation, an RNA adaptor template oligo(s) with a hairpin produced using a chemical spacer (for example and without limitation, a C3 spacer, a C18 spacer).

Materials
- Target polynucleotide, human gDNA (BIO-35025)
- DNA fragmenting enzyme, KAPA Frag Kit (Roche, 7962517001)
- Adaptor template oligos (ATO), 1-031, 1-032.
- dNTPs (NEB, N0447s)
- Phusion® High-Fidelity DNA Polymerase (NEB, M0530S)
- Phusion buffer (NEB, M0530S)
- USER® Enzyme (NEB, M5505S)
- Primers, 2-001, 2-002, 2-003 (Table 2)
- AMV Reverse Transcriptase (NEB, M0277S)
- RNase H (NEB, M0297S)
- Agencourt AMPure XP (Beckman Coulter, A63881)

Method

Annealing of an Adaptor Template Oligo to Deoxyribonucleic Acids

As in example 1, except 200 pmole of an RNA ATO is used, 1-031.

Target Deoxyribonucleic Acid Extension by its Use as a Primer with the RNA Adaptor Template Oligo(s) as a Template As in example 1, except 10 unites of AMV Reverse Transcriptase, and 2 ul of 10×AMV buffer were used, with an extension temperature of 42° C. for 30 minutes.

Degradation of Adaptor Template Oligo

Adaptor template oligos are selectively degraded by the addition of an RNAse (for example and without limitation, RNase H, RNase HII, RNase A, RNase T1), followed by incubation at 37° C. for 30 minutes, or other suitable temperatures or times which result in degradation of the RNA-ATO(s), in this example 10 units of RNase H were mixed with the 20 modified target polynucleotide and incubated at 37° C. for 30 minutes and inactivated by incubation at 65° C. for 20 minutes. The degraded ATO(s) can optionally be removed using any suitable purification method.

Linear Amplification of Modified Target Polynucleotide

As in example 1.

Annealing of a Second Adaptor Template Oligo to First Complementary Strand

As in example 1, except 200 pmole of an RNA ATO is used, 1-032.

First Complementary Strand Extension by its Use as a Primer with the Second Adaptor Template Oligo as a Template to Form Modified First Complementary Strand As in example 1, except 10 units of AMV Reverse Transcriptase, and 2 ul of 10×AMV buffer were used, with an extension temperature of 42° C. for 30 minutes.

Degradation of Second Adaptor Template Oligo(s)

As in previous earlier 'Degradation of Adaptor Template Oligo' step.

Exponential Amplification of Second Adaptor Template Extension Product by PCR

As in example 1.

Results

Using an RNA ATO, and a method similar to that in example 1, we have been able to generate a sequencing library, which contains UIDs for assessing read duplication and low frequency mutation detection.

Conclusion

By combining a first ATO reaction using an RNA ATO and fragmented gDNA, a process of linear amplification to generate multiple first complementary strands, a second ATO reaction using a second RNA ATO the linear amplification product as a target polynucleotide followed by global amplification we have successfully validate this technological approach for the use in generation of sequencing libraries.

Example 16

Using ribonucleic acid (RNA) as the target polynucleotide for determination of a transcription start site using for example, and without limitation, an adaptor template oligo(s) with a hairpin produced using a chemical spacer (for example and without limitation, a C3 spacer, a C18 spacer).

Materials

Adaptor template oligos (ATO), 1-014.
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
Phusion® High-Fidelity DNA Polymerase (NEB, M0530S)
Phusion buffer (NEB, M0530S)
USER® Enzyme (NEB, M5505S)
Agencourt AMPure XP (Beckman Coulter, A63881)
Primers, 2-003 (Table 2)
AMV Reverse Transcriptase (NEB, M0277S)

Method

Target Specific Reverse Transcription to Produce cDNA

A suitable quantity of ribonucleic acid (RNA), either fragmented or unfragmented of any length, are mixed with a suitable quantity of gene specific primer(s) targeting a region of RNA (for example and without limitation messenger RNA, micro RNA, ribosomal RNA, or non-coding RNA) for which the transcription start site is undetermined, in a suitable buffer. In this example 100 ng of mRNA was combined with 10 pmole of target specific primer, 10 units of AMV Reverse Transcriptase, 2 ul of 10×AMV buffer, and 10 nmole of each dNTP (dATP/dTTP/dCTP/dGTP), in a final volume of 20 ul. The mixture is heated at a suitable temperate, in this example 65° C., for a suitable time, in this example 2 minutes, or other temperatures or times which can result in denaturing of double strand nucleic acids to single strands. The nucleic acids and target specific primer are subsequently cooled to, in this example 25° C. for 5 minutes, or other suitable temperatures or times capable of promoting annealing and reverse transcription between nucleic acids and gene specific primer(s). The mixture is then incubated to produce cDNA, in this example 42° C. for 30 minutes. The cDNA can then be purified by any suitable method, for example using magnetic beads.

Annealing of an Adaptor Template Oligo to cDNA

As in example 1.

cDNA Extension by its Use as a Primer with the Adaptor Template Oligo(s) as a Template As in example 1.

Degradation of Adaptor Template Oligo(s)

As in example 1.

Exponential Amplification of Target Complementary Deoxyribonucleic Acid Extension Product by PCR for Generating a Final Sequencing Library The modified cDNA, is combined with a universal primer complementary to the conserved sequence introduced by the ATO(s), a second primer designed to target a region of mRNA in proximity to the initial gene specific primer, a DNA polymerase (for example and without limitation Taq DNA polymerase, or Phusion), suitable buffer(s), suitable dNTPs, and other suitable or necessary additives (for example and without limitation, DMSO, betaine, and ammonium sulfate). In this example 5 ul of cDNA, 10 pmole of 2-003, 10 pmole of a target specific primer, 2 units of Phusion DNA polymerase, 10 ul of 5× Phusion DNA polymerase buffer, and 10 nmole of each dNTP (dATP/dTTP/dCTP/dGTP) in a final volume of 50 ul. The mixture is then thermocycled to exponentially amplify the target nucleic acid extension product, in this example 98° C. for 30 seconds, 25× cycles of 98° C. for 5 seconds, 60° C. for 1 minute, and 72° C. for 1 minute, followed by 72° C. for 2 minutes. The amplification product can then be purified by any suitable method, for example using magnetic beads. The purified product can then be used in down steam processes, such as gel electrophoresis to identify major products, cloning and sequencing, or directly to compatible cloning systems and sequencing after transformations and colony selection.

Exponential Amplification of Target Complementary Deoxyribonucleic Acid Extension Product by PCR for Generating a Final Sequencing Library This can be done along with, or instead of the previous step. The method is as in the previous step, except the target specific primer requires a 5' tail containing sequences compatible and necessary with next generation sequencing technologies (for example and without limitation, P5 or P7 adaptor sequences, patient/sample index sequences, Illumina or custom read 1 or read 2 sequences for compatibility with Illumina Next Generation Sequencers). The amplification product can be purified by any suitable method, for example using magnetic beads, and will be suitable for Next Generation Sequencing on a compatible technology.

Results

Using a gene specific primer, we successfully produced cDNA which was used as a template for an ATO reaction, the product of which, when used with two additional primers generated a library capable of being sequenced on an Illumina machine, the results of which revealed the transcription start site of the chosen transcript.

Conclusion

We were successfully able to adapt this technology towards identifying the transcription start site of a chosen gene by combining gene specific cDNA production using a primer near the 5' of the mRNA. Given the fact that only a small number of reads are necessary to identify all possible transcription start sites a whole sequencing run, even on the small output machines, is unnecessary. The approach to generate a product compatible with next generation sequencing is best used as a small spike in to another library where a great depth is needed, or, a multiplex a very large number of gene specific primers to identify a host of transcription start sites.

Example 17

Using a mixture of deoxyribonucleic acid (DNA) and ribonucleic acid (RNA) as the target polynucleotides for producing a combined DNA and RNA Next Generation Sequencing Library (for example and without limitation, compatible with Illumina Next Generation Sequencers) using for example and without limitation, an adaptor template oligo(s) with a hairpin produced using a chemical spacer (for example and without limitation, a C3 spacer, a C18 spacer).

Materials

Target polynucleotide, human gDNA (BIO-35025)

DNA fragmenting enzyme, KAPA Frag Kit (Roche, 7962517001)

Adaptor template oligos (ATO), 1-014, 1-015, 1-016, 1-017, 1-018 (Table 1)

TAQ DNA polymerase (NEB, M0273L)

TAQ DNA polymerase buffer (NEB, M0273L)

DNA Polymerase I, Large (Klenow) Fragment (NEB, M0210L, M0212L)

dNTPs (NEB, N0447s)

Phusion® High-Fidelity DNA Polymerase (NEB, M0530S)

Phusion buffer (NEB, M0530S)

USER® Enzyme (NEB, M5505S)

Primers, 2-001, 2-002, 2-003 (Table 2)

Agencourt AMPure XP (Beckman Coulter, A63881)

Ammonium sulphate (SIGMA, A4418)

AMV Reverse Transcriptase (NEB, M0277S)

Method

Annealing of an Adaptor Template Oligo(s) to Nucleic Acids

As in example 1, except the target polynucleotide is a mixture of RNA and DNA.

Target Nucleic Acid Extension by its Use as a Primer with the Adaptor Template Oligo(s) as a Template As in example 1, with the addition of making sure that the polymerases can use an RNA primer.

Degradation of Adaptor Template Oligo(s)

As in example 1.

One-Pass Extension or Linear Amplification of Adaptor Template Extension Product As in example 1, with the addition of 10 units of AMV Reverse Transcriptase.

Annealing of a Second Adaptor Template Oligo(s) to Form First Complementary Strand As in example 1.

First Complementary Strand Extension by its Use as a Primer with the Second Adaptor Template Oligo as a Template to Form Modified First Complementary Strand As in example 1.

Degradation of Second Adaptor Template Oligo(s)

As in example 1.

Exponential Amplification of Second Adaptor Template Extension Product by PCR

As in example 1.

Results

Using a method similar to that in example 1 we were able to combine both RNA and DNA to produce a next generation sequencing library which include UID suitable for removing PCR duplicates and for correcting errors for identifying low frequency mutations.

Conclusion

Being able to combine DNA and RNA to generate a mixed sequencing library allows for a host of potential applications, especially given the inherent nature of the technology to include UIDs for all target polynucleotides. For example, sequencing both RNA and DNA could allow for comparative mutation analysis.

Example 18

Using a mixture of deoxyribonucleic acid (DNA) and ribonucleic acid (RNA) as the target polynucleotides for producing a combined DNA and RNA Next Generation Sequencing Library (for example and without limitation, compatible with Illumina Next Generation Sequencers) using for example and without limitation, multiple adaptor template oligo(s) with a hairpin produced with two short regions of partial or complete complementarity separated by a random, specifically designed, or specifically chosen sequence, which assign different unique identifies to RNA and DNA molecules for separation of molecules after sequencing.

Materials

Target polynucleotide, human gDNA (BIO-35025)

DNA fragmenting enzyme, KAPA Frag Kit (Roche, 7962517001)

DNA Polymerase I, Large (Klenow) Fragment (NEB, M0210L, M0212L)

Adaptor template oligos (ATO), 1-013, 1-033, 1-036 (Table 1)

dNTPs (NEB, N0447s)

Phusion® High-Fidelity DNA Polymerase (NEB, M0530S)

Phusion buffer (NEB, M0530S)

Deep VentR™ DNA Polymerase (NEB, M0258S)

Tth DNA Polymerase (SIGMA, 000000011480022001)
USER® Enzyme (NEB, M5505S)
Agencourt AMPure XP (Beckman Coulter, A63881)
Primers 2-002,2-003 (Table 2)
Ammonium sulphate (SIGMA, A4418)
AMV Reverse Transcriptase (NEB, M0277S)

Method

Annealing of an Adaptor Template Oligo to Nucleic Acids
  As in example 1, except ATO 1-033 is used.

Specific Extension of Target Deoxyribonucleic Acid Extension, but not Ribonucleic Acid, by its Use as a Primer with the Adaptor Template Oligo as a Template
  A suitable quantity of DNA polymerase(s), capable of using a DNA primer but not a RNA primer, proof reading or not proof reading (for example and without limitation Deep VentR™ DNA Polymerase, LongAmp® Hot Start TaqDNA Polymerase, or OneTaq® Hot StartDNA Polymerase), mixed with suitable buffer(s), and suitable dNTPs, is combined with the DNA/RNA ATO mixture. In this example a total of 2 units of Deep VentR DNA Polymerase, 2 ul of 10× Deep VentR DNA Polymerase buffer, and 10 nmole of each dNTP (dATP/dTTP/dCTP/dGTP), is combined with the DNA-ATO mixture to a final volume of 20 ul. To further promote target nucleic acid and ATO(s) annealing in the presence of DNA polymerase(s) and buffer(s) in this example the mixture is incubated below 25° C. for 30 minutes, or other suitable temperatures or times capable of promoting annealing between nucleic acids and ATO(s). To initiate extension of the target polynucleotides using the ATO sequence as a template in this example the incubation temperate is increased to 37° C. for 30 minutes, or other suitable temperatures capable of promoting DNA polymerase activity. The product is a modified target polynucleotide.

Generating a Double Strand Modified Target Polynucleotide
  As in example 5.

Degradation of Adaptor Template Oligo(s)
  As in example 1.

Annealing of a Second Adaptor Template Oligo(s) to Nucleic Acids
  As in example 1, except ATO 1-036 is used.

Extension of Target Ribonucleic Acid Extension, by its Use as a Primer with the Adaptor Template Oligo as a Template
  A suitable quantity of DNA polymerase(s), capable of using an RNA primer(s), proof reading or not proof reading (for example and without limitation E. coli DNA Polymerase I), mixed with suitable buffer(s), and suitable dNTPs, is combined with the DNA/RNA ATO(s) mixture. In this example a total of 2.5 units of Klenow, 2 ul of 10× Klenow buffer, and 10 nmole of each dNTP (dATP/dTTP/dCTP/dGTP), is combined with the DNA-ATO mixture to a final volume of 20 ul.
  To further promote target nucleic acid and ATO(s) annealing in the presence of DNA polymerase(s) and buffer(s) in this example the mixture is incubated below 25° C. for 30 minutes, or other suitable temperatures or times capable of promoting annealing between nucleic acids and ATO(s). To initiate extension of the target polynucleotides using the ATO sequence as a template, in this example, the incubation temperate is increased to 37° C. for 30 minutes, or other suitable temperatures capable of promoting DNA polymerase activity. The product is a modified target polynucleotide.

Generating a Double Strand Target Ribonucleic Acid Extension Product
  As in example 5, except with the addition of 10 units of AMV Reverse Transcriptase as the polymerase.

Degradation of Adaptor Template Oligo(s) and Hairpin Degradation
  As in example 5.

One-pass extension or Linear Amplification of Double Strand Target Deoxyribonucleic and Ribonucleic Acid Extension Product(s)
  As in example 1, except 2.5 units of Tth DNA Polymerase, and Tth DNA Polymerase buffer are used, with an extension temperate of 70° C.

Annealing of a Third Adaptor Template Oligo to the extension or Linear Amplified Product(s)
  As in example 1, except ATO 1-022 is used.

Linear Extension Product Extension by its Use as a Primer with the Third Adaptor Template Oligo(s) as a Template to Form a Second Adaptor Template Extension Product
  As in example 1.

Degradation of Third Adaptor Template Oligo(s)
  As in example 1.

Exponential Amplification of Second Adaptor Template Extension Product by PCR
  As in example 1.

Results

Using a method similar to that in example 1 we were able to combine both RNA and DNA to produce a next generation sequencing library which includes UID suitable for removing PCR duplicates and for correcting errors for identifying low frequency mutations.

Conclusion

Being able to combine DNA and RNA to generate a mixed sequencing library, combined with the ability to separate during bioinformatic analysis the reads which originate with a DNA target polynucleotide and those which originate with an RNA target polynucleotide, allows for a host of potential applications, especially given the inherent nature of the technology to include UIDs for all target polynucleotides. For example, sequencing both RNA and DNA could allow for comparative mutation analysis. It is also possible to use different adaptors for the DNA and RNA ATO such that they can be differently amplified to increase the DNA copies in the final sequencing library.

Example 19

Using deoxyribonucleic acid (DNA) as the target polynucleotide for producing a template suitable for rolling circle amplification using an adaptor template oligo(s) with a hairpin (for example and without limitation, produced with two short regions of partial or complete complementarity separated by a random, specifically designed, or specifically chosen sequence), and a double strand adaptor joined with a hairpin.

Materials
  Target polynucleotide, human gDNA (BIO-35025)
  DNA fragmenting enzyme, KAPA Frag Kit (Roche, 7962517001)
  TAQ DNA polymerase (NEB, M0273L)
  TAQ DNA polymerase buffer (NEB, M0273L)
  DNA Polymerase I, Large (Klenow) Fragment (NEB, M0210L, M0212L)
  Adaptor template oligos (ATO), 1-013 (Table 1)
  dNTPs (NEB, N0447s)
  Phusion® High-Fidelity DNA Polymerase (NEB, M0530S)

Phusion buffer (NEB, M0530S)
USER® Enzyme (NEB, M5505S)
T4 DNA Ligase (NEB, M0202S)
Agencourt AMPure XP (Beckman Coulter, A63881)
Method
Annealing of Adaptor Template Oligo(s) to Deoxyribonucleic Acids
As in example 1.
Target Deoxyribonucleic Acid Extension by its Use as a Primer with the Adaptor Template Oligo(s) as a Template
As in example 1.
Generating a Double Strand Target Deoxyribonucleic Acid Extension Product
As in example 5.
Degradation of Adaptor Template Oligo(s)
As in example 1.
Annealing and Ligation of a Double Strand Adaptor(s) to the End of the Double Strand Target Deoxyribonucleic Acid Extension Product
As in example 5, with the addition that the adaptor forms a hairpin.
Results
Using a combination of an ATO which can form a hairpin and an adaptor with a hairpin we have successfully produced a circular modified target polynucleotide.
Conclusion
The ability to generate a circulate target polynucleotide allows for rolling circle amplification, which allows for generation of very long products which are necessary for certain downstream processes.

Example 20

Using deoxyribonucleic acid (DNA) as the target polynucleotide for producing a template suitable for rolling circle amplification using adaptor template oligo(s) with a hairpin produced using a chemical spacer (for example and without limitation, a C3 spacer, a C18 spacer), at least two adaptor template oligos need to be used which contain complementary regions which will be allowed to anneal producing short double strand DNA with an exposed 3' end to allow for extension.
Materials
Target polynucleotide, human gDNA (BIO-35025)
DNA fragmenting enzyme, KAPA Frag Kit (Roche, 7962517001)
TAQ DNA polymerase (NEB, M0273L)
TAQ DNA polymerase buffer (NEB, M0273L)
DNA Polymerase I, Large (Klenow) Fragment (NEB, M0210L, M0212L)
Adaptor template oligos (ATO), 1-034, 1-035 (Table 1)
dNTPs (NEB, N0447s)
Phusion® High-Fidelity DNA Polymerase (NEB, M0530S)
Phusion buffer (NEB, M0530S)
USER® Enzyme (NEB, M5505S)
Method
Annealing of Adaptor Template Oligo(s) to Deoxyribonucleic Acids
As in example one, with the addition of using ATO
Target Deoxyribonucleic Acid Extension by its Use as a Primer with the Adaptor Template Oligo(s) as a Template
As in example 1.
Degradation of Adaptor Template Oligo(s)
As in example 1.
One-Pass Extension or Linear Amplification of Modified Target Polynucleotide
As in example 1.
Annealing of a Second Adaptor Template Oligo(s) to First Complementary Strand
As in example one, with the addition of using ATO
First Complementary Strand Extension by its Use as a Primer with the Second Adaptor Template Oligo(s) as a Template to Form Modified First Complementary Strand
As in example 1.
Degradation of Second Adaptor Template Oligo(s)
As in example 1.
Self-Annealing of the Second Extension Product to Generate a Double Strand Region of DNA Whose 3' End Will Act as a Primer
The purified extension product is heated in a suitable buffer, at a suitable temperate, in this example 95° C., for a suitable time, in this example 2 minutes, or other temperatures or times which can result in denaturing of double strand nucleic acids to single strands. The extension products are subsequently cooled, in this example to 25° C. for 2 minutes, or other suitable temperatures, or times, capable of promoting annealing between the regions of complementarity present in the two ends of the extension products. The now circular DNA molecules can be used as a template for rolling circle amplification of the circular DNA.
Results
Similar to example 19 we have successfully produced a circular product whose 3' end can function as a priming site for further rolling circle amplification.
Conclusion
The ability to generate a circulate target polynucleotide allows for rolling circle amplification, which allows for generation of very long products which are necessary for certain downstream processes. The lack of the need of an additional primer means that competition with self-annealing of the circular DNA can be avoided.

Example 21

Using PCR products as the target polynucleotide for producing a single (or multiple) amplicon high diversity Next Generation Sequencing Library (for example and without limitation, compatible with Illumina Next Generation Sequencers) using for example and without limitation, adaptor template oligo(s) with a hairpin produced using a chemical spacer (for example and without limitation, a C3 spacer, a C18 spacer).
Materials
Adaptor template oligos (ATO), 1-014 (Table 1)
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
Phusion® High-Fidelity DNA Polymerase (NEB, M0530S)
Phusion buffer (NEB, M0530S)
USER® Enzyme (NEB, M5505S)
Primers 2-003 (Table 2)
Ammonium sulphate (SIGMA, A4418)
Agencourt AMPure XP (Beckman Coulter, A63881)
Method
Annealing of Adaptor Template Oligo(s) to PCR Products
As in example 1, except the target polynucleotide is a PCR product.

Target PCR Products Extension by its Use as a Primer with the Adaptor Template Oligo(s) as a Template
As in example 1.
Degradation of Adaptor Template Oligo(s)
As in example 1.
Exponential Amplification of Linear Extension Product by PCR for Generating a Final Sequencing Library
As in example 1, except for replacing one of the universal primers with a target specific primer with a 5' tail which contain sequences compatible and necessary with next generation sequencing technologies (for example and without limitation, P5 or P7 adaptor sequences, patient/sample index sequences, Illumina or custom read 1 or read 2 sequences for compatibility with Illumina Next Generation Sequencers).
Results
In a similar method to example one, we have successfully produced a next generation sequencing library using a single PCR amplicon as the target polynucleotide.
Conclusion
The ability to be able to use a PCR amplicon directly in the library, combined with the random priming seen by using an ATO means we are able to generate a high diversity sequencing library from a single amplicon, or pool of highly similar amplicons. This will have use for environmental samples where large numbers of highly similar amplicons are used.

Example 22

Using deoxyribonucleic acid (DNA) as the target polynucleotide for producing two Targeted Amplicon Next Generation Sequencing Libraries (for example and without limitation, compatible with Illumina Next Generation Sequencers)).
Materials
    Target polynucleotide, human gDNA (BIO-35025)
    DNA fragmenting enzyme, KAPA Frag Kit (Roche, 7962517001)
    Adaptor template oligos (ATO), 1-006 (Table 1)
    TAQ DNA polymerase (NEB, M0273L)
    TAQ DNA polymerase buffer (NEB, M0273L)
    DNA Polymerase I, Large (Klenow) Fragment (NEB, M0210L, M0212L)
    dNTPs (NEB, N0447s)
    Phusion® High-Fidelity DNA Polymerase (NEB, M0530S)
    Phusion buffer (NEB, M0530S)
    USER® Enzyme (NEB, M5505S)
    Primers, 2-004, 2-005 (Table 2)
    Ammonium sulfate (SIGMA, A4418)
    Agencourt AMPure XP (Beckman Coulter, A63881)
Method
Annealing of an Adaptor Template Oligo(s) to Deoxyribonucleic Acids
    As in example 1.
Target Deoxyribonucleic Acid Extension by its Use as a Primer with the Adaptor Template Oligo(s) as a Template
    As in example 1.
Degradation of Adaptor Template Oligo(s)
    As in example 1.
First Exponential Amplification of Adaptor Template Extension Product by PCR with two Different Pools of Target Specific Primers
    As in example 2, except the modified target polynucleotide is divided into two equal aliquots, this results in a reduction of all sensitivity as target polynucleotide copy number is reduced by approximately 50% in each subsequent reaction, each aliquot is combined with a universal primer complementary to the conserved sequence originally on the ATO(s) and now present on the 3' ends of the modified target DNA molecules, one of two different pools of primers (herein termed 'Pool1a' and 'Pool2a'), primers Pool1 are designed to target one DNA strand of the target regions of DNA which contains changes of interest, whereas Pool2 is designed to target the complementary strand of the target regions.
Second Exponential Amplification of First Exponential Amplification Product by PCR
    As in example 2, except two separate pools of nested primers are used, a pool of nested primers (Pool1b or Pool2b) designed to target regions of DNA relative to the first primer pool (Pool1a or Pool2a) which also target regions of DNA containing mutations of interest and also contains sequences compatible and necessary for compatibility with next generation sequencing technologies (for example and without limitation, P5 or P7 adaptor sequences, patient/sample index sequences, Illumina or custom read 1 or read 2 sequencing primer sites, for compatibility with Illumina Next Generation Sequencers).
Results
    We have successfully applied the method in example 2 to two separate pools of primers, where each pool of primers targets a single strand, the forward or the reverse. We have been able to show that all the primers in the pool are able to amplify their targets, with varying efficiency, and when generating barcode families see consistent efficiency across all targets.
Conclusion
    If you are happy to accept the reduced maximum efficiency by splitting the input target polynucleotide into two separate analysis pools you can interrogate both strands of the target polynucleotide independently, this allows you to compare identified mutations across both strands for an additional level of error correction and confidence that a mutation is correct, as you can find its presence on in both primer pools which greatly reduce the chance a mutation found in both pools is an error of any sort.

Example 23

Using deoxyribonucleic acid (DNA) as the target polynucleotide for producing two Targeted Amplicon Next Generation Sequencing Libraries (for example and without limitation, compatible with Illumina Next Generation Sequencers) while greatly reducing any possible loss of sensitivity,
Materials
    Target polynucleotide, human gDNA (BIO-35025)
    DNA fragmenting enzyme, KAPA Frag Kit (Roche, 7962517001)
    Adaptor template oligos (ATO), 1-006 (Table 1)
    TAQ DNA polymerase (NEB, M0273L)
    TAQ DNA polymerase buffer (NEB, M0273L)
    DNA Polymerase I, Large (Klenow) Fragment (NEB, M0210L, M0212L)
    dNTPs (NEB, N0447s)
    Phusion® High-Fidelity DNA Polymerase (NEB, M0530S)
    Phusion buffer (NEB, M0530S)
    USER® Enzyme (NEB, M5505S)
    Primers, 2-004, 2-005 (Table 2)
    Ammonium sulfate (SIGMA, A4418)
    Agencourt AMPure XP (Beckman Coulter, A63881)

Method
Annealing of an Adaptor Template Oligo(s) to Deoxyribonucleic Acids
As in example 1.
Target Deoxyribonucleic Acid Extension by its Use as a Primer with the Adaptor Template Oligo(s) as a Template
As in example 1.
Degradation of Adaptor Template Oligo(s)
As in example 1.
Linear Amplification of Modified Target Polynucleotide
As in example 1.
First Exponential Amplification of First Complementary Strand by PCR with Two Different Pools of Target Specific Primers Targeting Each Strand of the Duplex DNA
As in example 22, except that the first complementary strand is used as the template and split into two pools.
Second Exponential Amplification of First Exponential Amplification Product by PCR
As in example 22.
Results
As with example 2 and 22, we have successfully created a target amplicon next generation sequencing library.
Conclusion
Using the approach in this example, of linear amplification of the modified target polynucleotide, we can overcome the limitation of the method in example 22 as we amplify the original target polynucleotide, which is importantly, after the incorporation of UIDs. This means that 2 or more pools of strand specific amplification can be use with no theoretical drop in maximum efficiency for each of the pools.

Example 24

Using deoxyribonucleic acid (DNA) as the target polynucleotide for producing two Targeted Amplicon Next Generation Sequencing Libraries (for example and without limitation, compatible with Illumina Next Generation Sequencers) in one tube, using for example and without limitation, an adaptor template oligo(s) with a hairpin produced using a chemical spacer (for example and without limitation, a C3 spacer, a C18 spacer).
Materials
Target polynucleotide, human gDNA (BIO-35025)
DNA fragmenting enzyme, KAPA Frag Kit (Roche, 7962517001)
Adaptor template oligos (ATO), 1-006 (Table 1)
TAQ DNA polymerase (NEB, M0273L)
TAQ DNA polymerase buffer (NEB, M0273L)
DNA Polymerase I, Large (Klenow) Fragment (NEB, M0210L, M0212L)
dNTPs (NEB, N0447s)
Phusion® High-Fidelity DNA Polymerase (NEB, M0530S)
Phusion buffer (NEB, M0530S)
USER® Enzyme (NEB, M5505S)
Primers, 2-004, 2-005 (Table 2)
Ammonium sulfate (SIGMA, A4418)
Agencourt AMPure XP (Beckman Coulter, A63881)
Exonuclease I (NEB, M0293S)
Method
Annealing of an Adaptor Template Oligo(s) to Deoxyribonucleic Acids
As in example 1.
Target Deoxyribonucleic Acid Extension by its Use as a Primer with the Adaptor Template Oligo(s) as a Template
As in example 1.
Degradation of Adaptor Template Oligo(s)
As in example 1.
First Exponential Amplification of Adaptor Template Extension Product by PCR the First Pools of Target Specific Primers
As in example 2, with one of the two primer pools used in example 22.
Removal of Unused Primer from First Exponential Amplification Reaction Mixture
The first exponential amplification product is mixed with a single strand specific nuclease (for example exonuclease 1), at a temperate, for example 37° C., for a time, for example 15 minutes, or any other suitable time or temperature capable of resulting in enzyme activity resulting in degradation of all single strand DNA present in the exponential amplification product. In this example 20 units of Exonuclease I were added to the first amplification products and incubated at 37° C. for 25 minutes. The single strand specific nuclease can then be inactivated by incubating the reaction mixture at a temperature, in this example 80° C., for a time, in this example 15 minutes, capable of inactivating the single strand specific nuclease. Optionally, the amplification product can then be purified by any suitable method, for example using magnetic beads.
Second Exponential Amplification of Adaptor Template Extension Product by PCR the First Pools of Target Specific Primers
As with the first exponential amplification except a different, second, pool of target specific primers is used.
Removal of Unused Primer from Second Exponential Amplification Reaction Mixture
As with the first removal of unused primers.
Third Exponential Amplifications of Second Exponential Amplification Product by PCR
As the second exponential amplification in example 22, except the templates are the products of the second amplification products in this example which have been divided into two equal aliquots.
Results
As with example 2, 22 and 23, we have successfully created a target amplicon next generation sequencing library.
Conclusion
Using the approach in this example, of two sequential exponential amplifications, we can overcome the limitation of the method in example 22 as we amplify the original target polynucleotide, which is importantly, after the incorporation of UIDs. This means that 2 or more pools of strand specific amplification can be use with no theoretical drop in maximum efficiency for each of the pools.

Example 25

A cancer mutation hot spot panel was designed, containing 245×2 primer pairs. The Panel contains four pools of primers used to perform amplicon libraries from genomic "hot spot" regions that are frequently mutated in human cancer genes. The Hotspot Panel was designed to amplify 245 amplicons covering approximately 3,000 COSMIC mutations from 50 oncogenes and tumor suppressor genes.

| ABL1 | EZH2 | JAK3 | PTEN |
|---|---|---|---|
| AKT1 | FBXW7 | IDH2 | PTPN11 |
| ALK | FGFR1 | KDR | RB1 |
| APC | FGFR2 | KIT | RET |
| ATM | FGFR3 | KRAS | SMAD4 |
| BRAF | FLT3 | MET | SMARCB1 |
| CDH1 | GNA11 | MLH1 | SMO |

| | | | |
|---|---|---|---|
| CDKN2A | GNAS | MPL | SRC |
| CSF1R | GNAQ | NOTCH1 | STK11 |
| CTNNB1 | HNF1A | NPM1 | TP53 |
| EGFR | HRAS | NRAS | VHL |
| ERBB2 | IDH1 | PDGFRA | |
| ERBB4 | JAK2 | PIK3CA | |

Fp5 pool contains first set of forward primers, which are -target specific primers without tail;

Fp7 pool contains second set of forward primers, which are nested primers having the structure: 5' tail(universal)-target specific;

Rp5 pool contains first set of reverse primers, which are target specific primers without tail;

Rp7 pool contains second set of reverse primers, which are nested primers having the structure: 5' tail(universal)-target specific.

Each pool contains 245 primers.

In the first reaction, ATO are hybridised to the target polynucleotide sequences of a sample. The target polynucleotide is extended using ATO as template. The extension generates a modified target polynucleotide, which comprises a random sequence as UID and a 3' universal sequence. In the second reaction, the first universal primers and the Fp5 pool or Rp5 pool of target specific primers are added to hybridise to the modified target polynucleotide and PCR amplified the target sequences. A third reaction is carried out by using nested target specific primers (Fp7 or Rp7) and universal primers.

Each tagged amplicon library was subsequently purified from small residual DNA fragments and the DNA concentration determined. Next, these purified and individually tagged amplicon libraries were pooled equimolarly, resulting in an amplicon pool or sequencing sample.

All primers were synthesised by Eurofins or Eurogentec and were diluted to 10 uM. DNA polymerases were purchased from Promega, Thermo Fisher or NEB.

TABLE 1

Adaptor Template Oligos

| ID | Seq-ID | Sequence (5' to 3') |
|---|---|---|
| 1-001 | 1 | CTC TCT A76 G6C A67 C66 T6A 7NN NNN NNN NNN NNN NNN NNN NNN NG [PHO] |
| 1-002 | 2 | CTC TCT AT6 G6C A6T C66 T6A TNN NNN NNN NNN NNN NNN NNN NNN NG [PHO] |
| 1-003 | 3 | CTC TCT A[U][I] G[I]C A[I][U] C[I][I] T[I]A [U]NN NNN NNN NNN NNN NNN NNN NNN NG [SpC3] |
| 1-004a | 4 | CTC TC[U] A[U]G GGC AG[U] CGG [U]GA [U]NN NNN NNN NNN NNN NNN NNN NNN NG[SpC3] |
| 1-005 | 5 | CTC TC[U] A[U]G GGC AG[U] CGG [U]GA [U]NN NNN NNN NNN NNN NNN NNN NNA*C*A[SpC3] |
| 1-006 | 6 | ATC ACC GAC TG [SpC18] CTC TC[U] A[U]G GGC AG[U] CGG [U]GA [U]NN NNN NNN NNN NNN NNN NNN NNA*C*A [SpC3] |
| 1-007 | 7 | CTC TC8 A8G GGC AG8 CGG 8GA 8NN NNN NNN NNN NNN NNN NNN NN T*T*G [SpC3] |
| 1-008 | 8 | AGA [U]CG GA[U] GAG C [SpC18] TCA GAC GTG TGC TC[U] TCC GA[U] CTN NNN NNN NNN NNN NNN NNN NNN A*C*A [SpC3] |
| 1-009 | 9 | AGA [U]CG GA[U] GAG C [SpC18] CTA CAC GAC GCT CT[U] CCG A[U]C TNN NNN NNN NNN NNN NNN NNN NNA*C*A [SpC3] |
| 1-010 | 10 | CGN NAG A[U]C GGA [U]GA GC[SpC18] TCA GAC GTG TGC TC[U] TCC GA[U] C[U]N NCG NNN NNN NNN NNN NNN NNN NNN *G*T[SpC3] |
| 1-011 | 11 | CGN NTG [U]AG AA[U] CAT G[SpC18] ACA CTG ACG ACA TGG [U]TC [U]AC ANN CGN NNN NNN NNN NNN NNN NNN N*G*T[SpC3] |
| 1-012 | 12 | AGA [U]CG GA[U] GAG CTA ATA CGA CTC ACT ATA GTC AGA CGT GTG CTC [U]TC CGA [U]C[U] NNN NNN NNN NNN NNN N*G[SpC3] |
| 1-013 | 13 | AGA [U]CG GA[U] GAG C [SpC18] GTC TGA AAA AT CAG ACG TGT GCT C [U]TC CGA [U]C[U] NNN NNN NNN NNN NNN N*G[SpC3] |
| 1-004b | 14 | [PHO] ATC ACC GAC TGC CCA TAG AGA G [PHO] |
| 1-014 | 15 | NCG NNN AGA [U]CG GA[U] GAG C [SpC18] TCA GAC GTG TGC TC[U] TCC GA[U] C[U]N NNC GNN NNN NNN NNN NNN NN*T[SpC3] |

TABLE 1-continued

Adaptor Template Oligos

| ID | Seq-ID | Sequence (5' to 3') |
|---|---|---|
| 1-015 | 16 | NCA NNN AGA [U]CG GA[U] GAG C [SpC18] TCA GAC GTG TGC TC[U] TCC GA[U] C[U]N NNT GNN NNN NNN NNN NNN NN*A[SpC3] |
| 1-016 | 17 | NCC NNN AGA [U]CG GA[U] GAG C [SpC18] TCA GAC GTG TGC TC[U] TCC GA[U] C[U]N NNG GNN NNN NNN NNN NNN NN*C[SpC3] |
| 1-017 | 18 | NGG NNN AGA [U]CG GA[U] GAG C [SpC18] TCA GAC GTG TGC TC[U] TCC GA[U] C[U]N NNC CNN NNN NNN NNN NNN NN*G[SpC3] |
| 1-018 | 19 | AGA [U]CG GA[U] GAG C [SpC18] CTA CAC GAC GCT CT[U] CCG A[U]C TNN NNN NNN NNN NNN NNN NNN NN A*C*A [SpC3] |
| 1-019 | 20 | AGA [U]CG GA[U] [SpC18] GAG CTA ATA CGA CTC ACT ATA GTC AGA CGT GTG CTC [U]TC CGA [U]C[U] NNN NNN NNN NNN NNN N*G[SpC3] |
| 1-020 | 21 | GAT GAG CTA ATA CGA CTC ACT ATA GTC AGA CGT GTG CTC TTC CGA TCT |
| 1-021 | 22 | AGA [U]CG CTA [U] [SpC18] GTC TGA AAA AAT CAG ACC TC[U] TCG AGC TAA TAC GAC TCA CTA TAG CGA [U]C[U] NNN NNN NNN NNN NNN N*G[SpC3] |
| 1-022 | 23 | AGA [U]CG GA[U] GAG C [SpC18] GTC TGA AAA AAT CAG ACC TAC ACG ACG CTC T[U]C CGA [U]CT NNN NNN NNN NNN NNN NNN NNN N A*C*A [SpC3] |
| 1-023 | 24 | AGA TCG GAA GAG CAC AAA AAA AAA AAA CAA GCA GAA GAC GGC A[U]A CGA GAT CG[U] GAT GTG AC[U] GGA GTT CAG ACG [U]GT GCT C[U]T CCG AT*C*T NNN NNN NNN NNN NNN NNN NNN N A*C*A [SpC3] |
| 1-024 | 25 | AGA TCG GAA GAG CAC A[SpC18] CAA GCA GAA GAC GGC A[U]A CGA GAT CG[U] GAT GTG AC[U] GGA GTT CAG ACG [U]GT GCT C[U]T CCG AT*C*T NNN NNN NNN NNN NNN NNN NNN N A*C*A [SpC3] |
| 1-025 | 26 | TCA GAC GTG TGC TC[U] TCC GA[U] C[U]N NNC GNN NNN NNN NNN NN*T[SpC3] |
| 1-026 | 27 | CTA CAC GAC GCT CT[U] CCG A[U]C TNN NNN NNN NNN NNN NNN NN A*C*A [SpC3] |
| 1-027 | 28 | TCA GAC G[U]G TGC TC[U] TCC GAT C[U]NN NNN NNN NNN NNN NN*T[SpC3] |
| 1-028 | 29 | [PHO]AGA TCG GAA GAG CAC ACG TCT GA[PHO] |
| 1-029 | 30 | CTA CAC GAC GCT CT[U] CCG A[U]C TNN NNN NNN NNN NNN NNN NN A*C*A [SpC3] |
| 1-030 | 31 | [PHO]AGA TCG GAA GAG CGT CGT GTA G[PHO] |
| 1-031 | 32 | rArGrA rTrCrG rGrArT rGrArG rC [SpC18] rTrCrA rGrArC rGrTrG rTrGrC rTrCrT rTrCrC rGrArT rCrTrNrN rNrNrN rNrNrN rNrNrN rNrNrN rNrN*rT[SpC3] |
| 1-032 | 33 | rArGrA rTrCrG rGrArT rGrArG rC [SpC18] rCrTrA rCrArC rGrArC rGrCrT rCrTrT rCrCrG rArTrC rTrNrN rNrNrN rNrNrN rNrNrN rNrNrN rNrNrN rNrN rA*rC*rA [SpC3] |
| 1-033 | 34 | CGA AGA [U]CG GA[U] GAG C [SpC18] GTC TGA AAA AAT CAG ACG TGT GCT C [U]TC CGA [U]C[U] TCG NNN NNN NNN NNN NNN N*G[SpC3] |
| 1-034 | 35 | AGA [U]CG GA[U] GAG C [SpC18] GCT C[U]T CCG A[U]C [U]NN NNN NNN NNN NNN NN*T[SpC3] |

TABLE 1-continued

Adaptor Template Oligos

| ID | Seq-ID | Sequence (5' to 3') |
|---|---|---|
| 1-035 | 36 | TC[U] AGC CTA C[U]C G [SpC18] [U]C[U] AGC CT[U] CTC GNN NNN NNN NNN NNN NN*T[SpC3] |
| 1-036 | 37 | GTC AGA [U]CG GA[U] GAG C [SpC18] GTC TGA AAA AAT CAG ACG TGT GCT C [U]TC CGA [U]C[U] GAC NNN NNN NNN NNN NNN N*G[SpC3] |

Key
*= Phosphorothioate linkage
[PHO]= 5' or 3' phosphate group
[U]= 2'-Desoxyuridine
[I]= 2'-Desoxyinosine
[SpC3]= Spacer C3
[SpC18]= Spacer C18
6= G, Locked Nucleic Acid (LNA®)
7= T, Locked Nucleic Acid (LNA®)
8= Locked Nucleic Acid (LNA®)
N= A, T, C, or G
r= A lower case 'r' preceding a nucleotide indicates an RNA nucleotide.

TABLE 2

Primer Sequences

| ID | Seq-ID | Sequence |
|---|---|---|
| 2-001 | 38 | GTG ACT GGA GTT CAG ACG TGT GCT CTT CCG*A |
| 2-002 | 39 | AAT GAT ACG GCG ACC ACC GAG ATC TAC ACT CTT TCC CTA CAC GAC GCT CTT CCG ATC T |
| 2-003 | 40 | CAA GCA GAA GAC GGC ATA CGA GAT CGT GAT GTG ACT GGA GTT CAG ACG TGT GCT CTT CCG AT*C*T |
| 2-004 | 41 | AAC CTC TCT ATG GGC AGT CGG T |
| 2-005 | 42 | CAA GCA GAA GAC GGC ATA CGA GAT CGT GAT GAC GCT CTC CTC TCT ATG GGC AGT CGG TG*A*T |
| 2-006 | 43 | [Spc3]CAA GCA GAA GAC GGC ATA CGA GAT |

Key
*= Phosphorothioate linkage

The invention claimed is:

1. A method for extending a population of target polynucleotides comprising:
   (i) incubating the target polynucleotides with adaptor template oligonucleotides (ATO) having
      (a) a 3' random sequence;
      (b) a 3' end with a blocker, which renders ATO non-extendible;
      (c) a nucleotide sequence comprising an inosine or deoxyinosine moiety; and
      (d) a universal sequence, 5' to the random sequence, wherein the target polynucleotides hybridise to the 3' random sequence of the ATO;
   (ii) performing a polymerase extension of the target polynucleotides using the ATO as a template, thereby producing extended target polynucleotides having a 3' universal sequence;

(iii) digesting the ATO using an endonuclease that recognizes the nucleotide sequence (c); and (iv) generating a first complement sequence (CS), wherein generating the first CS comprises polymerase extension from the 3' universal sequence using the target polynucleotides as templates.

2. The method according to claim 1, wherein the polymerase extension to produce the first CS comprises extending a primer hybridised to the 3' universal sequence.

3. The method according to claim 1, wherein the first CS is extended to produce extended first complementary sequences having a 3' universal sequence.

4. The method according to claim 1, wherein the first CS is extended using a DNA ligase to ligate adaptors to the first CS.

5. The method according to claim 1, further comprising extending a primer hybridized to the first CS or modified first CS, thereby forming a second CS, wherein the primer hybridized to the first CS or modified first CS comprises a target-specific portion, or universal sequence, or both a 3' target specific and a 5' universal sequence.

6. The method according to claim 1, wherein the polymerase used in step (ii) has 3' to 5' exonuclease activity.

7. A method for preparing a sequencing library from a population of single stranded nucleic acids, the method comprising;

(a) performing the method according to claim 1 to produce first complementary sequences;

(b) generating second complementary sequences having a 5' universal sequence and a 3' universal sequence, wherein the 5' universal sequence and 3' universal sequences are different and not complementary to each other; and (c) amplifying the first and second complementary sequences using primers targeting the 5' universal sequence and a 3' universal sequence, thereby preparing a sequencing library of double stranded nucleic acid fragments having known universal ends of different sequence.

8. The method according to claim 1, wherein the target polynucleotides are derived from an FFPE sample, circulating cell free nucleic acid or a sample treated with bisulfite.

9. The method according to claim 2, wherein the extension of the primer hybridised to the 3' universal sequence is repeated as linear amplification.

10. The method according to claim 1, wherein the adaptor template oligonucleotides (ATO) comprise a 3' random sequence of 3 to 36 'N' bases.

11. The method according to claim 1, wherein the universal sequence comprises a sequence capable of acting as an RNA polymerase promoter.

12. The method according to claim 1, wherein the ATO comprises in 5' to 3' order: a 5' stem portion, an RNA polymerase sequence, a priming site sequence, a single stranded overhanging 3' random sequence and a 3' end with a blocker.

13. The method according to claim 1, wherein the ATO comprises a stem-loop structure containing a non-copiable linkage selected from a C3 Spacer, a triethylene glycol spacer, an 18-atom hexa-ethyleneglycol spacer, or 1',2'-Dideoxyribose (dSpacer).

14. The method according to claim 1, wherein the 3' end of the ATO is blocked with a moiety selected from the group consisting of at least one ribonucleotide, at least one deoxynucleotide, a C3 spacer, a phosphate, a dideoxynucleotide, an amino group, and an inverted deoxythymidine.

15. The method according to claim 1, wherein the ATO comprises a random sequence which functions as a template for a unique identifier (UID) once copied to the target polynucleotides.

16. The method according to claim 1, wherein the endonuclease is hypoxanthine-N-glycosylase.

* * * * *

SEQUENCE LISTING

```
Sequence total quantity: 44
SEQ ID NO: 1          moltype = DNA  length = 47
FEATURE               Location/Qualifiers
modified_base         8..9
                      mod_base = OTHER
                      note = Locked nucleic acid
modified_base         11
                      mod_base = OTHER
                      note = Locked nucleic acid
modified_base         14..15
                      mod_base = OTHER
                      note = Locked nucleic acid
modified_base         17..18
                      mod_base = OTHER
                      note = Locked nucleic acid
modified_base         20
                      mod_base = OTHER
                      note = Locked nucleic acid
modified_base         22
                      mod_base = OTHER
                      note = Locked nucleic acid
source                1..47
                      mol_type = other DNA
                      organism = synthetic construct
```

```
                        misc_feature     47
                                         note = 3' Phosphate
SEQUENCE: 1
ctctctatgg gcagtcggtg atnnnnnnnn nnnnnnnnnn nnnnnng                  47

SEQ ID NO: 2             moltype = DNA   length = 47
FEATURE                  Location/Qualifiers
modified_base            9
                         mod_base = OTHER
                         note = Locked nucleic acid
modified_base            11
                         mod_base = OTHER
                         note = Locked nucleic acid
modified_base            14
                         mod_base = OTHER
                         note = Locked nucleic acid
modified_base            17..18
                         mod_base = OTHER
                         note = Locked nucleic acid
modified_base            20
                         mod_base = OTHER
                         note = Locked nucleic acid
source                   1..47
                         mol_type = other DNA
                         organism = synthetic construct
misc_feature             47
                         note = 3' Phosphate
SEQUENCE: 2
ctctctatgg gcagtcggtg atnnnnnnnn nnnnnnnnnn nnnnnng                  47

SEQ ID NO: 3             moltype = DNA   length = 47
FEATURE                  Location/Qualifiers
modified_base            9
                         mod_base = OTHER
                         note = 2'-Desoxyinosine
modified_base            11
                         mod_base = OTHER
                         note = 2'-Desoxyinosine
modified_base            14
                         mod_base = OTHER
                         note = 2'-Desoxyinosine
modified_base            17..18
                         mod_base = OTHER
                         note = 2'-Desoxyinosine
modified_base            20
                         mod_base = OTHER
                         note = 2'-Desoxyinosine
source                   1..47
                         mol_type = other DNA
                         organism = synthetic construct
modified_base            8
                         mod_base = OTHER
                         note = 2'-Desoxyuridine
modified_base            15
                         mod_base = OTHER
                         note = 2'-Desoxyuridine
modified_base            22
                         mod_base = OTHER
                         note = 2'-Desoxyuridine
misc_feature             47
                         note = 3' C3 Spacer
SEQUENCE: 3
ctctctanng ncanncnntn annnnnnnnn nnnnnnnnnn nnnnnng                  47

SEQ ID NO: 4             moltype = DNA   length = 47
FEATURE                  Location/Qualifiers
source                   1..47
                         mol_type = other DNA
                         organism = synthetic construct
modified_base            6
                         mod_base = OTHER
                         note = 2'-Desoxyuridine
modified_base            8
                         mod_base = OTHER
                         note = 2'-Desoxyuridine
modified_base            15
                         mod_base = OTHER
                         note = 2'-Desoxyuridine
```

```
modified_base         19
                      mod_base = OTHER
                      note = 2'-Desoxyuridine
modified_base         22
                      mod_base = OTHER
                      note = 2'-Desoxyuridine
misc_feature          47
                      note = 3' C3 Spacer
SEQUENCE: 4
ctctcnangg gcagncggng annnnnnnnn nnnnnnnnnn nnnnnng                        47

SEQ ID NO: 5          moltype = DNA   length = 47
FEATURE               Location/Qualifiers
source                1..47
                      mol_type = other DNA
                      organism = synthetic construct
modified_base         45^46
                      mod_base = OTHER
                      note = Phosphorothioate bond
modified_base         46^47
                      mod_base = OTHER
                      note = Phosphorothioate bond
modified_base         6
                      mod_base = OTHER
                      note = 2'-Desoxyuridine
modified_base         8
                      mod_base = OTHER
                      note = 2'-Desoxyuridine
modified_base         15
                      mod_base = OTHER
                      note = 2'-Desoxyuridine
modified_base         19
                      mod_base = OTHER
                      note = 2'-Desoxyuridine
modified_base         22
                      mod_base = OTHER
                      note = 2'-Desoxyuridine
misc_feature          47
                      note = 3' C3 Spacer
SEQUENCE: 5
ctctcnangg gcagncggng annnnnnnnn nnnnnnnnnn nnnnaca                        47

SEQ ID NO: 6          moltype = DNA   length = 58
FEATURE               Location/Qualifiers
source                1..58
                      mol_type = other DNA
                      organism = synthetic construct
misc_feature          11^12
                      note = C18 spacer between residues
modified_base         17
                      mod_base = OTHER
                      note = 2'-Desoxyuridine
modified_base         19
                      mod_base = OTHER
                      note = 2'-Desoxyuridine
modified_base         26
                      mod_base = OTHER
                      note = 2'-Desoxyuridine
modified_base         30
                      mod_base = OTHER
                      note = 2'-Desoxyuridine
modified_base         33
                      mod_base = OTHER
                      note = 2'-Desoxyuridine
modified_base         56^57
                      mod_base = OTHER
                      note = Phosphorothioate bond
modified_base         57^58
                      mod_base = OTHER
                      note = Phosphorothioate bond
misc_feature          58
                      note = 3' C3 Spacer
SEQUENCE: 6
atcaccgact gctctcnang ggcagncggn gannnnnnnn nnnnnnnnnn nnnnnaca            58

SEQ ID NO: 7          moltype = DNA   length = 47
FEATURE               Location/Qualifiers
modified_base         6
                      mod_base = OTHER
```

```
                           note = Locked nucleic acid
modified_base              8
                           mod_base = OTHER
                           note = Locked nucleic acid
modified_base              15
                           mod_base = OTHER
                           note = Locked nucleic acid
modified_base              19
                           mod_base = OTHER
                           note = Locked nucleic acid
modified_base              22
                           mod_base = OTHER
                           note = Locked nucleic acid
source                     1..47
                           mol_type = other DNA
                           organism = synthetic construct
modified_base              45^46
                           mod_base = OTHER
                           note = Phosphorothioate bond
modified_base              46^47
                           mod_base = OTHER
                           note = Phosphorothioate bond
misc_feature               47
                           note = 3' C3 Spacer
SEQUENCE: 7
ctctcnangg gcagncggng annnnnnnnn nnnnnnnnnn nnnnttg                         47

SEQ ID NO: 8               moltype = DNA  length = 61
FEATURE                    Location/Qualifiers
source                     1..61
                           mol_type = other DNA
                           organism = synthetic construct
modified_base              59^60
                           mod_base = OTHER
                           note = Phosphorothioate bond
modified_base              60^61
                           mod_base = OTHER
                           note = Phosphorothioate bond
modified_base              4
                           mod_base = OTHER
                           note = 2'-Desoxyuridine
misc_feature               61
                           note = 3' C3 Spacer
misc_feature               13^14
                           note = C18 Spacer between residues
modified_base              9
                           mod_base = OTHER
                           note = 2'-Desoxyuridine
modified_base              28
                           mod_base = OTHER
                           note = 2'-Desoxyuridine
modified_base              34
                           mod_base = OTHER
                           note = 2'-Desoxyuridine
SEQUENCE: 8
agancggang agctcagacg tgtgctcntc cganctnnnn nnnnnnnnnn nnnnnnnnac           60
a                                                                          61

SEQ ID NO: 9               moltype = DNA  length = 60
FEATURE                    Location/Qualifiers
source                     1..60
                           mol_type = other DNA
                           organism = synthetic construct
modified_base              4
                           mod_base = OTHER
                           note = 2'-Desoxyuridine
modified_base              9
                           mod_base = OTHER
                           note = 2'-Desoxyuridine
modified_base              28
                           mod_base = OTHER
                           note = 2'-Desoxyuridine
modified_base              33
                           mod_base = OTHER
                           note = 2'-Desoxyuridine
modified_base              58^59
                           mod_base = OTHER
                           note = Phosphorothioate bond
modified_base              59^60
```

|  |  |
|---|---|
|  | mod_base = OTHER |
|  | note = Phosphorothioate bond |
| misc_feature | 13^14 |
|  | note = C18 Spacer between residues |
| misc_feature | 60 |
|  | note = 3' C3 Spacer |

SEQUENCE: 9 agancggang agcctacacg acgctctncc ganctnnnnn nnnnnnnnnn nnnnnnnaca 60

|  |  |
|---|---|
| SEQ ID NO: 10 | moltype = DNA   length = 67 |
| FEATURE | Location/Qualifiers |
| source | 1..67 |
|  | mol_type = other DNA |
|  | organism = synthetic construct |
| misc_feature | 67 |
|  | note = 3' C3 Spacer |
| misc_feature | 17^18 |
|  | note = C18 Spacer between residues |
| modified_base | 65^66 |
|  | mod_base = OTHER |
|  | note = Phosphorothioate bond |
| modified_base | 66^67 |
|  | mod_base = OTHER |
|  | note = Phosphorothioate bond |
| modified_base | 8 |
|  | mod_base = OTHER |
|  | note = 2'-Desoxyuridine |
| modified_base | 13 |
|  | mod_base = OTHER |
|  | note = 2'-Desoxyuridine |
| modified_base | 32 |
|  | mod_base = OTHER |
|  | note = 2'-Desoxyuridine |
| modified_base | 38 |
|  | mod_base = OTHER |
|  | note = 2'-Desoxyuridine |
| modified_base | 40 |
|  | mod_base = OTHER |
|  | note = 2'-Desoxyuridine |

SEQUENCE: 10 cgnnagancg gangagctca gacgtgtgct cntccgancn nncgnnnnnn nnnnnnnnnn 60
nnnnngt                                                          67

|  |  |
|---|---|
| SEQ ID NO: 11 | moltype = DNA   length = 64 |
| FEATURE | Location/Qualifiers |
| source | 1..64 |
|  | mol_type = other DNA |
|  | organism = synthetic construct |
| modified_base | 7 |
|  | mod_base = OTHER |
|  | note = 2'-Desoxyuridine |
| modified_base | 12 |
|  | mod_base = OTHER |
|  | note = 2'-Desoxyuridine |
| modified_base | 32 |
|  | mod_base = OTHER |
|  | note = 2'-Desoxyuridine |
| modified_base | 35 |
|  | mod_base = OTHER |
|  | note = 2'-Desoxyuridine |
| modified_base | 62^63 |
|  | mod_base = OTHER |
|  | note = Phosphorothioate bond |
| modified_base | 63^64 |
|  | mod_base = OTHER |
|  | note = Phosphorothioate bond |
| misc_feature | 64 |
|  | note = 3' C3 Spacer |
| misc_feature | 16^17 |
|  | note = C18 Spacer between residues |

SEQUENCE: 11 cgnntgnaga ancatgacac tgacgacatg gntcnacann cgnnnnnnnn nnnnnnnnnn 60
nngt                                                             64

|  |  |
|---|---|
| SEQ ID NO: 12 | moltype = DNA   length = 71 |
| FEATURE | Location/Qualifiers |
| source | 1..71 |
|  | mol_type = other DNA |
|  | organism = synthetic construct |

```
modified_base      4
                   mod_base = OTHER
                   note = 2'-Desoxyuridine
modified_base      9
                   mod_base = OTHER
                   note = 2'-Desoxyuridine
modified_base      46
                   mod_base = OTHER
                   note = 2'-Desoxyuridine
modified_base      52
                   mod_base = OTHER
                   note = 2'-Desoxyuridine
modified_base      54
                   mod_base = OTHER
                   note = 2'-Desoxyuridine
modified_base      70^71
                   mod_base = OTHER
                   note = Phosphorothioate bond
misc_feature       71
                   note = 3' C3 Spacer
SEQUENCE: 12
agancggang agctaatacg actcactata gtcagacgtg tgctcntccg ancnnnnnnn    60
nnnnnnnnnn g                                                         71

SEQ ID NO: 13      moltype = DNA  length = 64
FEATURE            Location/Qualifiers
source             1..64
                   mol_type = other DNA
                   organism = synthetic construct
modified_base      4
                   mod_base = OTHER
                   note = 2'-Desoxyuridine
modified_base      9
                   mod_base = OTHER
                   note = 2'-Desoxyuridine
modified_base      39
                   mod_base = OTHER
                   note = 2'-Desoxyuridine
modified_base      45
                   mod_base = OTHER
                   note = 2'-Desoxyuridine
modified_base      47
                   mod_base = OTHER
                   note = 2'-Desoxyuridine
modified_base      63^64
                   mod_base = OTHER
                   note = Phosphorothioate bond
misc_feature       64
                   note = 3' C3 Spacer
misc_feature       13^14
                   note = C18 Spacer between residues
SEQUENCE: 13
agancggang agcgtctgaa aaaatcagac gtgtgctcnt ccgancnnnn nnnnnnnnnn    60
nnng                                                                 64

SEQ ID NO: 14      moltype = DNA  length = 22
FEATURE            Location/Qualifiers
source             1..22
                   mol_type = other DNA
                   organism = synthetic construct
misc_feature
                   note = 5' Phosphate
misc_feature       22
                   note = 3' Phosphate
SEQUENCE: 14
atcaccgact gcccatagag ag                                             22

SEQ ID NO: 15      moltype = DNA  length = 64
FEATURE            Location/Qualifiers
source             1..64
                   mol_type = other DNA
                   organism = synthetic construct
modified_base      10
                   mod_base = OTHER
                   note = 2'-Desoxyuridine
modified_base      15
                   mod_base = OTHER
                   note = 2'-Desoxyuridine
modified_base      34
```

```
                        mod_base = OTHER
                        note = 2'-Desoxyuridine
modified_base           40
                        mod_base = OTHER
                        note = 2'-Desoxyuridine
modified_base           42
                        mod_base = OTHER
                        note = 2'-Desoxyuridine
modified_base           63^64
                        mod_base = OTHER
                        note = Phosphorothioate bond
misc_feature            64
                        note = 3' C3 Spacer
misc_feature            19^20
                        note = C18 Spacer between residues
SEQUENCE: 15
ncgnnnagan cggangagct cagacgtgtg ctcntccgan cnnnncgnnn nnnnnnnnnn    60
nnnt                                                                64

SEQ ID NO: 16           moltype = DNA  length = 64
FEATURE                 Location/Qualifiers
source                  1..64
                        mol_type = other DNA
                        organism = synthetic construct
modified_base           10
                        mod_base = OTHER
                        note = 2'-Desoxyuridine
modified_base           15
                        mod_base = OTHER
                        note = 2'-Desoxyuridine
modified_base           34
                        mod_base = OTHER
                        note = 2'-Desoxyuridine
modified_base           40
                        mod_base = OTHER
                        note = 2'-Desoxyuridine
modified_base           42
                        mod_base = OTHER
                        note = 2'-Desoxyuridine
modified_base           63^64
                        mod_base = OTHER
                        note = Phosphorothioate bond
misc_feature            64
                        note = 3' C3 Spacer
misc_feature            19^20
                        note = C18 Spacer between residues
SEQUENCE: 16
ncannnagan cggangagct cagacgtgtg ctcntccgan cnnnntgnnn nnnnnnnnnn    60
nnna                                                                64

SEQ ID NO: 17           moltype = DNA  length = 64
FEATURE                 Location/Qualifiers
source                  1..64
                        mol_type = other DNA
                        organism = synthetic construct
modified_base           10
                        mod_base = OTHER
                        note = 2'-Desoxyuridine
modified_base           15
                        mod_base = OTHER
                        note = 2'-Desoxyuridine
modified_base           34
                        mod_base = OTHER
                        note = 2'-Desoxyuridine
modified_base           40
                        mod_base = OTHER
                        note = 2'-Desoxyuridine
modified_base           42
                        mod_base = OTHER
                        note = 2'-Desoxyuridine
modified_base           63^64
                        mod_base = OTHER
                        note = Phosphorothioate bond
misc_feature            64
                        note = 3' C3 Spacer
misc_feature            19^20
                        note = C18 Spacer between residues
SEQUENCE: 17
nccnnnagan cggangagct cagacgtgtg ctcntccgan cnnnnggnnn nnnnnnnnnn    60
```

```
nnnc                                                                  64

SEQ ID NO: 18           moltype = DNA  length = 64
FEATURE                 Location/Qualifiers
source                  1..64
                        mol_type = other DNA
                        organism = synthetic construct
modified_base           10
                        mod_base = OTHER
                        note = 2'-Desoxyuridine
modified_base           15
                        mod_base = OTHER
                        note = 2'-Desoxyuridine
modified_base           34
                        mod_base = OTHER
                        note = 2'-Desoxyuridine
modified_base           40
                        mod_base = OTHER
                        note = 2'-Desoxyuridine
modified_base           42
                        mod_base = OTHER
                        note = 2'-Desoxyuridine
modified_base           63^64
                        mod_base = OTHER
                        note = Phosphorothioate bond
misc_feature            64
                        note = 3' C3 Spacer
misc_feature            19^20
                        note = C18 Spacer between residues
SEQUENCE: 18
nggnnnagan cggangagct cagacgtgtg ctcntccgan cnnnnccnnn nnnnnnnnnn    60
nnng                                                                  64

SEQ ID NO: 19           moltype = DNA  length = 60
FEATURE                 Location/Qualifiers
source                  1..60
                        mol_type = other DNA
                        organism = synthetic construct
modified_base           4
                        mod_base = OTHER
                        note = 2'-Desoxyuridine
modified_base           9
                        mod_base = OTHER
                        note = 2'-Desoxyuridine
modified_base           28
                        mod_base = OTHER
                        note = 2'-Desoxyuridine
modified_base           33
                        mod_base = OTHER
                        note = 2'-Desoxyuridine
modified_base           58^59
                        mod_base = OTHER
                        note = Phosphorothioate bond
modified_base           59^60
                        mod_base = OTHER
                        note = Phosphorothioate bond
misc_feature            60
                        note = 3' C3 Spacer
misc_feature            13^14
                        note = C18 Spacer between residues
SEQUENCE: 19
agancggang agcctacacg acgtctctncc ganctnnnnn nnnnnnnnnn nnnnnnnaca    60

SEQ ID NO: 20           moltype = DNA  length = 71
FEATURE                 Location/Qualifiers
source                  1..71
                        mol_type = other DNA
                        organism = synthetic construct
modified_base           4
                        mod_base = OTHER
                        note = 2'-Desoxyuridine
modified_base           9
                        mod_base = OTHER
                        note = 2'-Desoxyuridine
modified_base           46
                        mod_base = OTHER
                        note = 2'-Desoxyuridine
modified_base           52
                        mod_base = OTHER
```

```
                        note = 2'-Desoxyuridine
modified_base           54
                        mod_base = OTHER
                        note = 2'-Desoxyuridine
modified_base           70^71
                        mod_base = OTHER
                        note = Phosphorothioate bond
misc_feature            71
                        note = 3' C3 Spacer
misc_feature            9^10
                        note = C18 Spacer between residues
SEQUENCE: 20
agancggang agctaatacg actcactata gtcagacgtg tgctcntccg ancnnnnnnn   60
nnnnnnnnnn g                                                       71

SEQ ID NO: 21           moltype = DNA   length = 48
FEATURE                 Location/Qualifiers
source                  1..48
                        mol_type = other DNA
                        organism = synthetic construct
SEQUENCE: 21
gatgagctaa tacgactcac tatagtcaga cgtgtgctct tccgatct               48

SEQ ID NO: 22           moltype = DNA   length = 78
FEATURE                 Location/Qualifiers
source                  1..78
                        mol_type = other DNA
                        organism = synthetic construct
modified_base           4
                        mod_base = OTHER
                        note = 2'-Desoxyuridine
modified_base           10
                        mod_base = OTHER
                        note = 2'-Desoxyuridine
modified_base           31
                        mod_base = OTHER
                        note = 2'-Desoxyuridine
modified_base           58
                        mod_base = OTHER
                        note = 2'-Desoxyuridine
modified_base           61
                        mod_base = OTHER
                        note = 2'-Desoxyuridine
modified_base           77^78
                        mod_base = OTHER
                        note = Phosphorothioate bond
misc_feature            78
                        note = 3' C3 Spacer
misc_feature            10^11
                        note = C18 Spacer between residues
SEQUENCE: 22
agancgctan gtctgaaaaa atcagacctc ntcgagctaa tacgactcac tatagcganc   60
nnnnnnnnnn nnnnnnng                                                78

SEQ ID NO: 23           moltype = DNA   length = 77
FEATURE                 Location/Qualifiers
source                  1..77
                        mol_type = other DNA
                        organism = synthetic construct
modified_base           4
                        mod_base = OTHER
                        note = 2'-Desoxyuridine
modified_base           9
                        mod_base = OTHER
                        note = 2'-Desoxyuridine
modified_base           45
                        mod_base = OTHER
                        note = 2'-Desoxyuridine
modified_base           50
                        mod_base = OTHER
                        note = 2'-Desoxyuridine
modified_base           76^77
                        mod_base = OTHER
                        note = Phosphorothioate bond
misc_feature            77
                        note = 3' C3 Spacer
misc_feature            13^14
                        note = C18 Spacer between residues
modified_base           75^76
```

```
                              mod_base = OTHER
                              note = Phosphorothioate bond
SEQUENCE: 23
agancggang agcgtctgaa aaaatcagac ctacacgacg ctctnccgan ctnnnnnnn      60
nnnnnnnnnn nnnaca                                                    77

SEQ ID NO: 24              moltype = DNA  length = 116
FEATURE                    Location/Qualifiers
source                     1..116
                              mol_type = other DNA
                              organism = synthetic construct
modified_base              44
                              mod_base = OTHER
                              note = 2'-Desoxyuridine
modified_base              54
                              mod_base = OTHER
                              note = 2'-Desoxyuridine
modified_base              63
                              mod_base = OTHER
                              note = 2'-Desoxyuridine
modified_base              76
                              mod_base = OTHER
                              note = 2'-Desoxyuridine
modified_base              83
                              mod_base = OTHER
                              note = 2'-Desoxyuridine
modified_base              114^115
                              mod_base = OTHER
                              note = Phosphorothioate bond
modified_base              115^116
                              mod_base = OTHER
                              note = Phosphorothioate bond
misc_feature               116
                              note = 3' C3 Spacer
modified_base              89^90
                              mod_base = OTHER
                              note = Phosphorothioate bond
modified_base              90^91
                              mod_base = OTHER
                              note = Phosphorothioate bond
SEQUENCE: 24
agatcggaag agcacaaaaa aaaaaaacaa gcagaagacg gcanacgaga tcgngatgtg    60
acnggagttc agacgngtgc tcntccgatc tnnnnnnnnn nnnnnnnnnn nnnaca       116

SEQ ID NO: 25              moltype = DNA  length = 105
FEATURE                    Location/Qualifiers
source                     1..105
                              mol_type = other DNA
                              organism = synthetic construct
misc_feature               16^17
                              note = C18 Spacer between residues
modified_base              33
                              mod_base = OTHER
                              note = 2'-Desoxyuridine
modified_base              43
                              mod_base = OTHER
                              note = 2'-Desoxyuridine
modified_base              52
                              mod_base = OTHER
                              note = 2'-Desoxyuridine
modified_base              65
                              mod_base = OTHER
                              note = 2'-Desoxyuridine
modified_base              72
                              mod_base = OTHER
                              note = 2'-Desoxyuridine
modified_base              78^79
                              mod_base = OTHER
                              note = Phosphorothioate bond
modified_base              79^80
                              mod_base = OTHER
                              note = Phosphorothioate bond
misc_feature               105
                              note = 3' C3 Spacer
modified_base              103^104
                              mod_base = OTHER
                              note = Phosphorothioate bond
modified_base              104^105
                              mod_base = OTHER
```

```
                        note = Phosphorothioate bond
SEQUENCE: 25
agatcggaag agcacacaag cagaagacgg canacgagat cgngatgtga cnggagttca    60
gacgngtgct cntccgatct nnnnnnnnnn nnnnnnnnnn nnaca                  105

SEQ ID NO: 29           moltype = DNA   length = 45
FEATURE                 Location/Qualifiers
source                  1..45
                        mol_type = other DNA
                        organism = synthetic construct
modified_base           15
                        mod_base = OTHER
                        note = 2'-Desoxyuridine
modified_base           21
                        mod_base = OTHER
                        note = 2'-Desoxyuridine
modified_base           23
                        mod_base = OTHER
                        note = 2'-Desoxyuridine
modified_base           44^45
                        mod_base = OTHER
                        note = Phosphorothioate bond
misc_feature            45
                        note = 3' C3 Spacer
SEQUENCE: 26
tcagacgtgt gctcntccga ncnnnncgnn nnnnnnnnnn nnnnt                   45

SEQ ID NO: 27           moltype = DNA   length = 47
FEATURE                 Location/Qualifiers
source                  1..47
                        mol_type = other DNA
                        organism = synthetic construct
misc_feature            47
                        note = 3' C3 Spacer
modified_base           15
                        mod_base = OTHER
                        note = 2'-Desoxyuridine
modified_base           20
                        mod_base = OTHER
                        note = 2'-Desoxyuridine
modified_base           45^46
                        mod_base = OTHER
                        note = Phosphorothioate bond
modified_base           46^47
                        mod_base = OTHER
                        note = Phosphorothioate bond
SEQUENCE: 27
ctacacgacg ctctnccgan ctnnnnnnnn nnnnnnnnnn nnnnaca                 47

SEQ ID NO: 28           moltype = DNA   length = 40
FEATURE                 Location/Qualifiers
source                  1..40
                        mol_type = other DNA
                        organism = synthetic construct
modified_base           8
                        mod_base = OTHER
                        note = 2'-Desoxyuridine
modified_base           15
                        mod_base = OTHER
                        note = 2'-Desoxyuridine
modified_base           23
                        mod_base = OTHER
                        note = 2'-Desoxyuridine
modified_base           39^40
                        mod_base = OTHER
                        note = Phosphorothioate bond
misc_feature            40
                        note = 3' C3 Spacer
SEQUENCE: 28
tcagacgngt gctcntccga tcnnnnnnnn nnnnnnnnnt                         40

SEQ ID NO: 29           moltype = DNA   length = 23
FEATURE                 Location/Qualifiers
source                  1..23
                        mol_type = other DNA
                        organism = synthetic construct
misc_feature
                        note = 5' Phosphate
misc_feature            23
```

```
                        note = 3' Phosphate
SEQUENCE: 29
agatcggaag agcacacgtc tga                                          23

SEQ ID NO: 30           moltype = DNA  length = 47
FEATURE                 Location/Qualifiers
source                  1..47
                        mol_type = other DNA
                        organism = synthetic construct
modified_base           15
                        mod_base = OTHER
                        note = 2'-Desoxyuridine
modified_base           20
                        mod_base = OTHER
                        note = 2'-Desoxyuridine
modified_base           45^46
                        mod_base = OTHER
                        note = Phosphorothioate bond
modified_base           46^47
                        mod_base = OTHER
                        note = Phosphorothioate bond
misc_feature            47
                        note = 3C spacer
SEQUENCE: 30
ctacacgacg ctctnccgan ctnnnnnnnn nnnnnnnnnn nnnnaca               47

SEQ ID NO: 31           moltype = DNA  length = 22
FEATURE                 Location/Qualifiers
source                  1..22
                        mol_type = other DNA
                        organism = synthetic construct
misc_feature
                        note = 5' Phosphate
misc_feature            22
                        note = 3' Phosphate
SEQUENCE: 31
agatcggaag agcgtcgtgt ag                                           22

SEQ ID NO: 32           moltype = RNA  length = 53
FEATURE                 Location/Qualifiers
source                  1..53
                        mol_type = other RNA
                        organism = synthetic construct
modified_base           4
                        mod_base = m5u
modified_base           9
                        mod_base = m5u
modified_base           14
                        mod_base = m5u
modified_base           21
                        mod_base = m5u
modified_base           23
                        mod_base = m5u
modified_base           26
                        mod_base = m5u
modified_base           28..29
                        mod_base = m5u
modified_base           34
                        mod_base = m5u
modified_base           36
                        mod_base = m5u
modified_base           53
                        mod_base = m5u
misc_feature            13^14
                        note = C18 Spacer between residues
misc_feature            53
                        note = 3' C3 Spacer
modified_base           52^53
                        mod_base = OTHER
                        note = Phosphorothioate bond
SEQUENCE: 32
agancggang agcncagacg ngngcncnnc gancnnnnn nnnnnnnnnn nnn           53

SEQ ID NO: 33           moltype = RNA  length = 60
FEATURE                 Location/Qualifiers
source                  1..60
                        mol_type = other RNA
                        organism = synthetic construct
modified_base           4
```

```
                        mod_base = m5u
modified_base           9
                        mod_base = m5u
modified_base           15
                        mod_base = m5u
modified_base           25
                        mod_base = m5u
modified_base           27..28
                        mod_base = m5u
modified_base           33
                        mod_base = m5u
modified_base           35
                        mod_base = m5u
misc_feature            13^14
                        note = C18 Spacer between residues
modified_base           60
                        mod_base = OTHER
                        note = 3' C3 Spacer
modified_base           58^59
                        mod_base = OTHER
                        note = Phosphorothioate bond
modified_base           59^60
                        mod_base = OTHER
                        note = Phosphorothioate bond
misc_feature            33
                        note = 3' C3 Spacer
SEQUENCE: 33
agancggang agccnacacg acgcncnncc gancnnnnnn nnnnnnnnnn nnnnnnnaca    60

SEQ ID NO: 34           moltype = DNA  length = 70
FEATURE                 Location/Qualifiers
source                  1..70
                        mol_type = other DNA
                        organism = synthetic construct
modified_base           7
                        mod_base = OTHER
                        note = 2'-Desoxyuridine
modified_base           12
                        mod_base = OTHER
                        note = 2'-Desoxyuridine
modified_base           42
                        mod_base = OTHER
                        note = 2'-Desoxyuridine
modified_base           48
                        mod_base = OTHER
                        note = 2'-Desoxyuridine
modified_base           50
                        mod_base = OTHER
                        note = 2'-Desoxyuridine
misc_feature            16^17
                        note = C18 Spacer between residues
misc_feature            70
                        note = 3' C3 Spacer
modified_base           69^70
                        mod_base = OTHER
                        note = Phosphorothioate bond
SEQUENCE: 34
cgaagancgg angagcgtct gaaaaaatca gacgtgtgct cntccgancn tcgnnnnnnn    60
nnnnnnnnng                                                           70

SEQ ID NO: 35           moltype = DNA  length = 43
FEATURE                 Location/Qualifiers
source                  1..43
                        mol_type = other DNA
                        organism = synthetic construct
modified_base           4
                        mod_base = OTHER
                        note = 2'-Desoxyuridine
modified_base           9
                        mod_base = OTHER
                        note = 2'-Desoxyuridine
modified_base           18
                        mod_base = OTHER
                        note = 2'-Desoxyuridine
modified_base           24
                        mod_base = OTHER
                        note = 2'-Desoxyuridine
modified_base           26
                        mod_base = OTHER
```

```
                              note = 2'-Desoxyuridine
modified_base                 42^43
                              mod_base = OTHER
                              note = Phosphorothioate bond
misc_feature                  13^14
                              note = 3' C3 Spacer C18 Spacer between residues
misc_feature                  43
                              note = 3' C3 Spacer
SEQUENCE: 35
agancggang agcgctcntc cgancnnnnn nnnnnnnnnn nnt                              43

SEQ ID NO: 36                 moltype = DNA  length = 43
FEATURE                       Location/Qualifiers
source                        1..43
                              mol_type = other DNA
                              organism = synthetic construct
modified_base                 3
                              mod_base = OTHER
                              note = 2'-Desoxyuridine
modified_base                 11
                              mod_base = OTHER
                              note = 2'-Desoxyuridine
modified_base                 14
                              mod_base = OTHER
                              note = 2'-Desoxyuridine
modified_base                 16
                              mod_base = OTHER
                              note = 2'-Desoxyuridine
modified_base                 22
                              mod_base = OTHER
                              note = 2'-Desoxyuridine
modified_base                 42^43
                              mod_base = OTHER
                              note = Phosphorothioate bond
misc_feature                  13^14
                              note = C18 Spacer between residues
misc_feature                  43
                              note = 3' C3 Spacer
SEQUENCE: 36
tcnagcctac ncgncnagcc tnctcgnnnn nnnnnnnnnn nnt                              43

SEQ ID NO: 37                 moltype = DNA  length = 70
FEATURE                       Location/Qualifiers
source                        1..70
                              mol_type = other DNA
                              organism = synthetic construct
modified_base                 7
                              mod_base = OTHER
                              note = 2'-Desoxyuridine
modified_base                 12
                              mod_base = OTHER
                              note = 2'-Desoxyuridine
modified_base                 42
                              mod_base = OTHER
                              note = 2'-Desoxyuridine
modified_base                 48
                              mod_base = OTHER
                              note = 2'-Desoxyuridine
modified_base                 50
                              mod_base = OTHER
                              note = 2'-Desoxyuridine
modified_base                 69^70
                              mod_base = OTHER
                              note = Phosphorothioate bond
misc_feature                  70
                              note = 3' C3 Spacer
misc_feature                  16^17
                              note = C18 Spacer between residues
SEQUENCE: 37
gtcagancgg angagcgtct gaaaaaatca gacgtgtgct cntccgancn gacnnnnnn           60
nnnnnnnnng                                                                 70

SEQ ID NO: 38                 moltype = DNA  length = 31
FEATURE                       Location/Qualifiers
source                        1..31
                              mol_type = other DNA
                              organism = synthetic construct
modified_base                 30^31
                              mod_base = OTHER
```

```
                        note = Phosphorothioate bond
SEQUENCE: 38
gtgactggag ttcagacgtg tgctcttccg a                                   31

SEQ ID NO: 39           moltype = DNA   length = 58
FEATURE                 Location/Qualifiers
source                  1..58
                        mol_type = other DNA
                        organism = synthetic construct
SEQUENCE: 39
aatgatacgg cgaccaccga gatctacact ctttccctac acgacgctct tccgatct      58

SEQ ID NO: 40           moltype = DNA   length = 64
FEATURE                 Location/Qualifiers
source                  1..64
                        mol_type = other DNA
                        organism = synthetic construct
modified_base           62^63
                        mod_base = OTHER
                        note = Phosphorothioate bond
modified_base           63^64
                        mod_base = OTHER
                        note = Phosphorothioate bond
SEQUENCE: 40
caagcagaag acggcatacg agatcgtgat gtgactggag ttcagacgtg tgctcttccg    60
atct                                                                 64

SEQ ID NO: 41           moltype = DNA   length = 22
FEATURE                 Location/Qualifiers
source                  1..22
                        mol_type = other DNA
                        organism = synthetic construct
SEQUENCE: 41
aacctctcta tgggcagtcg gt                                             22

SEQ ID NO: 42           moltype = DNA   length = 61
FEATURE                 Location/Qualifiers
source                  1..61
                        mol_type = other DNA
                        organism = synthetic construct
modified_base           59^60
                        mod_base = OTHER
                        note = Phosphorothioate bond
modified_base           60^61
                        mod_base = OTHER
                        note = Phosphorothioate bond
SEQUENCE: 42
caagcagaag acggcatacg agatcgtgat gacgctctcc tctctatggg cagtcggtga    60
t                                                                    61

SEQ ID NO: 43           moltype = DNA   length = 24
FEATURE                 Location/Qualifiers
source                  1..24
                        mol_type = other DNA
                        organism = synthetic construct
misc_feature
                        note = 5' C3 Spacer
SEQUENCE: 43
caagcagaag acggcatacg agat                                           24

SEQ ID NO: 44           moltype = DNA   length = 58
FEATURE                 Location/Qualifiers
source                  1..58
                        mol_type = other DNA
                        organism = synthetic construct
SEQUENCE: 44
aatgatacgg cgaccaccga gatctacact ctttccctac acgacgctct tccgatct      58
```